US012440444B2

(12) United States Patent
Badylak et al.

(10) Patent No.: US 12,440,444 B2
(45) Date of Patent: Oct. 14, 2025

(54) MATRIX BOUND VESICLES (MBVS) CONTAINING IL-33 AND THEIR USE

(71) Applicant: University of Pittsburgh— Of the Commonwealth System of Higher Education, Pittsburgh, PA (US)

(72) Inventors: Stephen Francis Badylak, West Lafayette, IN (US); George S. Hussey, Cranberry Township, PA (US); Heth Turnquist, Pittsburgh, PA (US); Jenna Lynn Dziki, Pittsburgh, PA (US); Quan Liu, Shenzhen (CN); Zhongqiang Zhang, Changsha (CN)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 1085 days.

(21) Appl. No.: 17/052,034

(22) PCT Filed: May 3, 2019

(86) PCT No.: PCT/US2019/030547
§ 371 (c)(1),
(2) Date: Oct. 30, 2020

(87) PCT Pub. No.: WO2019/213482
PCT Pub. Date: Nov. 7, 2019

(65) Prior Publication Data

US 2021/0106526 A1 Apr. 15, 2021

Related U.S. Application Data

(60) Provisional application No. 62/666,624, filed on May 3, 2018.

(51) Int. Cl.
*A61P 9/10* (2006.01)
*A61K 9/127* (2006.01)
(Continued)

(52) U.S. Cl.
CPC .......... *A61K 9/127* (2013.01); *A61K 31/7105* (2013.01); *A61K 38/20* (2013.01);
(Continued)

(58) Field of Classification Search
CPC .... A61K 9/127; A61K 31/7105; A61K 38/20; A61K 38/44; A61K 45/06; A61L 27/3633; A61P 9/10; C12Y 104/03013
See application file for complete search history.

(56) References Cited

U.S. PATENT DOCUMENTS 4,902,508 A 2/1990 Badylak et al.
4,956,178 A 9/1990 Badylak et al.
(Continued)

FOREIGN PATENT DOCUMENTS

JP 2012-518041 A 8/2012
JP 2013-536246 A 9/2013
(Continued)

OTHER PUBLICATIONS

Lee, Younjin. "Matrix-bound Nanovesicles as an Extracellular Source of Lysyl Oxidase". 2020. [retrieved online] URL: https://d-scholarship.pitt.edu/39304/ (Year: 2020).*
(Continued)

*Primary Examiner* — Thomas J. Visone
*Assistant Examiner* — Georgiana C Reglas
(74) *Attorney, Agent, or Firm* — Klarquist Sparkman, LLP; Susan Alpert Siegel; Gregory K. Scott

(57) ABSTRACT

Methods are disclosed for treating a subject with a disorder, such as, but not limited to, a) fibrosis of an organ or tissue; b) solid organ transplant rejection; or c) a cardiac disease that is not myocardial infarction or myocardial ischemia. These methods include selecting a subject having or at risk of having the disorder, and administering to the subject a therapeutically effective amount of isolated nanovesicles
(Continued)

derived from an extracellular matrix, wherein the nanovesicles contain interleukin (IL)-33 and comprise lysyl oxidase, and wherein the nanovesicles a) do not express CD63 or CD81, or b) are $CD63^{lo}CD81^{lo}$. In additional embodiments, methods are disclosed for increasing myoblast differentiation.

15 Claims, 21 Drawing Sheets

Specification includes a Sequence Listing.

(51) Int. Cl.

| | |
|---|---|
| ***A61K 31/7105*** | (2006.01) |
| ***A61K 38/20*** | (2006.01) |
| ***A61K 38/44*** | (2006.01) |
| ***A61K 45/06*** | (2006.01) |
| ***A61L 27/36*** | (2006.01) |

(52) U.S. Cl.

CPC .............. *A61K 38/44* (2013.01); *A61K 45/06* (2013.01); *A61L 27/3633* (2013.01); *A61P 9/10* (2018.01); *C12Y 104/03013* (2013.01)

(56) References Cited

U.S. PATENT DOCUMENTS

| | | | |
|---|---|---|---|
| 4,978,668 | A | 12/1990 | Babbs et al. |
| 5,007,927 | A | 4/1991 | Badylak et al. |
| 5,281,422 | A | 1/1994 | Badylak et al. |
| 5,352,463 | A | 10/1994 | Badylak et al. |
| 5,372,821 | A | 12/1994 | Badylak et al. |
| 5,516,533 | A | 5/1996 | Badylak et al. |
| 5,554,389 | A | 9/1996 | Badylak et al. |
| 5,573,784 | A | 11/1996 | Badylak et al. |
| 5,641,518 | A | 6/1997 | Badylak et al. |
| 5,645,860 | A | 7/1997 | Knapp et al. |
| 5,753,267 | A | 5/1998 | Badylak et al. |
| 5,762,966 | A | 6/1998 | Knapp et al. |
| 5,771,969 | A | 6/1998 | Garay |
| 5,866,414 | A | 2/1999 | Badylak et al. |
| 5,955,110 | A | 9/1999 | Patel et al. |
| 5,968,096 | A | 10/1999 | Whitson et al. |
| 6,096,347 | A | 8/2000 | Geddes et al. |
| 6,099,567 | A | 8/2000 | Badylak et al. |
| 6,126,686 | A | 10/2000 | Badylak et al. |
| 6,187,039 | B1 | 2/2001 | Hiles et al. |
| 6,241,981 | B1 | 6/2001 | Cobb et al. |
| 6,375,989 | B1 | 4/2002 | Badylak et al. |
| 6,485,723 | B1 | 11/2002 | Badylak et al. |
| 6,576,265 | B1 | 6/2003 | Spievack |
| 6,579,538 | B1 | 6/2003 | Spievack |
| 6,696,270 | B2 | 2/2004 | Badylak et al. |
| 6,783,776 | B2 | 8/2004 | Spievack |
| 6,793,939 | B2 | 9/2004 | Badylak |
| 6,849,273 | B2 | 2/2005 | Spievack |
| 6,852,339 | B2 | 2/2005 | Spievack |
| 6,861,074 | B2 | 3/2005 | Spievack |
| 6,887,495 | B2 | 5/2005 | Spievack |
| 6,890,562 | B2 | 5/2005 | Spievack |
| 6,890,563 | B2 | 5/2005 | Spievack |
| 6,890,564 | B2 | 5/2005 | Spievack |
| 6,893,666 | B2 | 5/2005 | Spievack |
| 6,918,396 | B1 | 7/2005 | Badylak et al. |
| 7,771,717 | B2 | 8/2010 | Badylak et al. |
| 7,776,596 | B2 | 8/2010 | Badylak |
| 7,815,686 | B2 | 10/2010 | Badylak |
| 7,820,634 | B2 | 10/2010 | Badylak et al. |
| 8,003,131 | B2 | 8/2011 | Badylak |
| 8,084,048 | B2 | 12/2011 | Badylak |
| 8,409,625 | B2 | 4/2013 | Badylak |
| 8,535,719 | B2 | 9/2013 | Badylak et al. |
| 9,277,999 | B2 | 3/2016 | Badylak et al. |
| 9,314,340 | B2 | 4/2016 | Badylak et al. |
| 9,480,776 | B2 | 11/2016 | Badylak et al. |
| 9,861,662 | B2 | 1/2018 | Badylak et al. |
| 10,092,676 | B2 | 10/2018 | Amoroso et al. |
| 10,213,526 | B2 | 2/2019 | Badylak et al. |
| 2004/0187877 | A1 | 9/2004 | Badylak et al. |
| 2004/0191226 | A1 | 9/2004 | Badylak |
| 2009/0053279 | A1 | 2/2009 | Badylak et al. |
| 2010/0297212 | A1 | 11/2010 | Badylak |
| 2011/0097378 | A1 | 4/2011 | Badylak |
| 2011/0184439 | A1 | 7/2011 | Anderson et al. |
| 2014/0031256 | A1 | 1/2014 | Lim |
| 2014/0356331 | A1 | 12/2014 | Badylak et al. |
| 2015/0297798 | A1 | 10/2015 | Badylak et al. |
| 2018/0125897 | A1 | 5/2018 | Badylak et al. |
| 2018/0243473 | A1 | 8/2018 | Badylak et al. |
| 2019/0015552 | A1 | 1/2019 | Badylak et al. |
| 2019/0038803 | A1 | 2/2019 | Badylak et al. |
| 2019/0076574 | A1 | 3/2019 | Ramer et al. |
| 2019/0117837 | A1 * | 4/2019 | Badylak .................. A61L 27/54 |

FOREIGN PATENT DOCUMENTS

| | | | | |
|---|---|---|---|---|
| WO | WO-200015765 | A1 | 3/2000 | |
| WO | WO-200032209 | A2 | 6/2000 | |
| WO | WO-200032254 | A1 | 6/2000 | |
| WO | WO 2005/079844 | A2 | 9/2005 | |
| WO | WO 2010/096458 | A1 | 8/2010 | |
| WO | WO 2012/027514 | A2 | 3/2012 | |
| WO | WO-2012108842 | A1 | 8/2012 | |
| WO | WO-2014168964 | A1 | 10/2014 | |
| WO | WO-2015164728 | A1 | 10/2015 | |
| WO | WO-2015179227 | A1 | 11/2015 | |
| WO | WO 2016/197038 | A1 | 8/2016 | |
| WO | WO-2017011299 | A1 | 1/2017 | |
| WO | WO-2017049167 | A1 | 3/2017 | |
| WO | WO-2017151862 | A1 * | 9/2017 | ......... A61K 31/7088 |
| WO | WO-2018161028 | A1 | 9/2018 | |
| WO | WO-2018161034 | A1 | 9/2018 | |
| WO | WO-2018187286 | A1 | 10/2018 | |
| WO | WO 2018/204848 | A1 | 11/2018 | |

OTHER PUBLICATIONS

Manni et al (Tissue Eng Part A. Nov. 2011;17(21-22):2795-804) (Year: 2011).*

Liu & Turnquist (Cytokine. May 2013;62(2):183-94) (Year: 2013).*

Zhu and Carver (Cytokine. Jun. 2012;58(3):368-79) (Year: 2012).*

Kong et al (Cell Mol Life Sci. Feb. 2014;71(4):549-74) (Year: 2014).*

Lee, Y. "Matrix-bound Nanovesicles as an Extracellular Source of Lysyl Oxidase". 2020. Retrieved online Oct. 1, 2023 URL: https://d-scholarship.pitt.edu/39304/ (Year: 2020).*

Spagnolo et al (Pharmacology & Therapeutics vol. 152, Aug. 2015, pp. 18-27) (Year: 2015).*

Segura et al (Pharmacology & Therapeutics vol. 152, Aug. 2015, pp. 18-27) (Year: 2015).*

Mamalis et al (J. Biophotonics9, No. 11-12, 1167-1179 (2016)) (Year: 2016).*

Suzuki et al (Circ J 2010; 74: 233-239) (Year: 2010).*

Verleden et al (J Thorac Dis. Aug. 2017; 9(8): 2650-2659) (Year: 2017).*

Tolle et al (Eur J Clin Invest 2015; 45 (9): 976-985) (Year: 2015).*

Kish (P T. Dec. 2017;42(12):764-766) (Year: 2017).*

Huleihel et al (Sci Adv. Jun. 10, 2016;2(6):e1600502) (Year: 2016).*

Brunner et al (Interleukin-33 prolongs allograft survival during chronic cardiac rejection. Transpl Int. Oct. 2011;24(10):1027-39) (Year: 2011).*

Burzyn et al., "A special population of regulatory T cells potentiates muscle repair," *Cell* 155(6): 1282-1295 (Dec. 5, 2013).

Hussey et al., "Il-33 as a key signaling molecule for the therapeutic effects of ECM bioscaffolds for cardiac repair," *Tissue Engineering Part A*. 23 (Supplement 1): 1937-3341 Dec. 1, 2017) (Abstract No. 107).

(56) References Cited

OTHER PUBLICATIONS

International Search Report and Written Opinion from parent PCT Application No. PCT/US2019/030547, 12 pages (mailed Aug. 12, 2019).
Kuswanto et al., "Poor repair of skeletal muscle in aging mice reflects a defect in local, interleukin-33-dependent, accumulation of regulatory T cells," *Cell* 44(2) 355-367 (Feb. 16, 2016).
Turnquist et al., "IL-33 expands suppressive $CD11b^{+}Gr\text{-}1^{int}$ and regulatory T cells (Treg), including $ST2L^{+}Foxp3^{+}$cells, and mediates Treg-dependent promotion of cardiac allograft survival," *J. Immunol.* 187(9): 4598-4610 (Nov. 1, 2011).
Wynn and Ramalingam, "Mechanisms of fibrosis: therapeutic translation for fibrotic disease," *Nature medicine* 18(7): 1028-1040 (2012).
Dziki, et al., "Extracellular matrix bioscaffolds as immunomodulatory biomaterials," *Tissue Engineering: Part A* 23 (19 -20): 1152-1163 (2017).
Hussey, et al., "Matrix bound nanovesicle-associated IL-33 activates a pro-remodeling macrophage phenotype via a non-canonical, ST2-independent pathway," *J. Immunol. and Regen. Med.* 3:26-35 (2019).
Office Action from corresponding Chinese Patent Application No. 201980030111.8 (in Chinese with English language translation), 7 pages (mailed Feb. 24, 2023).
Pei, Z., "Effect and mechanisms of suppressor of cytokine signaling 3 on chronic rejection of heart transplantation," Doctoral dissertation, cardiovascular surgery. Huazhong University of Science & Technology, Wuhan, China, E066-23 (May 2014).
Zhu and Carver. "Effects of interleukin-33 on cardiac fibroblast gene expression and activity," Cytokine 58, 368-379 (e-PUB Mar. 23, 2012).
Altrock et al., "Inhibition of fibronectin disposition improves experimental liver fibrosis," *J Hepatol* 62(3):625-633, E-pub Jun. 16, 2014.
Bitterman et al., "Role of fibronectin in fibrotic lung disease," *Chest* 83(5):96S, May 1983 (abstract).
Eurofins Discovery, "BioMAP fibrosis panel," 3 pages, Accessed Apr. 15, 2024.
Ghonim et al., "Pulmonary inflammation and fibroblast immunoregulation: from bench to bedside," *J Clin Invest* 133(17):e170499, E-pub Sep. 1, 2023.
Jong et al., "Exosomes from hypoxic endothelial cells have increased collagen crosslinking activity through up-regulation of lysyl oxidase-like 2," *J Cell Mol Med* 20(2):342-350, E-pub Nov. 27, 2015.
Li et al., "Adipose tissue-derived stem cells suppress hypertrophic scar fibrosis via the p38/MAPK signaling pathway," *Stem Cell Res Ther* 7(1):102, Aug. 2, 2016.
Mayo Foundation for Medical Education and Research (MFMER), "Pulmonary fibrosis," *Mayo Clinic-Diseases and Condition*, 17 pages, Accessed Apr. 15, 2024.
Nakano et al., "Fibrosis-related gene expression in single ventricle heart disease," J Pediatr. 191:82-90, E-pub Oct. 16, 2017.
Pandit et al., "Inhibition and role of let-7d in idiopathic pulmonary fibrosis," *Am J Respir Crit Care Med* 182(2):220-229, E-pub Apr. 15, 2010.
Shah et al., "A review of Pirfenidone as an anti-fibrotic in idiopathic pulmonary fibrosis and its probable role in other disease," *Cureus* 13(1):e12482, E-pub Jan. 4, 2021.
van den Blink et al., "Recombinant human pentraxin-2 therapy in patient with idiopathic pulmonary fibrosis: safety, pharmacokinetics and exploratory efficacy," *Eur Respir J* 47(3): 889-897, E-pub Feb. 12, 2016.
Wang et al., "Attenuation of fibrosis in vitro and in vivo with SPARC siRNA," *Arthritis Research Ther* 12(2):R60, E-pub Apr. 1, 2010.
Wynn and Vannella, "Macrophage in tissue repair, regeneration, and fibrosis," *Immunity* 44(3):450-462: Mar. 15, 2016.
Xu et al., "Inhibition of HIF-1$\alpha$ attenuates silica-induced pulmonary fibrosis," *Int J Environ Res Public Heath* 19(11):6675, E-pub Jun. 1, 2022.
Ali et al., "Isolation and characterization of calcifying matrix vesicles from epiphyseal cartilage," *Proceedings of the National Academy of Sciences of the United States of America* 67(3):1513-1520, Nov. 1970.
Ali, "Analysis of matrix vesicles and their role in the calcification of epiphyseal cartilage," *Federation Proceedings* 35(2):135-42, Feb. 1976.
Ali, "Matrix vesicles and apatite nodules in arthritic cartilage," Chapter 15 in: *Perspectives in Inflammation: Future Trends in Inflammation*, Willoughby et al., (eds), University Park Press, Baltimore, MD, pp. 211-233, 1977.
Anderson, "Molecular biology of matrix vesicles," *Clinical orthopaedics and related research*, 314:266-80, May 1995.
Anderson, "Vesicles associated with calcification in the matrix of epiphyseal cartilage," *The Journal of cell biology* 41(1):59-72, Apr. 1969.
Anderson, "Matrix vesicles and calcification," *Current rheumatology reports* 5(3):222-6, Jun. 2003.
Bab et al., "Ultrastructural and biochemical study of extracellular vesicles in normal alveolar bone of rats," *J. Cell Tissue Res.* 202:1-7, Oct. 1979.
Badylak et al., "Small intestinal submucosa as a large diameter vascular graft in the dog." *The Journal of surgical research* 47(1):74-80, Jul. 1989.
Badylak, "Decellularized allogeneic and xenogeneic tissue as a bioscaffold for regenerative medicine: factors that influence the host response," *Annals of Biomedical Engineering* 42(7):1517-27, Jul. 2014.
Badylak et al., "The use of extracellular matrix as an inductive scaffold for the partial replacement of functional myocardium," *Cell transplantation* 15(S1):S29-40, 2006.
Badylak et al., "Extracellular matrix as a biological scaffold material: Structure and function," *Acta Biomaterialia* 5(1):1-13, Jan. 2009.
Ben-Dov et al., "Cell and Microvesicle Urine microRNA Deep Sequencing Profiles from Healthy Individuals: Observations with Potential Impact on Biomarker Studies," *PloS one* 11(1):e0147249, Jan. 2016.
Bobrie et al., "Exosome secretion: molecular mechanisms and roles in immune responses," *Traffic(Copenhagen, Denmark)* 12(12):1659-68, Dec. 2011.
Böing et al. "Single-step isolation of extracellular vesicles by size-exclusion chromatography," *Journal of extracellular vesicles* 3:eCollection, Sep. 2014.
Brown et al., "Macrophage phenotype as a predictor of constructive remodeling following the implantation of biologically derived surgical mesh materials," *Acta biomaterialia* 8(3):978-87, Mar. 2012.
Brown et al., "Performance of SynerGraft decellularized pulmonary homograft in patients undergoing a Ross procedure," *The Annals of thoracic surgery* 91(2):416-22; discussion 422-3, Feb. 2011.
Cayrol et al., "Environmental allergens induce allergic inflammation through proteolytic maturation of IL-33," *Nature immunology* 19(4): 375-385, Mar. 2018.
ClinicalTrials.gov Study ID No. NCT02305602 "A Study of VentriGel in Post-MI Patients," Apr. 26, 2018, accessible at https://clinicaltrials.gov/study/NCT02305602 (11 pages).
Crapo et al., "Small intestinal submucosa gel as a potential scaffolding material for cardiac tissue engineering," *Acta biomaterialia* 6(6):2091-6, Jun. 2010.
De Jong et al., "Extracellular vesicles: potential roles in regenerative medicine," *Frontiers in Immunology* 5(608): pp. 1-13, Dec. 2014.
De Jong et al., "Exosomes from hypoxic endothelial cells have increased collagen crosslinking activity through up-regulation of lysyl oxidase-like 2," *Journal of cellular and molecular medicine* 20(2):342-50, Feb. 2016.
Deatherage et al., "Membrane vesicle release in bacteria, eukaryotes, and archaea: a conserved yet underappreciated aspect of microbial life," *Infection and immunity* 80(6): 1948-57, Mar. 2012.
Deutsch et al., "Purification and further characterization of isolated matrix vesicles from rat alveolar bone," *Metabolic Bone Disease and Related Research* 3(3):209-214, 1981.

(56) References Cited

OTHER PUBLICATIONS

Deutsch et al., "Purification and further characterization of isolated matrix vesicles from rat alveolar bone," *Metabolic Bone Disease and Related Research* 3(3):209-214, 1981 (Abstract only).
Dharmapuram, Anil et al. "Preliminary Experience With the Use of an Extracellular Matrix to Augment the Native Pulmonary Valve During Repair of Tetralogy of Fallot." *World journal for pediatric & congenital heart surgery* 8(2):174-181, 2017.
Diaz et al., "Changes in the Membrane-Associated Proteins of Exosomes Released from Human Macrophages after Mycobacterium tuberculosis Infection," *Scientific reports* 6(37975), Nov. 2016.
Dziki et al., "Extracellular Matrix for Myocardial Repair." *Advances in experimental medicine and biology* 1098:151-171, 2018.
Escola et al., "Selective enrichment of tetraspan proteins on the internal vesicles of multivesicular endosomes and on exosomes secreted by human B- lymphocytes," *The Journal of biological chemistry* 273(32):20121-7, Aug. 1998.
Frangogiannis et., "The inflammatory response in myocardial injury, repair, and remodelling," *Nature reviews. Cardiology* 11(5):255-65, 2014.
French et al., "A naturally derived cardiac extracellular matrix enhances cardiac progenitor cell behavior in vitro," *Acta Biomater.* 8(12):4357-4364, 2012.
Gerdisch et al., "Clinical experience with CorMatrix extracellular matrix in the surgical treatment of mitral valve disease," *The Journal of thoracic and cardiovascular surgery* 148(4):1370-8, 2014.
Gibson et al., "Tissue extracellular matrix nanoparticle presentation in electrospun nanofibers," *BioMed Research International* 2014(Article ID 469120): pp. 1-13, May 2014.
Gilbert et al. "Production and characterization of ECM powder; implications for tissue engineering applications." *Biomaterials* 26(12):1431-5, 2005.
Gohr et al., "Calcific tendonitis: A model," *Connective Tissue Research* 48(6):286-291, 2007.
Greening et al., "A protocol for exosome isolation and characterization: Evaluation of ultracentrifugation, density-gradient separation, and immunoaffinity capture methods," *Proteomic Profiling: Methods and Protocols* 1295:179-209, 2015.
Hernandez et al., "Designing Acellular Injectable Biomaterial Therapeutics for Treating Myocardial Infarction and Peripheral Artery Disease." *JACC. Basic to translational science* 2(2):212-226, 2017.
Hirschman et al., "Neutral peptidase activities in matrix vesicles from bovine fetal alveolar bone and dog osteosarcoma," *Calcified Tissue International* 35(6):791-797, Sep. 1983.
Huang et al. "Characterization of human plasma-derived exosomal RNAs by deep sequencing," *BMC genomics* 14(319): 14 pages, May 2013,.
Hulcihel et al., "Macrophage phenotype in response to ECM bioscaffolds," *Seminars in immunology* 29:2-13, Feb. 2017.
Huleihel et al. "Matrix-Bound Nanovesicles Recapitulate Extracellular Matrix Effects on Macrophage Phenotype," *Tissue engineering*. Part A 23(21-22):1283-1294, 2017.
Hussey et al. "Extracellular Matrix Bioscaffolds for Building Gastrointestinal Tissue," *Cellular and molecular gastroenterology and hepatology* 5(1):1-13, Sep. 2017.
Kapustin et al., "Vascular smooth muscle cell calcification is mediated by regulated exosome secretion," *Circulation Research* 116(8):1312-1323, ePub Feb. 2015.
Keane et al.. "Methods of tissue decellularization used for preparation of biologic scaffolds and in vivo relevance." *Methods* (*San Diego, Calif.*) 84:25-34, 2015.
Lamichhane et al., "Emerging roles for extracellular vesicles in tissue engineering and regenerative medicine," *Tissue engineering. Part B, Reviews* 21(1): 45-54, 2015.
Lefrançais et al. "IL-33 is processed into mature bioactive forms by neutrophil elastase and cathepsin G," *Proceedings of the National Academy of Sciences of the United States of America* 109(5)1673-8, 2012.
Libby et al., "Chronic rejection," *Immunity* 14(4):387-97, 2001.
Liew et al., "Interleukin-33 in health and disease." *Nature reviews. Immunology* 16(11): 676-689, Sep. 2016.
Liu et al., "IL-33-mediated IL-13 secretion by ST2+ Tregs controls inflammation after lung injury," *JCI insight* 4(6):e123919, Mar. 2019.
Liu et al., "Controlling the burn and fueling the fire: defining the role for the alarmin interleukin-33 in alloimmunity," *Current opinion in organ transplantation* 21(1): 45-52, Feb. 2016.
Malda et al., "Extracellular vesicles—new tool for joint repair and regeneration," *Nature Reviews* 12:244-249, Apr. 2016.
Martin et al., "Isolation and purification of extracellular matrix vesicles from blood vessels," P*reparative Biochemistry* 22(2):87-103, Jun. 1992.
Martinez et al., "The M1 and M2 paradigm of macrophage activation: time for reassessment," *F1000prime reports* 6(13):13, Mar. 2014.
Mase et al., "Clinical application of an acellular biologic scaffold for surgical repair of a large, traumatic quadriceps femoris muscle defect." *Orthopedics* 33(7):511, Jul. 2010.
Mu et al., "Host matrix modulation by tumor exosomes promotes motility and invasiveness," *Neoplasia* 15(8): 875-887, Aug. 2013.
Muhlrad et al., "Occurrence of actin-like protein in extracellular matrix vesicles," *Calcif Tissue Int.* 34(4): 376-381, Jul. 1982.
Oboki et al., "IL-33 is a crucial amplifier of innate rather than acquired immunity," *Proceedings of the National Academy of Sciences of the United States of America* 107(43):18581-6, Oct. 2010.
Oliveira et al., "Evaluation of small intestine grafts decellularization methods for corneal tissue engineering," *PloS one* 8(6):e66538, Jun. 2013.
Reing et al. "The effects of processing methods upon mechanical and biologic properties of porcine dermal extracellular matrix scaffolds," *Biomaterials* 31(33):8626-33, Nov. 2010.
Robinson et al., "Extracellular matrix scaffold for cardiac repair." *Circulation* 112(9 Suppl): 1135-43, Aug. 2005.
Rutnam et al., "miRNAs regulate expression and function of extracellular matrix Molecules," *Matrix Biol.* 32(2):74-85, Mar. 2013.
Sabin and Kikyo, "Microvesicles as mediators of tissue regeneration," *Translational Research* 163(4):286-295, Oct. 2013.
Scholl et al. "Preliminary experience with cardiac reconstruction using decellularized porcine extracellular matrix scaffold: human applications in congenital heart disease." *World journal for pediatric & congenital heart surgery* 1(1):132-6, Apr. 2010.
Schurgers et al., "Initiation and propagation of vascular calcification is regulated by a concert of platelet- and smooth muscle cell-derived extracellular vesicles," *Frontiers in Cardiovascular Medicine* 5(36):13 pages, Apr. 2018.
Seif-Naraghi et al., "Design and characterization of an injectable pericardial matrix gel: a potentially autologous scaffold for cardiac tissue engineering," *Tissue Eng Part A.* 16(6):2017-2027, Jun. 2010.
Sela et al., "Ultrastructural and biochemical characterization of extracellular matrix vesicles in healing alveolar bone sockets: preliminary indications for the presence of contractile proteins," *Metab. Bone Dis. and Rel. Res.* 1(3):185-191, 1978.
Serrels et al., "IL-33 and ST2 mediate FAK-dependent antitumor immune evasion through transcriptional networks," *Science signaling* 10(508):eaan8355, Dec. 2017.
Shapiro et al., "Matrix Vesicles: Are they anchored exosomes?," *Bone* 79:29-36, Oct. 2015.
Singelyn et al., "Naturally derived myocardial matrix as an injectable scaffold for cardiac tissue engineering," *Biomaterials* 30(29):5409-5416, Oct. 2009,.
Suthahar et al., "From Inflammation to Fibrosis-Molecular and Cellular Mechanisms of Myocardial Tissue Remodelling and Perspectives on Differential Treatment Opportunities," *Current heart failure reports* 14(4):235-250, 2017.
Théry et al., "Molecular characterization of dendritic cell-derived exosomes. Selective accumulation of the heat shock protein hsc73," *The Journal of cell biology* 147(3):599-610, 1999.

(56) References Cited

OTHER PUBLICATIONS

Théry et al., "Proteomic analysis of dendritic cell-derived exosomes: a secreted subcellular compartment distinct from apoptotic vesicles," *Journal of immunology(Baltimore, Md. : 1950)* 166(12):7309-18, Jun. 2001.
Thouverey et al., "Proteomic characterization of biogenesis and functions of matrix vesicles released from mineralizing human osteoblast-like cells," *Journal of Proteomics* 74:1123-1134, Apr. 2011.
Tian et al., "A doxorubicin delivery platform using engineered natural membrane vesicle exosomes for targeted tumor therapy," *Biomaterials* 35(7): 2383-2390, e-Pub Dec. 2013.
Tjota et al. "IL-33 Drives Monocyte Recruitment to Lung Interstitium through Chemokine Upregulation," *ImmunoHorizons* 1(6):101-108, Aug. 2017.
Townsend et al., "T1/ST2-deficient mice demonstrate the importance of T1/ST2 in developing primary T helper cell type 2 responses," *The Journal of experimental medicine* 191(6):1069-76, Mar. 2000.
Travers et al., "Cardiac Fibrosis: The Fibroblast Awakens." *Circulation research* 118(6):1021-40, Mar. 2016.
Ungerleider et al., "Concise review: injectable biomaterials for the treatment of myocardial infarction and peripheral artery disease: translational challenges and progress." *Stem cells translational medicine* 3(9):1090-9, Jul. 2014.
Väänänen et al., "Matrix vesicles in chicken epiphyseal cartilage. Separation from lysosomes and the distribution of inorganic pyrophosphatase activity," *Calcif. Tissue Int.* 28(1):65-72, Aug. 1979.
Van Amerongen et al., "The enzymatic degradation of scaffolds and their replacement by vascularized extracellular matrix in the murine myocardium," *Biomaterials* 27(10):2247-57, Apr. 2006.
van der Merwe et al., "Matrix-bound nanovesicles prevent ischemia-induced retinal ganglion cell axon degeneration and death and preserve visual function," *Scientific reports* 9(1):3482, Mar. 2019.
van der Pol et al., "Classification, functions, and clinical relevance of extracellular vesicles," *Pharmacological reviews* 64(3):676-705, Jun. 2012.
Wainwright et al., "Preparation of cardiac extracellular matrix from an intact porcine heart," *Tissue engineering. Part C, Methods* 16(3):525-32, Jun. 2010.
Wang et al., "Comparison of in vivo adipogenic capabilities of two different extracellular matrix microparticle scaffolds," *Plastic and Reconstructive Surgery* 131(2):174e-187e, Feb. 2013.
Wassenaar et al., "Evidence for Mechanisms Underlying the Functional Benefits of a Myocardial Matrix Hydrogel for Post-MI Treatment," *Journal of the American College of Cardiology* 67(9):1074-1086, Mar. 2016.
Wolf et al., "Immunomodulatory Extracellular Matrix Nanoparticles," *Tissue Engineering Part A, 21(Supplement 1):S-52 (Sep. 8-11, 2015, 4th TERMIS World Congress Boston, MA)*.
Wuthier et al., "Non-enzymatic isolation of matrix vesicles: characterization and initial studies on 45Ca and 32P-orthophosphate metabolism," *Metab. Bone Dis. And Rel. Res.* 1(2):125-136, 1978.
Xu et al., "Role of the IL-33-ST2 axis in sepsis." *Military Medical Research* 4(3), Feb. 2017.
Yáñez-Mó et al. "Biological properties of extracellular vesicles and their physiological functions," *Journal of extracellular vesicles* 4:27066, May 2015.
Zhang et al., "Artificial matrix helps neonatal cardiomyocytes restore injured myocardium in rats," Artificial organs 30(2):86-93, Feb. 2006.
Zhang et al., "Expression profiles of miRNAs in polarized macrophages," *International journal of molecular medicine* 31(4):797-802, Apr. 2013.
Zhou et al., "Label-free quantification proteomics reveals novel calcium binding proteins in matrix vesicles isolated from mineralizing Saos-2 cells," *BioScience Trends* 7(3):144-151, Jun. 2013.
Kopecky et al., "Donor Macrophages Modulate Rejection After Heart Transplantation," *Circulation* 146: 623-638 (Aug. 23, 2022).
Li et al., "The Evolving Roles of Macrophages in Organ Transplantation," *Journal of Immunology Research* 2019, 11 pages (Apr. 24, 2019).
Wu et al., "Magnetic Resonance Imaging Investigation of Macrophages in Acute Cardiac Allograft Rejection After Heart Transplantation," *Circ Cardiovasc Imaging* 6:965-973 (Nov. 2013).

* cited by examiner

SEQUENCE LISTING

<160> NUMBER OF SEQ ID NOS: 3

<210> SEQ ID NO 1
<211> LENGTH: 88
<212> TYPE: RNA
<213> ORGANISM: Homo sapiens

<400> SEQUENCE: 1
caccuugucc ucacggucca guuuucccag gaaucccuua gaugcuaaga uggggauucc 60
uggaaauacu guucuugagg ucaugguu 88

<210> SEQ ID NO 2
<211> LENGTH: 110
<212> TYPE: RNA
<213> ORGANISM: Homo sapiens

<400> SEQUENCE: 2
agaagggcua ucaggccagc cuucagagga cuccaaggaa cauucaacgc ugucggugag 60
uuugggauuu gaaaaaacca cugaccguug acuguaccuu gggguccuua 110

<210> SEQ ID NO 3
<211> LENGTH: 106
<212> TYPE: RNA
<213> ORGANISM: Homo sapiens

<400> SEQUENCE: 3
gcgcagcgcc cugucuccca gccugaggug cagugcugca ucucugguca guugggaguc 60
ugagaugaag cacuguagcu caggaagaga gaaguuguuc ugcagc 106

MATRIX BOUND VESICLES (MBVS) CONTAINING IL-33 AND THEIR USE

CROSS REFERENCE TO RELATED APPLICATION

This is a § 371 U.S. national stage of International Application No. PCT/US2019/030547, filed May 3, 2019, which claims the benefit of U.S. Provisional Application No. 62/666,624, filed May 3, 3018, which is incorporated by reference herein in its entirety.

STATEMENT OF GOVERNMENT SUPPORT

This invention was made with government support under grant nos. AR073527 and HL122489 awarded by the National Institutes of Health. The government has certain rights in the invention.

FIELD

This is related to the use of membrane bound nanovesicles (MBVs) containing interleukin (IL)-33 for the treatment of a) fibrosis of an organ or tissue, b) solid organ transplant rejection, and c) a cardiac disease.

SEQUENCE LISTING

The Sequence Listing, submitted as an ASCII text file [8123-100723-09_sequencelisting.txt, Oct. 28, 2020, 1,185 bytes], is incorporated by reference herein.

BACKGROUND

Cardiac disease or injury causes fibrosis that results in myocardial stiffness, loss of function, and heart failure (HF). Replacement fibrosis after myocardial ischemia (MI) arises as damaged cardiac myocytes are replaced by fibroblasts and associated excessive extracellular matrix (ECM) (Travers et al., *Circulation research* 118, 1021-1040 (2016)). Reactive interstitial fibrosis impacts areas around the microvasculature and local myocardium and contributes to chronic allograft rejection (CR) after heart transplant (HTx). CR causes the loss of >50% of grafts within 11 years post-transplant (Libby and Pober, *Immunity* 14, 387-397 (2001)). Excessive inflammation has been implicated in adverse cardiac remodeling and progression to HF. Numerous experimental studies have shown that a timely resolution of inflammation after MI or HTx may help prevent development and progression of immune-driven fibrosis (Frangogiannis, *Nature Reviews Cardiology* 11, 255 (2014); Suthahar, *Current Heart Failure Reports* 14, 235-250 (2017)). However, there are no effective therapeutic modalities available to prevent or reverse fibrosis due to cardiac injury after MI or ischemia-reperfusion injury (IRI) and immune-mediated attack after HTx.

Biologic scaffolds composed of mammalian extracellular matrix (ECM) have been developed as surgical mesh materials, powders for topical wound care, and hydrogels; all of which have been approved for a large number of clinical applications including aortic and mitral valve replacement (Gerdisch et al., *J. of thoracic and cardiovascular surgery* 148, 1370-1378 (2014); Brown et al., *The Annals of thoracic surgery* 91, 416-423 (2011)) reconstruction of congenital heart defects (Scholl et al., *World Journal for Pediatric and Congenital Heart Surgery* 1, 132-136 (2010)) and as a cardiac patch to augment the native pulmonary valve during primary repair of tetralogy of Fallot (TOF) (Dharmapuram et al., *World Journal for Pediatric and Congenital Heart Surgery* 8, 174-181 (2017)). An ECM hydrogel has been shown to directly promote endogenous repair of myocardium (Ungerleider & Christman; *Stem Cells Transl Med* 3, 1090-1099 (2014); Hernandez & Christman, *JACC Basic Transl Sci* 2, 212-226 (2017); Wassenaar et al., *J Am Coll Cardiol* 67, 1074-1086 (2016)) and is currently being investigated in a Phase I clinical trial for intracardiac injection to facilitate repair of cardiac tissue following myocardial infarction (ClinicalTrials.gov Identifier: NCT02305602). These ECM-based materials are most commonly xenogeneic in origin and are prepared by the decellularization of a source tissue such as dermis, urinary bladder or small intestinal submucosa (SIS), among others (Keane et al., *Methods* 84, 25-34 (2015)). Xenogeneic ECM scaffolds do not elicit an adverse innate or adaptive immune response, and in fact, support an anti-inflammatory and reparative innate and adaptive immune response (Huleihel et al., in *Seminars in Immunology,* 39:2-13 (2017)). Use of these naturally occurring biomaterials is typically associated with at least partial restoration of functional, site-appropriate tissue; a process referred to as "constructive remodeling" (Martinez et al., *F*1000*Prime Rep* 6:13 (2014)). Arguably, the major determinant of downstream functional remodeling outcome is the early innate immune response to ECM bioscaffolds (Brown, et al., *Acta Biomater,* 8:978-987 (2012)). ECM bioscaffolds, or the degradation products of ECM bioscaffolds, have been shown to direct tissue repair by promoting a transition from a pro-inflammatory M1-like macrophage and Th1 T cell phenotype to a pro-remodeling M2-like macrophage and T helper Type 2 (Th2) cell response (Huleihel, et al. *Seminars in Immunology,* 29:2-13 (2017)). Numerous studies have shown that an appropriately timed transition in macrophage activation state is required for promotion of tissue remodeling and wound healing processes rather than scar tissue formation in numerous anatomic sites including skeletal muscle (Kuswanto et al., *Immunity* 44, 355-367 (2016); Serrels et al., *Sci. Signal.* 10, 508 (2017)), and cardiovascular systems (Oboki et al., *Proceedings of the National Academy of Sciences* 107, 18581-18586 (2010); Townsend et al., *Journal of Experimental Medicine* 191, 1069-1076 (2000)). This transition is not immunosuppression, but rather a constructive form of immunomodulation that promotes a phenotypic change in local macrophage phenotype (Oliveira et al., *PloS one* 8, e66538 (2013); Reing et al., *Biomaterials* 31, 8626-8633 (2010)). However, it was previously unknown what components of the ECM have this function.

SUMMARY

Methods are disclosed for treating or inhibiting a disorder in a subject having or at risk of having the disorder. In some embodiments the disorder is a) fibrosis of an organ or tissue; b) solid organ transplant rejection; or c) a cardiac disease that is not myocardial infarction or myocardial ischemia. These methods include selecting a subject having or at risk of having the disorder and administering to the subject a therapeutically effective amount of isolated nanovesicles derived from an extracellular matrix, wherein the nanovesicles comprise interleukin (IL)-33 and comprise lysyl oxidase, and wherein the nanovesicles a) do not express CD63 or CD81, or b) are $CD63^{lo}CD81^{lo}$.

In additional embodiments, methods are disclosed for increasing myoblast differentiation. These methods include contacting a myoblast with an effective amount of isolated nanovesicles derived from an extracellular matrix, wherein the nanovesicles comprise interleukin (IL)-33 and comprise lysyl oxidase, and wherein the nanovesicles a) do not express CD63 or CD81, or b) are $CD63^{lo}CD81_{lo}$.

In some non-limiting examples, the nanovesicles maintain expression of CD68 and CD-11b on macrophages in the subject.

The foregoing and other features and advantages will become more apparent from the following detailed description of several embodiments, which proceeds with reference to the accompanying figures.

Figure 1A:
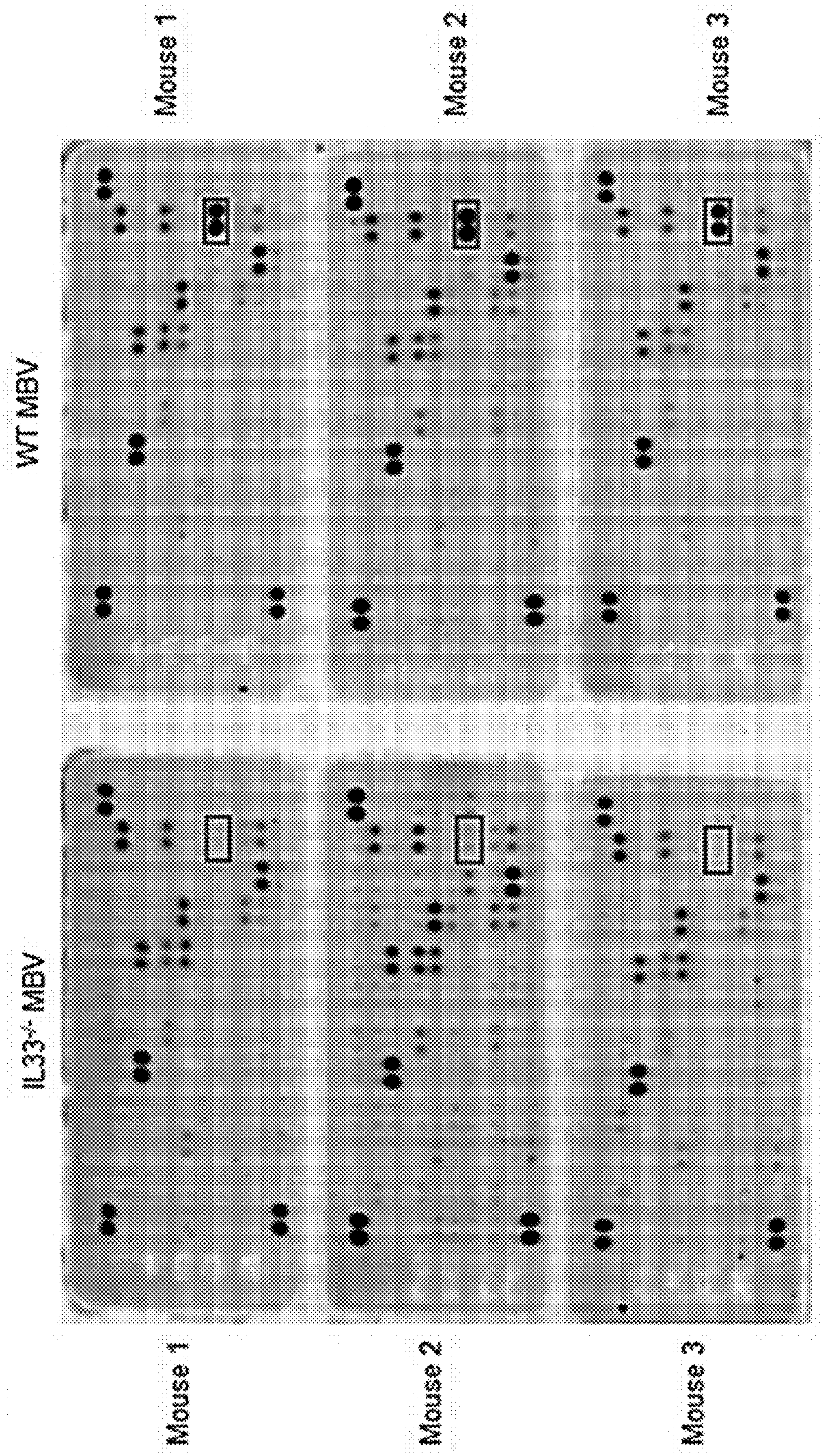
FIGS. 1A-1E: MBV isolated from ECM bioscaffolds contain full-length IL-33. A, Cytokine Array. The cytokine cargo of MBV isolated from decellularized WT mouse intestine (n=3) or decellularized IL-$33^{-/-}$ mouse intestine (n=3) was analyzed using the Mouse XL Cytokine Array Kit from R&D system. The array contains 111 cytokines spotted in duplicate. The boxed areas show the location of IL-33 spots. B, Graphic representation of the quantitation of 15 cytokines with the highest expression levels in MBV isolated from decellularized WT or IL$33^{-/-}$ mouse intestines. C, Transmission electron microscopy imaging of MBV isolated from decellularized WT mouse intestine. Arrows indicate MBV. D, Immunoblot analysis of IL-33 expression levels in MBV isolated from three decellularized WT or three IL$33^{-/-}$ mouse intestines.

E, Immunoblot analysis of IL-33 expression levels in MBV isolated from laboratory produced porcine urinary bladder matrix (UBM), small intestinal submucosa (SIS), dermis, and cardiac muscle ECM and three commercially available biologic scaffolds equivalents: ACELL® MATRISTEM™ (porcine urinary bladder), BD® XENMATRIX™ (porcine dermis), and COOK BIOTECH® BIODESIGN™.

FIGS. 2A-2E: Full-length IL-33 stored in the ECM is protected from proteolytic degradation by incorporation into the lumen of MBV. A, MBV were fractionated by size exclusion chromatography (SEC) with continuous monitoring of eluted fractions by UV absorbance at 280 nm. Thirty 500 μl fractions were collected. In a separate experiment, MBV were first lysed with TRITON® X-100 and then fractioned by SEC. Overlay of the two UV chromatograms shows that intact MBV eluted in the heavier fractions, whereas the molecular components of lysed MBV eluted primarily in the lighter fractions. B, Eluted fractions from chromatographed intact MBV (top panel) or lysed MBV (bottom panel) were pooled as indicated and analyzed by immunoblot for IL-33. C, Pooled fractions 6-8 of chromatographed intact MBV were imaged by transmission electron microscopy. D) Pooled fractions 6-8 of intact MBV were either directly biotinylated to label the MBV surface proteins, or first lysed with TRITON® X-100 and the MBV extract biotinylated to label the luminal and surface proteins. Proteins isolated after streptavidin pull down (SA) and the unbound fraction representing proteins that did not bind to the streptavidin beads (unbound) were analyzed by immunoblot for the presence of IL-33. Arrows indicate MBV. E, Proteinase K protection assay. Pooled fractions 6-8 of chromatographed intact MBV were treated with indicated concentrations of Proteinase K in the absence or presence of TRITON® X-100. Samples were analyzed by immunoblot for IL-33.

FIGS. 3A-3D: MBV containing luminal IL-33 activate a pro-remodeling macrophage phenotype (F4/$80^{+}$1NOS$^{-}$ Arg$^{+}$) via a non-canonical ST2-independent pathway. a,b, Bone Marrow-Derived Macrophages (BMDM) harvested from WT (A) or ST$2^{-/-}$ mice (B) were untreated (control) or treated with the following test articles for 24 hours: IFNγ+LPS, IL-4, IL-33, MBV isolated from decellularized WT mouse intestine (WT MBV), MBV isolated from decellularized IL-$33^{-/-}$ mouse intestine (IL-$33^{-/-}$ MBV), or MBV isolated from porcine small intestinal submucosa (SIS MBV). Cells were immunolabeled with F4/80 (macrophage marker), iNos (MI marker), or Arg1 (M2 marker). C, Quantification of iNOS immunolabeling showed a significant increase in iNOS expression after treatment with IFNy+LPS or MBV isolated from IL-$33^{-/-}$ mice compared to the negative control (IL-4 treated) in both WT and ST$2^{-/-}$ BMDM (** indicates $p<0.01$; * indicates $p<0.05$ compared to negative control, error bars represent SEM, n=3). D, Quantification of arginase immunolabeling shows a significant increase in arginase expression after treatment with IL-4 or MBV isolated from WT mice compared to the negative control (IFNy+LPS) in both WT and ST$2^{-/-}$ BMDM (** indicates $p<0.01$ compared to negative control, error bars represent SEM, n=3).

Figure 4A:
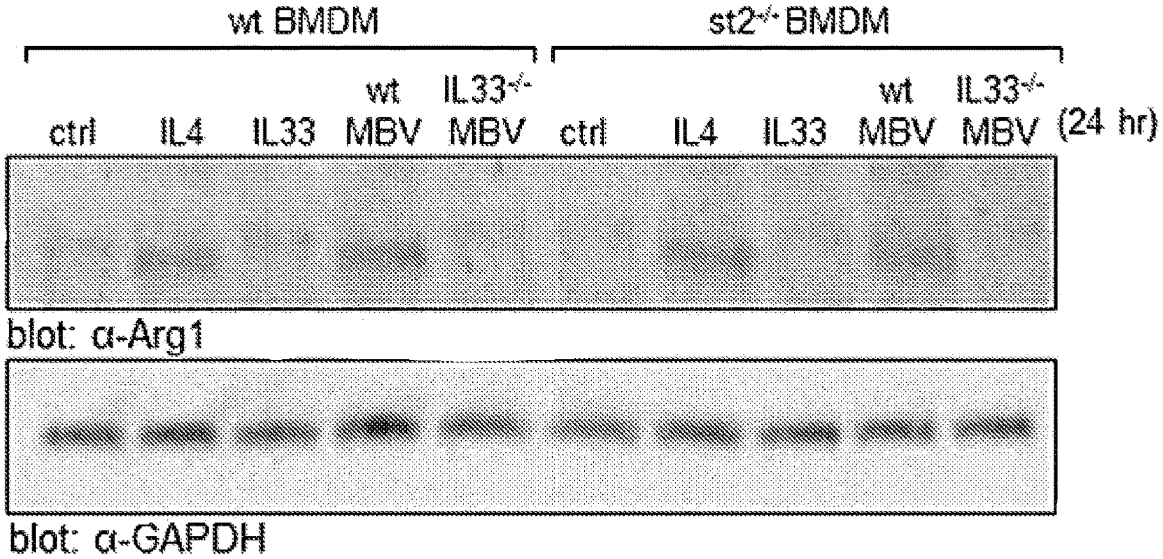
Figure 4B:
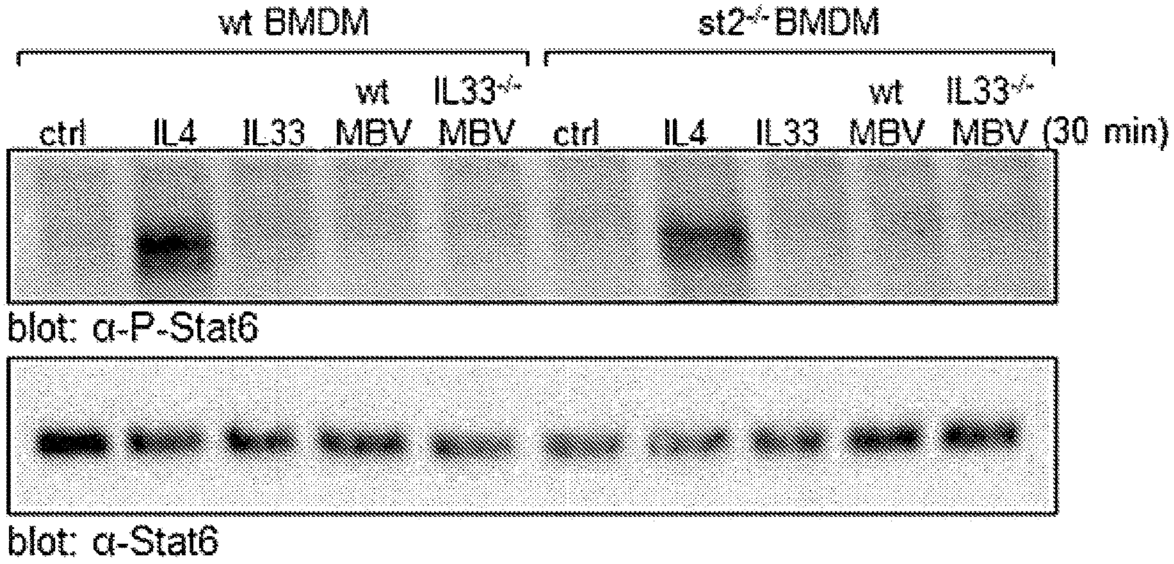

FIGS. 4A-4B: MBV containing IL-33 upregulate Arg1 expression independent of Stat6 phosphorylation. A,B, Bone Marrow-Derived Macrophages (BMDM) harvested from WT or ST$2^{-/-}$ mice were untreated (ctrl), or stimulated for 24 hr (A) or 30 min (B) with IL4, IL-33, MBV isolated from decellularized WT mouse intestine (WT MBV), or MBV isolated from decellularized IL-$33^{-/-}$ mouse intestine (IL-$33^{-/-}$ MBV). Cell lysates were analyzed by immunoblot for Arginase-1 and ST2 expression (A) and phosphorylation of Stat6 (B).

Figure 5A:
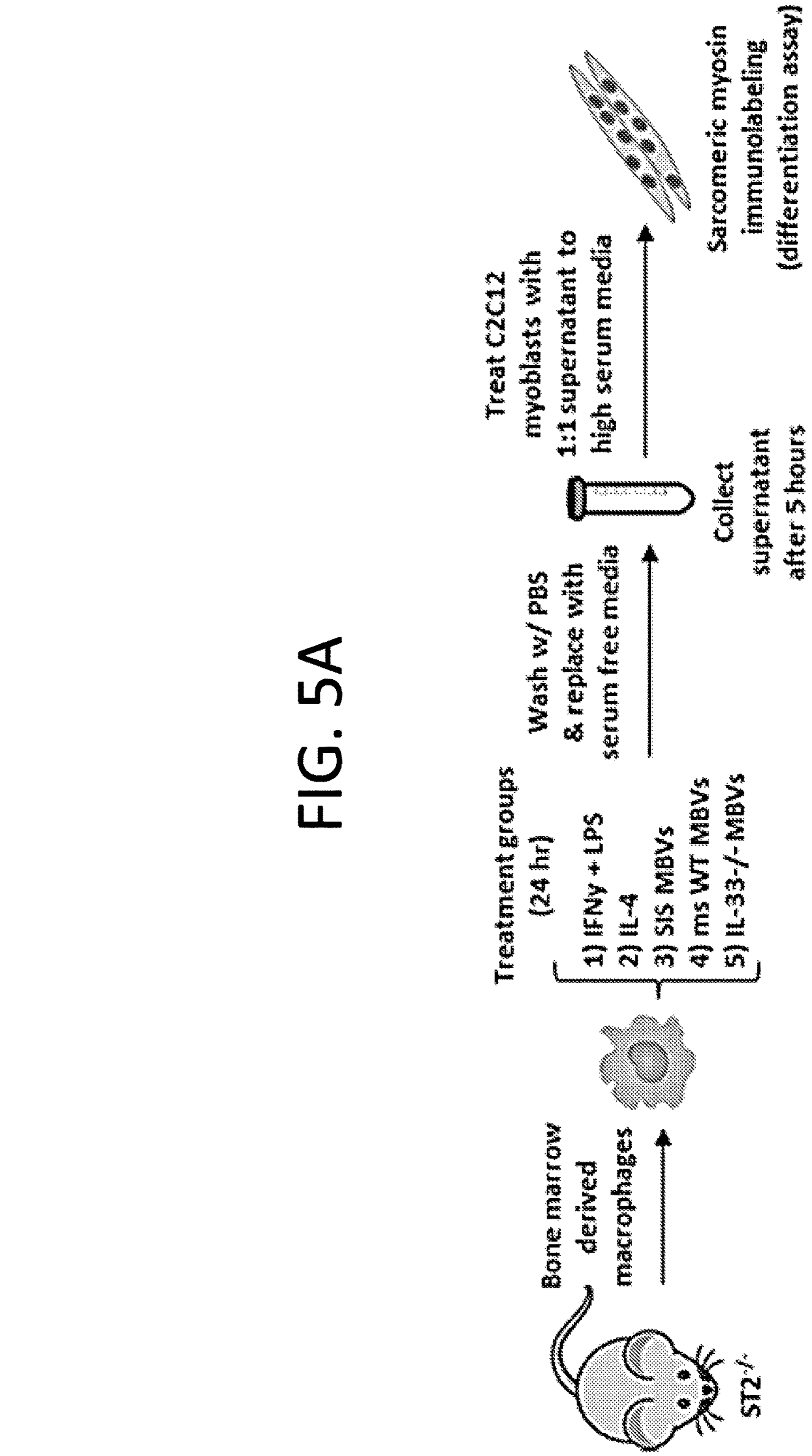
Figure 5B:
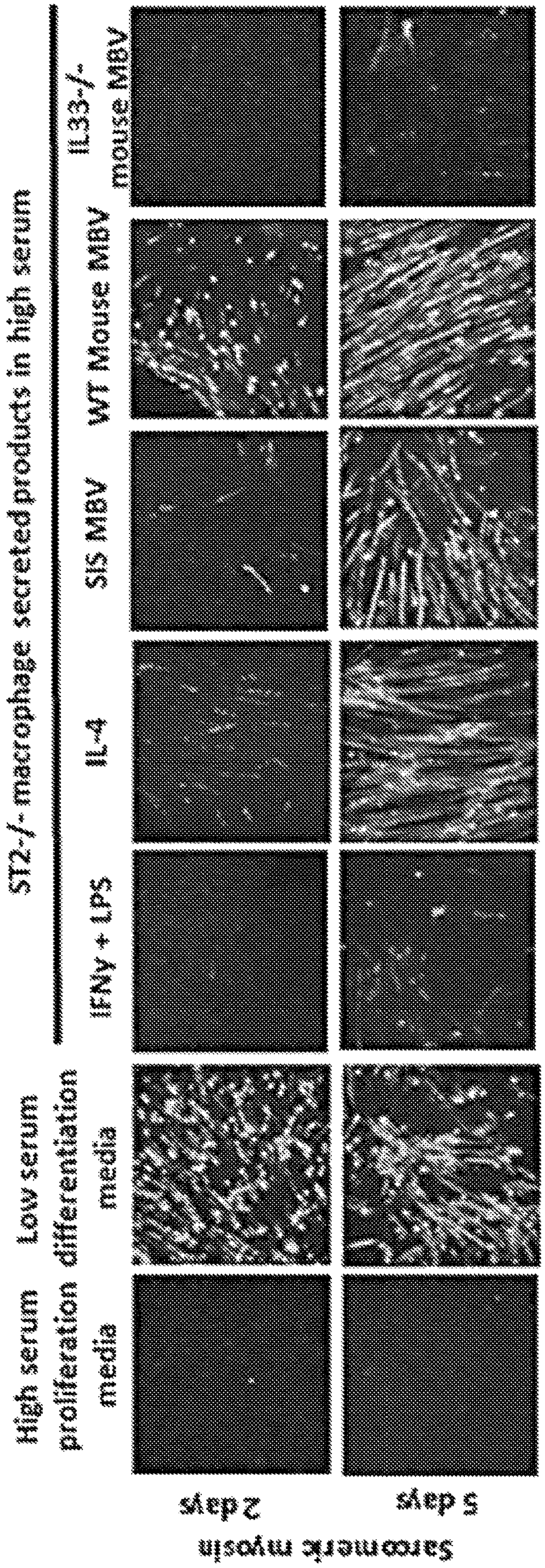

FIGS. 5A-5B: Secreted products of WT MBV-treated macrophages are myogenic for progenitor cells. A, B $C_2C_{12}$ myoblasts were cultured to confluence and treated with proliferation media, differentiation media, or media conditioned by polarized and MBV-treated macrophages. Cells were allowed to differentiate and were immunolabeled for sarcomeric myososin.

FIGS. 6A-6D: The total absence of graft IL-33 results in increased chronic rejection-associated fibrosis and vasculopathy. A-D, IL-$33^{+}$ Bm12 (il$33^{+/+}$ Bm12) or IL-33 deficient Bm12 (il$33^{-/-}$ Bm12) grafts were transplanted into C57BL/6 (B6) IL-33 expressing (WT B6) or deficient (il$33^{-/-}$ B6 recipients (n=6/group). On post-operation day (POD) 90-100, grafts were harvested and evaluated after H&E (A, B), Masson's Trichrome (A, B). Naïve il$33^{-/-}$ Bm12 hearts were stained as controls. The percentage of (C) vascular occlusion and (D) fibrotic area was quantified by NEARCYTE software. "*" indicated the significant differences relative to the il$33^{+/+}$ Bm12 to WT B6 group and P values were generated by one-way analysis of variance (ANOVA), *$P<0.01$, **$P<0.005$.

FIGS. 7A-7D: A total absence of graft IL-33 increased local inflammatory myeloid cells early after heart transplantation. A-D, Wildtype (WT) IL-$33^{+}$ Bm12 and IL-33-deficient knockout (KO) Bm12 grafts were transplanted to WT B6 recipients (n=4-5/group). On post-operation day 3 (POD), graft infiltrating leukocytes were assessed by flow cytometric analysis. Isolated leukocytes from naïve Bm12 mice hearts were included as baseline controls (Control; n=4). A. Representative dot plots from each group depict the frequency of CD11b$^{+}$ CD11c$^{+}$ cells found in the CD45$^{+}$ parent gate. B. Representative dot plots from CD11b$^{+}$ CD11c$^{+}$-gated cells show that increased CD11c$^{+}$ cells are predominantly MHCII$^{hi}$ monocyte-derived dendritic cells (monoDC) and CD11c$^{hi}$ inflammatory macrophages. Arrow indicates the parent population from which gated cell originate. C-D. Representative dot plots from $CD11b^+$ $CD11c^{lo}$-gated cells show that in the absence of IL-33, heart grafts have increased frequency of pro-inflammatory $F4\text{-}80^+$ macrophages, including a $Ly6c^{hi}$ $MHCII^{hi}$ subset. P values were generated by one-way analysis of variance (ANOVA), *P<0.05.

FIGS. 8A-8D: Administration of $IL33^+$ MBV limits the generation of pro-inflammatory infiltrating myeloid cells early after transplantation. A-D, Wildtype (WT) $IL\text{-}33^+$, IL-33-deficient knockout (KO) Bm12 grafts alone, or IL-33 deficient KO Bm12 grafts treated with WT $IL\text{-}33^+$ MBV in Hydrogel (IL33 (Hydrogel)) were transplanted to WT B6 recipients (WT; n=4-6/group). On post-operation day 3 (POD), graft infiltrating leukocytes and splenocytes were assessed by flow cytometric analysis. Leukocytes from naïve Bm12 mice hearts and spleens were also included as baseline controls (Control; n=3-9). Representative dot plots depict frequency (%) monocyte-derived dendritic cell (DC) in the $CD45.2^+$ Lineage $Ly6G^-$ gate (A) and macrophage subsets in the $CD45.2^+$ $Lineage^-$ $Ly6G^-$ $CD11c^-$ $CD11b^+$ gate (B) and of the graft infiltrating and recipient splenocytes. (C-D). Figures depict summary statistics for changes in DC (C) of macrophage subsets (D). P values for data shown in were generated by one-way analysis of variance (ANOVA), *P<0.05, P<0.01, *P<0.005, ****P<0.001.

Figure 9A:
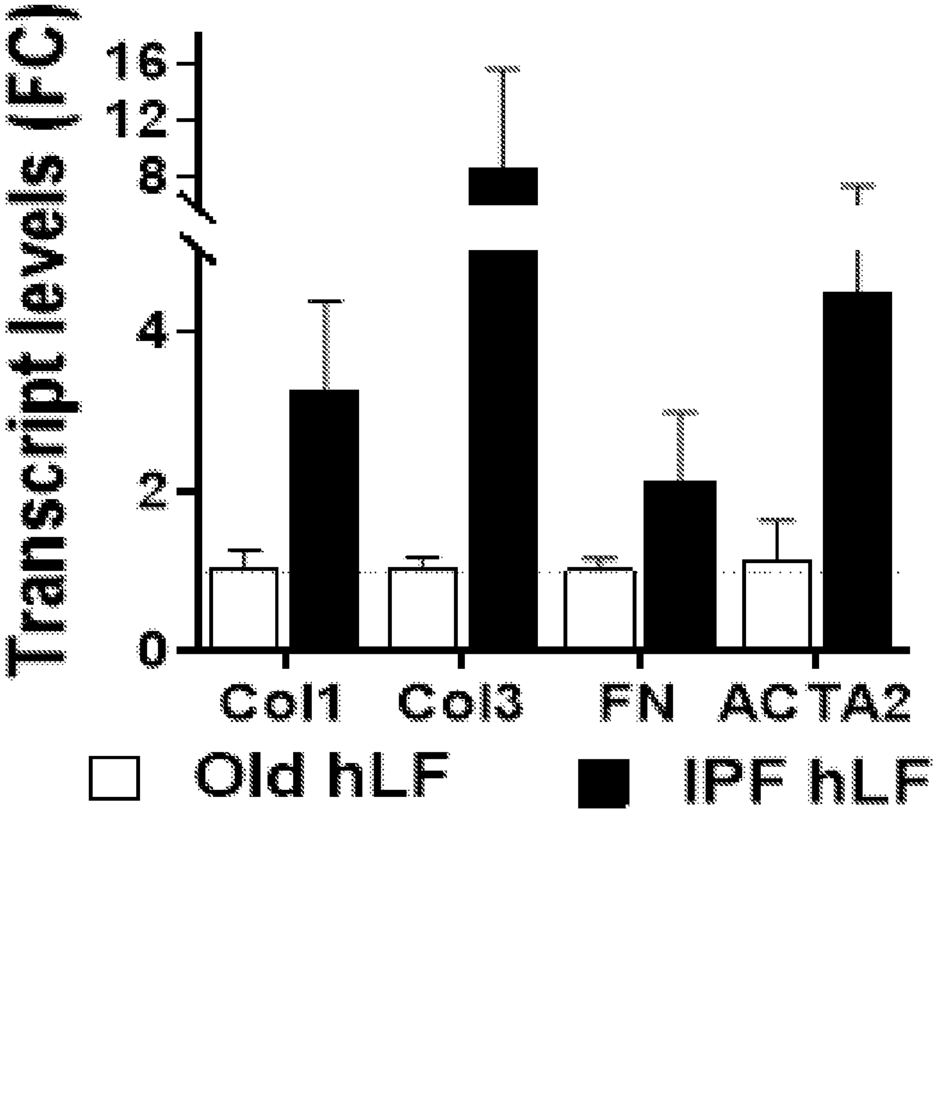
Figure 9B:
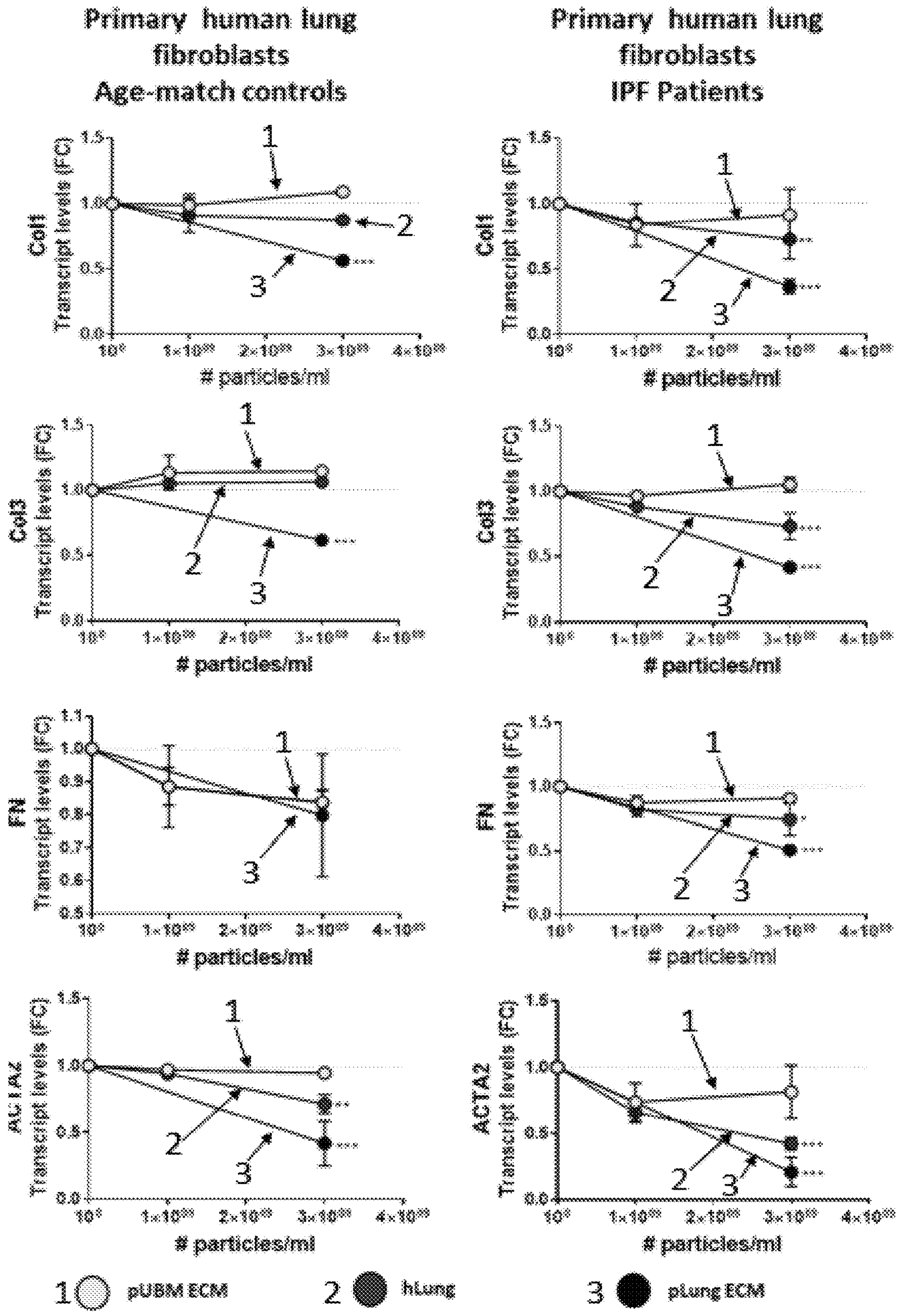

FIGS. 9A-9B. Treatment of Fibrosis. Human lung fibroblasts from explanted lungs from IPF patients and age-matched controls (n=2). (A) Before treatment the levels of expression of Coll, Col3, and ACTA2 were determined. (B) Fibroblasts were treated with matrix-bound nanovesicles (MBV) of different origins: porcine decellularized urinary bladder matrix (pUBM ECM), porcine decellularized lung (pLung) and human lung tissue (hLung); at different doses: $Ix10^9$ and $3\times10^9$ particles/ml. After 48 hours of treatment, the cells were collected and RNA was isolated, for analysis of senescence and fibrotic marker transcript expression by qRT-PCR. * p<0.5, p<0.01, * p<0.00[1].

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing: SEQ ID NOs: 1-3 are miRNA sequences.

DETAILED DESCRIPTION

Degradation of the ECM scaffold material and subsequent release of nanovesicles, also called "matrix bound nanovesicles" or "MBV," that harbor bioactive components, result in activation of a reparative and anti-inflammatory M2 macrophage phenotype. MBV are nanometer-sized, membranous vesicles that are embedded within the collagen network of the ECM and protect biologically active signaling molecules (microRNAs and proteins) from degradation and denaturation. ECM bioscaffolds and their resident MBV can activate macrophages toward a M2-like, pro-remodeling phenotype. It is disclosed herein that these MBVs can be used for targeting infiltrating recipient myeloid cell populations and/or inhibiting allograft fibrotic diseases after solid organ transplant. The disclosed methods can prevent and/or treat allograft fibrotic disease after a solid organ transplant.

It is disclosed herein that MBV are a rich source of extra-nuclear interleukin-33 (IL-33). IL-33 is an IL-1 family member that is typically found in the nucleus of stromal cells and generally regarded as an alarmin, or a self-derived molecule that is released after tissue damage to activate immune cells via the IL-33 receptor, ST2 (Wainwright et al., *Tissue Engineering Part C: Methods* 16, 525-532 (2009)). IL-33 promotes graft survival after heart transplant by stimulating $ST2^+$ regulatory T cells (Treg) (Wainwright et al., *Tissue Engineering Part C: Methods* 16, 525-532 (2009); Böing et al., *Journal of Extracellular Vesicles* 3, 23430 (2014). Intracellular IL-33 protein has been suggested to modulate gene expression through interactions with chromatin or signaling molecules via the IL-33 N-terminus (Jong et al., *Journal of Cellular and Molecular Medicine* 20, 342-350 (2016)). It is disclosed herein that IL-33, stably stored within the ECM and protected from proteolytic cleavage by incorporation into MBV, is a potent mediator of M2 macrophage activation through an uncharacterized, non-canonical ST2-independent pathway.

MBV isolated from $il33^{+/+}$ mouse tissue ECM, but not MBV from $il33^{-/-}$, direct $st2^{-/-}$ macrophage activation toward the reparative, pro-remodeling M2 activation state. This capacity of $IL33^+$ MBV is distinct from the well characterized IL-4/IL-13-mediated M2 macrophage differentiation pathway, as $IL33^+$ MBV generate M2-like macrophages independent of Stat6 phosphorylation. Moreover, in a mouse heart transplant model, transplants deficient in IL-33 displayed a significant increase in early graft infiltration by pro-inflammatory myeloid cells including MI-like macrophages and monocyte-derived DC. Administration of $IL\text{-}33^+$ MBV after transplantation of IL-33-deficient heart transplants profoundly reduced the frequency of pro-inflammatory myeloid cells in the graft. Thus, $IL33^+$ MBV delivery after a solid organ transplant, such as, but not limited to, heart transplant can inhibit and/or prevent myeloid activation during rejection, such as acute or chronic transplant rejection.

Furthermore, MBVs can be used to control local inflammation and support soft tissue repair after injury, or surgical procedures associated with allogeneic solid organ transplantation. The use of MBVs enable IL-33 to induce ST2-independent gene expression in myeloid cells. As a result, this therapy can limit subsequent fibrotic disease by shifting the myeloid compartment at sites of traumatic or ischemic injury away from typical pro-inflammatory and detrimental subsets (MI macrophages, inflammatory monocytes, and inflammatory monocyte-derived dendritic cells) and into a beneficial reparative or regulatory subset (i.e., M2 macrophages and $Ly6c^{lo}$ monocytes). This technology also supports soft tissue and muscle repair at defect sites by similar modifications of local myeloid cells.

Matrix bound nanovesicles (MBVs) are embedded within the fibrillar network of the ECM. These nanoparticles shield their cargo from degradation and denaturation during the ECM-scaffold manufacturing process. Exosomes are microvesicles that previously have been identified almost exclusively in body fluids and cell culture supernatant. It has been demonstrated that MBVs and exosomes are distinct. The MBV differ from other microvesicles, for example, as they are resistant to detergent and/or enzymatic digestion, contain a cluster of different microRNAs, and are enriched in miR-145. MBVs do not have characteristic surface proteins found in other microvesicles such as exosomes. As disclosed herein, MBVs affect cellular survival an modulate a healing response to preserve or to restore neurologic function. It is disclosed that MBVs differentially regulate RGC survival, axon growth, and tissue remodeling.

TERMS

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GENBANK® Accession Nos. referred to herein are the sequences available at least as early as Sep. 16, 2015. All references, patent applications and publications, and GENBANK® Accession numbers cited herein are incorporated by reference. In order to facilitate review of the various embodiments of the disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Biocompatible: Any material, that, when implanted in a mammalian subject, does not provoke an adverse response in the subject. A biocompatible material, when introduced into an individual, is able to perform its' intended function, and is not toxic or injurious to that individual, nor does it induce immunological rejection of the material in the subject.

Cardiac disease or disorder: A disease or disorder that negatively affects the cardiovascular system. The term is also intended to refer to cardiovascular events, such as acute coronary syndrome. myocardial infarction, myocardial ischemia, chronic stable angina pectoris, unstable angina pectoris, angioplasty, stroke, transient ischemic attack, claudication(s) and vascular occlusion(s). Cardiac diseases and disorders. therefore, may include acute coronary syndrome, myocardial infarction, myocardial ischemia, chronic stable angina pectoris, unstable angina pectoris, angioplasty. transient ischemic attack. ischemic-reperfusion injury, claudication(s), vascular occlusion(s), arteriosclerosis, heart failure, chronic heart failure, acute decompensated heart failure. cardiac hypertrophy, cardiac fibrosis, aortic valve, disease, aortic or mitral valve stenosis, cardiomyopathy, atrial fibrillation, heart arrhythmia, and pericardial disease.

Cardiac dysfunction: Any impairment in the heart's pumping function. This includes, for example, impairments in contractility, impairments in ability to relax (sometimes referred to as diastolic dysfunction), abnormal or improper functioning of the heart's valves, diseases of the heart muscle (sometimes referred to as cardiomyopathy), diseases such as angina and myocardial infarction characterized by inadequate blood supply to the heart muscle, infiltrative diseases such as amyloidosis and hemochromatosis, global or regional hypertrophy (such as may occur in some kinds of cardiomyopathy or systemic hypertension), and abnormal communications between chambers of the heart (for example, atrial septal defect). For further discussion, see Braunwald, Heart Disease: a Textbook of Cardiovascular Medicine, 5th edition 1997, WB Saunders Company, Philadelphia PA (hereinafter Braunwald).

Cardiomyopathy: Any disease or dysfunction of the myocardium (heart muscle). These may be inflammatory, metabolic, toxic, infiltrative, fibroplastic, hematological, genetic, or unknown in origin. They are generally classified into three groups based primarily on clinical and pathological characteristics:

(1) dilated cardiomyopathy, a syndrome characterized by cardiac enlargement and impaired systolic function of one or both ventricles;

(2) hypertrophic cardiomyopathy, herein defined as (a) global or regional increase in thickness of either ventricular wall or the interventricular septum, or (b) an increased susceptibility to global or regional increase in thickness of either ventricular wall or the interventricular septum, such as may occur in genetic diseases, hypertension, or heart valve dysfunction; or (3) restrictive and infiltrative cardiomyopathies, a group of diseases in which the predominate clinical feature is usually impaired ability of the heart to relax (diastolic dysfunction), and often characterized by infiltration of the heart muscle with foreign substances such as amyloid fibers, iron, or glycolipids.

See Wynne and Braunwald, The Cardiomyopathies and Myocarditises, Chapter 41 in Braunwald.

Enriched: A process whereby a component of interest, such as a nanovesicle, that is in a mixture has an increased ratio of the amount of that component to the amount of other undesired components in that mixture after the enriching process as compared to before the enriching process.

Extracellular matrix (ECM): A complex mixture of structural and functional biomolecules and/or biomacromolecules including, but not limited to, structural proteins, specialized proteins, proteoglycans, glycosaminoglycans, and growth factors that surround and support cells within tissues and, unless otherwise indicated, is acellular. ECM preparations can be considered to be "decellularized" or "acellular", meaning the cells have been removed from the source tissue through processes described herein and known in the art. By "ECM-derived material," such as an "ECM-derived nanovesicle," "Matrix bound nanovesicle," "MBV" or "nanovesicle derived from an ECM" it is a nanovesicle that is prepared from a natural ECM or from an in vitro source wherein the ECM is produced by cultured cells. ECM-derived nanovesicles are defined below.

Fibrosis-related disease or fibrotic disease: A disease or disorder in which fibrosis is a primary pathologic basis, result or symptom. Fibrosis, or scarring, is defined by excessive accumulation of fibrous connective tissue (components of the extracellular matrix (ECM) such as collagen and fibronectin) in and around inflamed or damaged tissue, which can lead to permanent scarring, organ malfunction and, ultimately, death. Normal tissue repair can evolve into a progressively irreversible fibrotic response if the tissue injury is severe or repetitive or if the wound-healing response itself becomes dysregulated. Fibrosis-related diseases include, for example, skin pathologic scarring, such as keloid and hypertrophic scarring; cirrhosis, such as cirrhosis of the liver or gallbladder; cardiac fibrosis; liver fibrosis; kidney fibrosis; pulmonary fibrosis; bone-marrow fibrosis; rheumatic heart disease; sclerosing peritonitis; glomerulosclerosis, scleroderma, mediastinal fibrosis, retroperitoneal fibrosis, and fibrosis of the tendons and cartilage. Fibrosis can be the result of a number of factors. Examples include, to name just a few, inherited genetic disorders; persistent infections; recurrent exposure to toxins, irritants or smoke;

chronic autoimmune inflammation; minor human leukocyte antigen mismatches in transplants; myocardial infarction; high serum cholesterol; obesity; and poorly controlled diabetes and hypertension Fibrosis can also be induced by tissue injury. However, regardless of the initiating events, a feature common to all fibrotic diseases is the activation of ECM-producing myofibroblasts, which are the key mediators of fibrotic tissue remodeling. As used herein, "tissue injury" refers to any damage of or strain placed on a tissue such that there is a change that occurs in or to the tissue. Tissue injuries include cardiac tissue injury or lung tissue injury. One of ordinary skill in the art will readily recognize that cardiac tissue injury can result from cardiac strain or cardiac overload. Generally, the subjects in need of the methods and compositions provided herein, therefore, include those in which there is increased cardiac strain, such that there is an increased risk of developing a cardiac disease or disorder or a fibrosis-related disease, such as a cardiac fibrosis. Conditions that can lead to cardiac fibrosis include but are not limited to hypertrophic cardiomyopathy, sarcoidosis, myocarditis, chronic renal insufficiency, toxic cardiomyopathies, surgery-mediated ischemia reperfusion injury, acute and chronic organ rejection, aging, chronic hypertension, non-ischemic dilated cardiomyopathyarrhythmias, atherosclerosis, HIV-associated cardiovascular disease, pulmonary hypertension. Conditions that can lead to pulmonary fibrosis include but are not limited to autoimmune diseases such as rheumatoid arthritis and Sjogren's syndrome, gastroesophageal reflux disease (GERD), sarcoidosis, cigarette smoking, asbestos or silica exposure, exposure to rock and metal dusts, viral infections, exposure to radiation, and certain medications.

Graft-Versus-Host Disease (GVHD): A common and serious complication of bone marrow or other tissue transplantation wherein there is a reaction of donated immunologically competent lymphocytes against a transplant recipient's own tissue. GVHD is a possible complication of any transplant that uses or contains stem cells from either a related or an unrelated donor.

There are two kinds of GVHD, acute and chronic. Acute GVHD appears within the first three months following transplantation. Signs of acute GVHD include a reddish skin rash on the hands and feet that may spread and become more severe, with peeling or blistering skin. Acute GVHD can also affect the stomach and intestines, in which case cramping, nausea, and diarrhea are present. Yellowing of the skin and eyes (jaundice) indicates that acute GVHD has affected the liver. Chronic GVHD is ranked based on its severity: stage/grade 1 is mild; stage/grade 4 is severe. Chronic GVHD develops three months or later following transplantation. The symptoms of chronic GVHD are similar to those of acute GVHD, but in addition, chronic GVHD may also affect the mucous glands in the eyes, salivary glands in the mouth, and glands that lubricate the stomach lining and intestines.

Heart: the muscular organ of an animal that circulates blood. In mammals, the heart is comprised of four chambers: right atrium, right ventricle, left atrium, left ventricle. The right atrium and left atrium are separated from each other by an interatrial septum, and the right ventricle and left ventricle are separated from each other by an interventricular septum. The right atrium and right ventricle are separated from each other by the tricuspid valve. The left atrium and left ventricle are separated from each other by the mitral valve.

The walls of the heart's four chambers are comprised of working muscle, or myocardium, and connective tissue. Myocardium is comprised of myocardial cells, which may also be referred to herein as cardiac cells, cardiac myocytes, cardiomyocytes and/or cardiac fibers. Myocardial cells may be isolated from a subject and grown in vitro. The inner layer of myocardium closest to the cavity is termed endocardium, and the outer layer of myocardium is termed epicardium. The left ventricular cavity is bounded in part by the interventricular septum and the left ventricular free wall. The left ventricular free wall is sometimes divided into regions, such as anterior wall, posterior wall and lateral wall; or apex (the tip of the left ventricle, furthest from the atria) and base (part of the left ventricle closest to the atria). Apical and basal are adjectives that refer to the corresponding region of the heart.

In operation, the heart's primary role is to pump sufficient oxygenated blood to meet the metabolic needs of the tissues and cells in a subject. The heart accomplishes this task in a rhythmic and highly coordinated cycle of contraction and relaxation referred to as the cardiac cycle. For simplicity, the cardiac cycle may be divided into two broad categories: ventricular systole, the phase of the cardiac cycle where the ventricles contract; and ventricular diastole, the phase of the cardiac cycle where the ventricles relax. See Opie, Chapter 12 in Braunwald for a detailed discussion. Used herein, the terms systole and diastole are intended to refer to ventricular systole and diastole, unless the context clearly dictates otherwise.

In normal circulation during health, the right atrium receives substantially deoxygenated blood from the body via the veins. In diastole, the right atrium contracts and blood flows into the right ventricle through the tricuspid valve. The right ventricle fills with blood, and then contracts (systole). The force of systole closes the tricuspid valve and forces blood through the pulmonic valve into the pulmonary artery. The blood then goes to the lungs, where it releases carbon dioxide and takes up oxygen. The oxygenated blood returns to the heart via pulmonary veins, and enters the left atrium. In diastole, the left atrium contracts and blood flows into the left ventricle through the mitral valve. The left ventricle fills with blood and then contracts, substantially simultaneously with right ventricular contraction. The force of contraction closes the mitral valve and forces blood through the aortic valve into the aorta. From the aorta, oxygenated blood circulates to all tissues of the body where it delivers oxygen to the cells. Deoxygenated blood then returns via the veins to the right atrium.

In the cavity of left ventricle, there are two large, essentially cone-shaped extensions of the ventricular myocardium known as the anterior and posterior papillary muscles. These connect to the ventricular surface of the mitral valve via threadlike extensions termed chordae tendiniae or chordae. One important role for the papillary muscles and chordae is to ensure that the mitral valve stays closed during ventricular systole. Another important role is to add to the force of cardiac contraction. Similarly, the right ventricle has papillary muscles and chordae which tether the tricuspid valve and add to the force of contraction.

Due to inherited or acquired disease processes and/or normal aging, the heart muscle may develop dysfunction of either systole or diastole, or both. Dysfunction of systole is referred to as systolic dysfunction. Dysfunction of diastole is referred to as diastolic dysfunction. See Opie Chapter 12, and Colucci et al., Chapter 13 in Braunwald for a detailed discussion.

Due to inherited or acquired disease processes and/or normal aging, one or more of the heart valves may develop dysfunction. Valvular dysfunction generally falls into two broad categories: stenosis, defined herein as incomplete opening of the valve during a time of the cardiac cycle when a normally operating valve is substantially open; and insufficiency, defined herein as incomplete closing of the valve during a time of the cardiac cycle when a normally operating valve is substantially closed. Valvular dysfunction also includes a condition known as mitral valve prolapse, wherein the mitral valve leaflets prolapse backward into the left atrium during ventricular systole. The condition may be associated with mild, moderate, or severe insufficiency of the mitral valve.

Valvular stenosis is typically characterized by a pressure gradient across the valve when the valve is open. Valvular insufficiency is typically characterized by retrograde ("backward") flow when the valve is closed. For example, mitral stenosis is characterized by a pressure gradient across the mitral valve near the end of ventricular diastole (as a typical example of moderate mitral stenosis, 5 mm Hg diastolic pressure in the left ventricle, 20 mm Hg diastolic pressure in the left atrium, for a pressure gradient of 15 mm Hg). As another example, mitral insufficiency is characterized by "backward" flow of blood from the left ventricle into the left atrium during ventricular systole.

Heart failure: The inability of the heart to supply sufficient oxygenated blood to meet the metabolic needs of the tissues and cells in a subject. This may be accompanied by circulatory congestion, such as congestion in the pulmonary or systemic veins. As used herein, the term heart failure encompasses heart failure from any cause, and is intended herein to encompass terms such as "congestive heart failure," "forward heart failure," "backward heart failure," "high output heart failure," "low output heart failure," and the like. See Chapters 13-17 in Braunwald for a detailed discussion.

Inhibiting: Reducing, such as a disease or disorder. The inhibition of a disease or disorder can decrease one or more signs or symptoms of the disease or disorder.

Interleukin (IL)-33: A member of the IL-1 superfamily of cytokines, a determination based in part on the molecules β-trefoil structure, a conserved structure type described in other IL-1 cytokines, including IL-1α, IL-1β, IL-IRa and IL-18. In this structure, the 12 β-strands of the β-trefoil are arranged in three pseudo repeats of four β-strand units, of which the first and last β-strands are antiparallel staves in a six-stranded β-barrel, while the second and third β-strands of each repeat form a β-hairpin sitting atop the β-barrel. IL-33 binds to a high-affinity receptor family member ST2. IL-33 induces helper T cells, mast cells, eosinophils and basophils to produce type 2 cytokines. Exemplary amino acid sequences for human IL-33 are provide in GENBANK® Accession Nos. NP_001186569.1, NP_001186570.1, NP_001300973.1, NP_001300974.1, and NP_001300975.1, all incorporated herein by reference as available Apr. 5, 2018.

Isolated: An "isolated" biological component (such as a nucleic acid, protein cell, or nanovesicle) has been substantially separated or purified away from other biological components in the cell of the organism or the ECM, in which the component naturally occurs. Nucleic acids and proteins that have been "isolated" include nucleic acids and proteins purified by standard purification methods. Nanovesicles that have been isolated are removed from the fibrous materials of the ECM. The term also embraces nucleic acids and proteins prepared by recombinant expression in a host cell as well as chemically synthesized nucleic acids.

Lysyl oxidase (Lox): A copper-dependent enzyme that catalyzes formation of aldehydes from lysine residues in collagen and elastin precursors. These aldehydes are highly reactive, and undergo spontaneous chemical reactions with other lysyl oxidase-derived aldehyde residues, or with unmodified lysine residues. In vivo, this results in cross-linking of collagen and elastin, which plays a role in stabilization of collagen fibrils and for the integrity and elasticity of mature elastin. Complex cross-links are formed in collagen (pyridinolines derived from three lysine residues) and in elastin (desmosines derived from four lysine residues) that differ in structure. The genes encoding Lox enzymes have been cloned from a variety of organisms (Hamalainen et al., Genomics 11:508, 1991; Trackman et al., Biochemistry 29:4863, 1990; incorporated herein by reference). Residues 153-417 and residues 201-417 of the sequence of human lysyl oxidase have been shown to be important for catalytic function. There are four Lox-like isoforms, called LoxL1, LoxL2, LoxL3 and LoxL4.

Macrophage: A type of white blood cell that phagocytoses and degrades cellular debris, foreign substances, microbes, and cancer cells. In addition to their role in phagocytosis, these cells play an important role in development, tissue maintenance and repair, and in both innate and adaptive immunity in that they recruit and influence other cells including immune cells such as lymphocytes. Macrophages can exist in many phenotypes, including phenotypes that have been referred to as M1 and M2. Macrophages that perform primarily pro-inflammatory functions are called M1 macrophages (CD86+/CD68+), whereas macrophages that decrease inflammation and encourage and regulate tissue repair are called M2 macrophages (CD206+/CD68+). The markers that identify the various phenotypes of macrophages vary among species. It should be noted that macrophage phenotype is represented by a spectrum that ranges between the extremes of M1 and M2. F4/80 (encoded by the adhesion G protein coupled receptor El (ADGRE) gene) is a macrophage marker, see GENBANK® Accession No. NP_001243181.1, Apr. 6, 2018 and NP_001965, Mar. 5, 2018, both incorporated herein by reference. It is disclosed herein that nanovesicles maintain expression of CD68 and CD-11b on macrophages in the subject.

MicroRNA: A small non-coding RNA that is about 17 to about 25 nucleotide bases in length, that post-transcriptionally regulates gene expression by typically repressing target mRNA translation. A miRNA can function as negative regulators, such that greater amounts of a specific miRNA will correlates with lower levels of target gene expression. There are three forms of miRNAs, primary miRNAs (pri-miRNAs), premature miRNAs (pre-miRNAs), and mature miRNAs. Primary miRNAs (pri-miRNAs) are expressed as stem-loop structured transcripts of about a few hundred bases to over 1 kb. The pri-miRNA transcripts are cleaved in the nucleus by an RNase II endonuclease called Drosha that cleaves both strands of the stem near the base of the stem loop. Drosha cleaves the RNA duplex with staggered cuts, leaving a 5' phosphate and 2 nucleotide overhang at the 3' end. The cleavage product, the premature miRNA (pre-miRNA) is about 60 to about 110 nucleotides long with a hairpin structure formed in a fold-back manner. Pre-miRNA is transported from the nucleus to the cytoplasm by Ran-GTP and Exportin-5. Pre-miRNAs are processed further in the cytoplasm by another RNase II endonuclease called Dicer. Dicer recognizes the 5' phosphate and 3' overhang, and cleaves the loop off at the stem-loop junction to form miRNA duplexes. The miRNA duplex binds to the RNA-induced silencing complex (RISC), where the antisense strand is preferentially degraded and the sense strand mature miRNA directs RISC to its target site. It is the mature miRNA that is the biologically active form of the miRNA and is about 17 to about 25 nucleotides in length.

Myoblast: A muscle cell that has not fused with other myoblasts to form a myofibril and has not fused with an existing myofibril.

Nanoveside: An extracellular vesicle that is a nanoparticle of about 10 to about 1,000 nm in diameter. Nanovesicles are lipid membrane bound particles that carry biologically active signaling molecules (e.g. microRNAs, proteins) among other molecules. Generally, the nanovesicle is limited by a lipid bilayer, and the biological molecules are enclosed and/or can be embedded in the bilayer. Thus, a nanovesicle includes a lumen surrounded by plasma membrane. The different types of vesicles can be distinguished based on diameter, subcellular origin, density, shape, sedimentation rate, lipid composition, protein markers, nucleic acid content and origin, such as from the extracellular matrix or secreted. A nanovesicle can be identified by its origin, such as a matrix bound nanovesicle from an ECM (see above), protein content and/or the miR content.

An "exosome" is a membranous vesicle which is secreted by a cell, and ranges in diameter from 10 to 150 nm. Generally, late endosomes or multivesicular bodies contain intralumenal vesicles which are formed by the inward budding and scission of vesicles from the limited endosomal membrane into these enclosed vesicles. These intralumenal vesicles are then released from the multivesicular body lumen into the extracellular environment, typically into a body fluid such as blood, cerebrospinal fluid or saliva, during exocytosis upon fusion with the plasma membrane. An exosome is created intracellularly when a segment of membrane invaginates and is endocytosed. The internalized segments which are broken into smaller vesicles and ultimately expelled from the cell contain proteins and RNA molecules such as mRNA and miRNA. Plasma-derived exosomes largely lack ribosomal RNA. Extra-cellular matrix derived exosomes include specific miRNA and protein components, and have been shown to be present in virtually every body fluid such as blood, urine, saliva, semen, and cerebrospinal fluid. Exosomes can express CD11c and CD63, and thus can be $CD11c^+$ and $CD63^+$. Exosomes do not have high levels of lys1 oxidase on their surface.

A "nanovesicle derived from an ECM" "matrix bound nanovesicle," "MBV" or an "ECM-derived nanovesicle" all refer to the same membrane bound particles, ranging in size from 10 nm-1000 nm, present in the extracellular matrix, which contain biologically active signaling molecules such as protein, lipids, nucleic acid, growth factors and cytokines that influence cell behavior. The terms are interchangeable, and refer to the same vesicles. These MBVs are embedded within, and bound to, the ECM and are not just attached to the surface. These MBVs are resistant harsh isolation conditions, such as freeze thawing and digestion with proteases such as pepsin, elastase, hyaluronidase, proteinase K, and collagenase, and digestion with detergents. Generally, these MBVs are enriched for miR-145 and optionally miR-181, miR-143, and miR-125, amongst others. These MBVs do not express CD63 or CD81, or express barely detectable levels of these markers ($CD63^{lo}CD81_{lo}$). The MBVs contain lys1 oxidase (Lox) o their surface. The ECM can be an ECM from a tissue, can be produced from cells in culture, or can be purchased from a commercial source. MBVs are distinct from exosomes.

Organ rejection or transplant rejection: Functional and structural deterioration of an organ due to an active immune response expressed by the recipient, and independent of non-immunologic causes of organ dysfunction.

Pharmaceutically acceptable carriers: The pharmaceutically acceptable carriers useful in this invention are conventional. *Remington's Pharmaceutical Sciences*, by E. W. Martin, Mack Publishing Co., Easton, PA, 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell. "Incubating" includes a sufficient amount of time for a drug to interact with a cell. "Contacting" includes incubating an agent, such as an exosome, a miRNA, or nucleic acid encoding a miRNA, in solid or in liquid form with a cell.

Polynucleotide: A nucleic acid sequence (such as a linear sequence) of any length. Therefore, a polynucleotide includes oligonucleotides, and also gene sequences found in chromosomes. An "oligonucleotide" is a plurality of joined nucleotides joined by native phosphodiester bonds. An oligonucleotide is a polynucleotide of between 6 and 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Purified: The term "purified" does not require absolute purity; rather, it is intended as a relative term. Thus, for example, a purified nucleic acid molecule preparation is one in which the nucleic referred to is more pure than the nucleic in its natural environment within a cell. For example, a preparation of a nucleic acid is purified such that the nucleic acid represents at least 50% of the total protein content of the preparation. Similarly, a purified exosome preparation is one in which the exosome is more pure than in an environment including cells, wherein there are microvesicles and exosomes. A purified population of nucleic acids or exosomes is greater than about 90%, 91%, 92%, 93%, 94%, 95%, 96%, 97%, 98%, 99% or 100% pure, or free other nucleic acids or cellular components, respectively.

Preventing or treating a disease: "Preventing" a disease refers to inhibiting the development of a disease, for example in a person who is known to have a predisposition to a disease such as glaucoma. An example of a person with a known predisposition is someone with a history of a disease in the family, or who has been exposed to factors that predispose the subject to a condition. "Treatment" refers to a therapeutic intervention that ameliorates a sign or symptom of a disease or pathological condition after it has begun to develop.

ST2: A member of the interleukin 1 receptor family. ST2 is also known as ILR1RL1, and is also a member of the Toll-like receptor superfamily based on the function of its intracellular TIR domain, but its extracellular region is composed of immunoglobulin domains.

The ST2 protein has two isoforms and is directly implicated in the progression of cardiac disease: a soluble form (referred to as soluble ST2 or sST2) and a membrane-bound receptor form (referred to as the ST2 receptor or ST2L). When the myocardium is stretched, the ST2 gene is upregulated, increasing the concentration of circulating soluble ST2. The ligand for ST2 is IL-33.

Binding of IL-33 to the ST2 receptor, in response to cardiac disease or injury, such as an ischemic event, elicits a cardioprotective effect resulting in preserved cardiac function. This cardioprotective IL-33 signal is counterbalanced by the level of soluble ST2, which binds IL-33 and makes it unavailable to the ST2 receptor for cardioprotective signaling. As a result, the heart is subjected to greater stress in the presence of high levels of soluble ST2.

Subject: Human and non-human animals, including all vertebrates, such as mammals and non-mammals, such as non-human primates, mice, rabbits, sheep, dogs, cats, horses, cows, chickens, amphibians, and reptiles. In many embodiments of the described methods, the subject is a human.

Therapeutically effective amount: A quantity of a specific substance, such as an MBV, sufficient to achieve a desired effect in a subject being treated. When administered to a subject, a dosage will generally be used that will achieve target tissue concentrations (for example, in bone) that has been shown to achieve a desired in vitro effect.

Transplantation: The transfer of a tissue, cells, or an organ, or a portion thereof, from one subject to another subject, from one subject to another part of the same subject, or from one subject to the same part of the same subject. In one embodiment, transplantation of a solid organ, such as a heart, kidney, skin, pancreas or lung, involves removal of the solid organ from one subject, and introduction of the solid organ into another subject.

An allogeneic transplant or a heterologous transplant is transplantation from one individual to another, wherein the individuals have genes at one or more loci that are not identical in sequence in the two individuals. An allogeneic transplant can occur between two individuals of the same species, who differ genetically, or between individuals of two different species. An autologous transplant is transplantation of a tissue, cells, or a portion thereof from one location to another in the same individual, or transplantation of a tissue or a portion thereof from one individual to another, wherein the two individuals are genetically identical.

"Transplanting" is the placement of a biocompatible substrate into a subject in need thereof.

Treating, Treatment, and Therapy: Any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or improving vision. The treatment may be assessed by objective or subjective parameters; including the results of a physical examination, neurological examination, or psychiatric evaluations.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. Unless otherwise specified, "about" is within five percent. In case of conflict, the present specification, including explanations of terms, will control. In addition, the materials, methods, and examples are illustrative only and not intended to be limiting.

Nanovesicles Derived from an Extracellular Matrix (ECM)

Nanovesicles derived from ECM (also called matrix bound nanovesicles, MBVs) are disclosed in PCT Publication No. WO 2017/151862, which is incorporated herein by reference. It is disclosed that nanovesicles are embedded in the extracellular matrix. These MBVs can be isolated and are biologically active. Thus, these MBVs can be used for therapeutic purposes, either alone or with another ECM. These MBVs can be used in biological scaffolds, either alone or with another ECM. It is disclosed herein that MBVs contain IL-33, and are of use to treat cardiac disease and disorders, and fibrotic diseases and disorders. In some non-limiting examples, the nanovesicles maintain expression of CD68 and CD-11b on macrophages in the subject.

An extracellular matrix is a complex mixture of structural and functional biomolecules and/or biomacromolecules including, but not limited to, structural proteins, specialized proteins, proteoglycans, glycosaminoglycans, and growth factors that surround and support cells within mammalian tissues and, unless otherwise indicated, is acellular. Generally, the disclosed MBVs are embedded in any type of extracellular matrix (ECM), and can be isolated from this location. Thus, MBVs are not detachably present on the surface of the ECM, and are not exosomes.

Extracellular matrices are disclosed, for example and without limitation, in U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666; each of which is incorporated by reference in its entirety). However, an ECM can be produced from any tissue, or from any in vitro source wherein the ECM is produced by cultured cells and comprises one or more polymeric components (constituents) of native ECM. ECM preparations can be considered to be "decellularized" or "acellular", meaning the cells have been removed from the source tissue or culture.

In some embodiments, the ECM is isolated from a vertebrate animal, for example, from a mammalian vertebrate animal including, but not limited to, human, monkey, pig, cow, sheep, etc. The ECM may be derived from any organ or tissue, including without limitation, urinary bladder, intestine, liver, heart, esophagus, spleen, stomach and dermis. In specific non-limiting examples, the extracellular matrix is isolated from esophageal tissue, urinary bladder, small intestinal submucosa, dermis, umbilical cord, pericardium, cardiac tissue, or skeletal muscle. The ECM can comprise any portion or tissue obtained from an organ, including, for example and without limitation, submucosa, epithelial basement membrane, tunica propria, etc. In one non-limiting embodiment, the ECM is isolated from urinary bladder. ECM can be produced from tumor tissue.

The ECM may or may not include the basement membrane. In another non-limiting embodiment, the ECM includes at least a portion of the basement membrane. The ECM material may or may not retain some of the cellular elements that comprised the original tissue such as capillary endothelial cells or fibrocytes. In some embodiments, the ECM contains both a basement membrane surface and a non-basement membrane surface.

In one non-limiting embodiment, the ECM is harvested from porcine urinary bladders (also known as urinary bladder matrix or UBM). Briefly, the ECM is prepared by removing the urinary bladder tissue from a mammal, such as a pig, and trimming residual external connective tissues, including adipose tissue. All residual urine is removed by repeated washes with tap water. The tissue is delaminated by first soaking the tissue in a deepithelializing solution, for example and without limitation, hypertonic saline (e.g. 1.0 N saline), for periods of time ranging from ten minutes to four hours. Exposure to hypertonic saline solution removes the epithelial cells from the underlying basement membrane. Optionally, a calcium chelating agent may be added to the saline solution. The tissue remaining after the initial delamination procedure includes the epithelial basement membrane and tissue layers abluminal to the epithelial basement membrane. The relatively fragile epithelial basement membrane is invariably damaged and removed by any mechanical abrasion on the luminal surface. This tissue is next subjected to further treatment to remove most of the abluminal tissues but maintain the epithelial basement membrane and the tunica propria. The outer serosal, adventitial, tunica muscularis mucosa, tunica submucosa and most of the muscularis mucosa are removed from the remaining deepithelialized tissue by mechanical abrasion or by a combination of enzymatic treatment (e.g., using trypsin or collagenase) followed by hydration, and abrasion. Mechanical removal of these tissues is accomplished by removal of mesenteric tissues with, for example and without limitation, Adson-Brown forceps and Metzenbaum scissors and wiping away the tunica muscularis and tunica submucosa using a longitudinal wiping motion with a scalpel handle or other rigid object wrapped in moistened gauze. Automated robotic procedures involving cutting blades, lasers and other methods of tissue separation are also contemplated. After these tissues are removed, the resulting ECM consists mainly of epithelial basement membrane and subjacent tunica propria.

In another embodiment, the ECM is prepared by abrading porcine bladder tissue to remove the outer layers including both the tunica serosa and the tunica muscularis using a longitudinal wiping motion with a scalpel handle and moistened gauze. Following eversion of the tissue segment, the luminal portion of the tunica mucosa is delaminated from the underlying tissue using the same wiping motion. Care is taken to prevent perforation of the submucosa. After these tissues are removed, the resulting ECM consists mainly of the tunica submucosa (see FIG. 2 of U.S. Pat. No. 9,277,999, which is incorporated herein by reference).

ECM can also be prepared as a powder. Such powder can be made according the method of Gilbert et al., Biomaterials 26 (2005) 1431-1435, herein incorporated by reference in its entirety. For example, UBM sheets can be lyophilized and then chopped into small sheets for immersion in liquid nitrogen. The snap frozen material can then be comminuted so that particles are small enough to be placed in a rotary knife mill, where the ECM is powdered. Similarly, by precipitating NaCl within the ECM tissue the material will fracture into uniformly sized particles, which can be snap frozen, lyophilized, and powdered.

In one non-limiting embodiment, the ECM is derived from small intestinal submucosa or SIS. Commercially available preparations include, but are not limited to, SURGISIS™, SURGISIS-ES™, STRATASIS™, and STRATASIS-ES™ (Cook Urological Inc.; Indianapolis, Ind.) and GRAFTPATCH™ (Organogenesis Inc.; Canton Mass.). In another non-limiting embodiment, the ECM is derived from dermis. Commercially available preparations include, but are not limited to PELVICOL™ (sold as PERMACOL™ in Europe; Bard, Covington, Ga.), REPLIFORM™ (Microvasive; Boston, Mass.) and ALLODERM™ (LifeCell; Branchburg, N.J.). In another embodiment, the ECM is derived from urinary bladder. Commercially available preparations include, but are not limited to UBM (ACell Corporation; Jessup, Md.).

MBVs can be derived from (released from) an extracellular matrix using the methods disclosed below. In some embodiments, the ECM is digested with an enzyme, such as pepsin, collagenase, elastase, hyaluronidase, or proteinase K, and the MBVs are isolated. In other embodiments, the MBVs are released and separated from the ECM by changing the pH with solutions such as glycine HCL, citric acid, ammonium hydroxide, use of chelating agents such as, but not limited to, EDTA, EGTA, by ionic strength and or chaotropic effects with the use of salts such as, but not limited to potassium chloride (KCl), sodium chloride, magnesium chloride, sodium iodide, sodium thiocyanate, or by exposing ECM to denaturing conditions like guanidine HCl or Urea.

In particular examples, the MBVs are prepared following digestion of an ECM with an enzyme, such as pepsin, elastase, hyaluronidase, proteinase K, salt solutions, or collagenase. The ECM can be freeze-thawed, or subject to mechanical degradation.

The disclosed MBVs contain IL-33. In some embodiments, expression of CD63 and/or CD81 cannot be detected on the MBVs. Thus, the MBVs do not express CD63 and/or CD81. In a specific example, both CD63 and CD81 cannot be detected on the nanovesicles. In other embodiments, the MBVs have barely detectable levels of CD63 and CD81, such as that detectable by Western blot. These MBVs are $CD63^{lo}CD81^{lo}$. One of skill in the art can readily identify MBVs that are $CD63^{lo}CD81^{lo}$, using, for example, antibodies that specifically bind CD63 and CD81. A low level of these markers can be established using procedures such as fluorescent activated cell sorting (FACS) and fluorescently labeled antibodies to determine a threshold for low and high amounts of CD63 and CD81. The disclosed MBVs differ from nanovesicles, such as exosomes that may be transiently attached to the surface of the ECM due to their presence in biological fluids.

The MBVs include lysloxidase oxidase (Lox). Generally, nanovesicles derived from the ECM have a higher Lox content than exosomes. Lox is expressed on the surface of MBVs. Nano-LC MS/MS proteomic analysis can be used to detect Lox proteins. Quantification of Lox can be performed as previously described (Hill R C, et al., Mol Cell Proteomics. 2015; 14(4):961-73).

In certain embodiments, the MBVs comprise one or more miRNA. In specific non-limiting examples, the MBVs comprise one, two, or all three of miR-143, miR-145 and miR-181. MiR-143, miR-145 and miR-181 are known in the art.

The miR-145 nucleic acid sequence is provided in MiRbase Accession No. MI0000461, incorporated herein by reference. A miR-145 nucleic acid sequence is CACCUUGUCCUCACGGUCCAGUUUUCCCAGGAAUCCCUUAGAUGCUAAGAUGGGGA UUCCUGGAAAUACUGUUCUUGAGGUCAUGGUU (SEQ ID NO: 1). An miR-181 nucleic acid sequence is provided in miRbase Accession No. MI0000269, incorporated herein by reference. A miR-181 nucleic acid sequence is: AGAAGGGCUAUCAGGCCAGCCUUCAGAGGACUCCAAGGAACAUUCAACGCUGUCGG UGAGUUUGGGAUUUGAAAAAACCACUGACCGUUGACUGUACCUUGGGGUCCUUA (SEQ ID NO: 2). The miR-143 nucleic acid sequence is provided in NCBI Accession No. NR_029684.1, Mar. 30, 2018, incorporated herein by reference. A miR-143 nucleic acid sequence is: GCGCAGCGCC CUGUCUCCCA GCCUGAGGUG CAGUGCUGCA UCUCUGGUCA GUUGGGAGUC UGAGAUGAAG CACUGUAGCU CAGGAAGAGA GAAGUUGUUC UGCAGC (SEQ ID NO: 3).

In some embodiments, following administration, the MBVs maintain expression of CD68 and CD-11b on macrophages in the subject. In the disclosed experimental studies, nanovesicle treated macrophages are predominantly F4/80+Fizz1+indicating an M2 phenotype. Thus, in some embodiments, the macrophages maintain an M2 phenotype.

The MBVs disclosed herein can be formulated into compositions for pharmaceutical delivery, and used in bioscaffolds and devices. The MBVs are disclosed in PCT Publication No. WO 2017/151862, which is incorporated herein by reference.

Isolation of MBVs from the ECM

To produce MBVs, ECM can be produced by any cells of interest, or can be utilized from a commercial source, see above. The MBVs can be produced from the same species, or a different species, than the subject being treated. In some embodiments, these methods include digesting the ECM with an enzyme to produce digested ECM. In specific embodiments, the ECM is digested with one or more of pepsin, elastase, hyaluronidase, collagenase a metalloproteinase, and/or proteinase K. In a specific non-limiting example, the ECM is digested with only elastase and/or a metalloproteinase. In another non-limiting example, the ECM is not digested with collagenase and/or trypsin and/or proteinase K. In other embodiments, the ECM is treated with a detergent. In further embodiments, the method does not include the use of enzymes. In specific non-limiting examples, the method utilizes chaotropic agents or ionic strength to isolate MBVs such as salts, such as potassium chloride. In additional embodiments, the ECM can be manipulated to increase MBV content prior to isolation of MBVs.

In some embodiments, the ECM is digested with an enzyme. The ECM can be digested with the enzyme for about 12 to about 48 hours, such as about 12 to about 36 hours. The ECM can be digested with the enzyme for about 12, about 24 about 36 or about 48 hours. In one specific non-limiting example, the ECM is digested with the enzyme at room temperature. However, the digestion can occur at about 4° C., or any temperature between about 4° C. and 25° C. Generally, the ECM is digested with the enzyme for any length of time, and at any temperature, sufficient to remove collagen fibrils. The digestion process can be varied depending on the tissue source. Optionally, the ECM is processed by freezing and thawing, either before or after digestion with the enzyme. The ECM can be treated with detergents, including ionic and/or non-ionic detergents.

The digested ECM is then processed, such as by centrifugation, to isolate a fibril-free supernatant. In some embodiments the digested ECM is centrifuged, for example, for a first step at about 300 to about 1000 g. Thus, the digested ECM can be centrifuged at about 400 g to about 750 g, such as at about 400 g, about 450 g, about 500 g or about 600 g. This centrifugation can occur for about 10 to about 15 minutes, such as for about 10 to about 12 minutes, such as for about 10, about 11, about 12, about 14, about 14, or about 15 minutes. The supernatant including the digested ECM is collected.

The MBVs include Lox. In some embodiments, methods for isolating such MBVs include digesting the extracellular matrix with elastase and/or metalloproteinase to produce digested extracellular matrix, centrifuging the digested extracellular matrix to remove collagen fibril remnants and thus to produce a fibril-free supernatant, centrifuging the fibril-free supernatant to isolate the solid materials, and suspending the solid materials in a carrier.

In some embodiments, digested ECM also can be centrifuged for a second step at about 2000 g to about 3000 g. Thus, the digested ECM can be centrifuged at about 2,500 g to about 3,000 g, such as at about 2,000 g, 2,500 g, 2,750 g or 3,000 g. This centrifugation can occur for about 20 to about 30 minutes, such as for about 20 to about 25 minutes, such as for about 20, about 21, about 22, about 23, about 24, about 25, about 26, about 27, about 28, about 29 or about 30 minutes. The supernatant including the digested ECM is collected.

In additional embodiments, the digested ECM can be centrifuged for a third step at about 10,000 to about 15,000 g. Thus, the digested ECM can be centrifuged at about 10,000 g to about 12,500 g, such as at about 10,000 g, 11,000 g or 12,000 g. This centrifugation can occur for about 25 to about 40 minutes, such as for about 25 to about 30 minutes, for example for about 25, about 26, about 27, about 28, about 29, about 30, about 31, about 32, about 33, about 34, about 35, about 36, about 37, about 38, about 39 or about 40 minutes. The supernatant including the digested ECM is collected.

One, two or all three of these centrifugation steps can be independently utilized. In some embodiments, all three centrifugation steps are utilized. The centrifugation steps can be repeated, such as 2, 3, 4, or 5 times. In one embodiment, all three centrifugation steps are repeated three times.

In some embodiments, the digested ECM is centrifuged at about 500 g for about 10 minutes, centrifuged at about 2,500 g for about 20 minutes, and/or centrifuged at about 10,000 g for about 30 minutes. These step(s), such as all three steps are repeated 2, 3, 4, or 5 times, such as three times. Thus, in one non-limiting example, the digested ECM is centrifuged at about 500 g for about 10 minutes, centrifuged at about 2,500 g for about 20 minutes, and centrifuged at about 10,000 g for about 30 minutes. These three steps are repeated three times. Thus, a fibril-free supernatant is produced.

The fibril-free supernatant is then centrifuged to isolate the MBVs. In some embodiments, the fibril-free supernatant is centrifuged at about 100,000 g to about 150,000 g. Thus, the fibril-free supernatant is centrifuged at about 100,000 g to about 125,000 g, such as at about 100,000 g, about 105,000 g, about 110,000 g, about 115,000 g or about 120,000 g. This centrifugation can occur for about 60 to about 90 minutes, such as about 70 to about 80 minutes, for example for about 60, about 65, about 70, about 75, about 80, about 85 or about 90 minutes. In one non-limiting example, the fiber-free supernatant is centrifuged at about 100,000 g for about 70 minutes. The solid material is collected, which is the MBVs. These MBVs then can be re-suspended in any carrier of interest, such as, but not limited to, a buffer.

In further embodiments the ECM is not digested with an enzyme. In these methods, ECM is suspended in an isotonic saline solution, such as phosphate buffered saline. Salt is then added to the suspension so that the final concentration of the salt is greater than about 0.1 M. The concentration can be, for example, up to about 3 M, for example, about 0.1 M salt to about 3 M, or about 0.1 M to about 2M. The salt can be, for example, about 0.1M, 0.15M, 0.2M, 0.3M, 0.4 M, 0.7 M, 0.6 M, 0.7 M, 0.8M., 0.9M, 1.0 M, 1.1 M, 1.2 M, 1.3 M, 1.4 M, 1.5M, 1.6 M, 1.7 M, 1.8M, 1.9 M, or 2M. In some non-limiting examples, the salt is potassium chloride, sodium chloride or magnesium chloride. In other embodiments, the salt is sodium chloride, magnesium chloride, sodium iodide, sodium thiocyanate, a sodium salt, a lithium salt, a cesium salt or a calcium salt.

In some embodiments, the ECM is suspended in the salt solution for about 10 minutes to about 2 hours, such as about 15 minutes to about 1 hour, about 30 minutes to about 1 hour, or about 45 minutes to about 1 hour. The ECM can be suspended in the salt solution for about 15, 20, 25, 30, 35, 40, 45, 50, 55, 60, 65, 70, 75, 80, 85, 90, 95, 100, 105, 110, 115 or 120 minutes. The ECM can be suspended in the salt solution at temperatures from 4° C. to about 50° C., such as, but not limited to about 4° C. to about 25° C. or about 4° C. to about 37° C. In a specific non-limiting example, the ECM is suspended in the salt solution at about 4° C. In other specific non-limiting examples, the ECM is suspended in the salt solution at about 22° C. or about 25° C. (room temperature). In further non-limiting examples, the ECM is suspended in the salt solution at about 37° C.

In some embodiments, the method includes incubating an extracellular matrix at a salt concentration of greater than about 0.4 M; centrifuging the digested extracellular matrix to remove collagen fibril remnants, and isolating the supernatant; centrifuging the supernatant to isolate the solid materials; and suspending the solid materials in a carrier, thereby isolating MBVs from the extracellular matrix.

Following incubation in the salt solution, the ECM is centrifuged to remove collagen fibrils. In some embodiments, digested ECM also can be centrifuged at about 2000 g to about 5000 g. Thus, the digested ECM can be centrifuged at about 2,500 g to about 4,500 g, such as at about 2,500 g, about 3,000 g, 3,500, about 4,000 g, or about 4,500 g. In one specific non-limiting example, the centrifugation is at about 3,500 g. This centrifugation can occur for about 20 to about 40 minutes, such as for about 25 to about 35 minutes, such as for about 20, about 21, about 22, about 23, about 24, about 25, about 26, about 27, about 28, about 29, about 30 minutes, about 31, about 32, about 33 about 34 or about 35 minutes. The supernatant is then collected.

In additional embodiments, the supernatant then can be centrifuged for a third step at about 100,000 to about 150,000 g. Thus, the digested ECM can be centrifuged at about 100,000 g to about 125,000 g, such as at about 100,000 g, 110,000 g or 120,000 g. This centrifugation can occur for about 30 minutes to about 2.5 hour, such as for about 1 hour to about 3 hours, for example for about 30 minutes, about 45 minutes, about 60 minutes, about 90 minutes, or about 120 minutes (2 hours). The solid materials are collected and suspended in a solution, such as buffered saline, thereby isolating the MBVs.

In yet other embodiments, the ECM is suspended in an isotonic buffered salt solution, such as, but not limited to, phosphate buffered saline. Centrifugation or other methods can be used to remove large particles (see below). Ultrafiltration is then utilized to isolate MBVs from the ECM, particles between about 10 nm and about 10,000 nm, such as between about 10 and about 1,000 nm, such as between about 10 nm and about 300 nm.

In specific non-limiting examples, the isotonic buffered saline solution has a total salt concentration of about 0.164 mM, and a pH of about 7.2 to about 7.4. In some embodiments, the isotonic buffered saline solution includes 0.002 M KCl to about 0.164 M KCL, such as about 0.0027 M KCl (the concentration of KCL in phosphate buffered saline). This suspension is then processed by ultracentrifugation.

Following incubation in the isotonic buffered salt solution, the ECM is centrifuged to remove collagen fibrils. In some embodiments, digested ECM also can be centrifuged at about 2000 g to about 5000 g. Thus, the digested ECM can be centrifuged at about 2,500 g to about 4,500 g, such as at about 2,500 g, about 3,000 g, 3,500, about 4,000 g, or about 4,500 g. In one specific non-limiting example, the centrifugation is at about 3,500 g. This centrifugation can occur for about 20 to about 40 minutes, such as for about 25 to about 35 minutes, such as for about 20, about 21, about 22, about 23, about 24, about 25, about 26, about 27, about 28, about 29, about 30 minutes, about 31, about 32, about 33 about 34 or about 35 minutes.

Microfiltration and centrifugation can be used and combined to remove large molecular weight materials from the suspension. In one embodiment, large size molecule materials, such as more than 200 nm are removed using microfiltration. In another embodiment, large size materials are removed by the use of centrifugation. In a third embodiment both microfiltration and ultracentrifugation are used to remove large molecular weight materials. Large molecular weight materials are removed from the suspended ECM, such as materials greater than about 10,000 nm, greater than about 1,000 nm, greater than about 500 nm, or greater than about 300 nm.

The effluent for microfiltration or the supernatant is then subjected to ultrafiltration. Thus, the effluent, which includes particle of less than about 10,000 nm, less than about 1,000 nm, less than about 500 nm, or less than about 300 nm is collected and utilized. This effluent is then subjected to ultrafiltration with a membrane with a molecular weight cutoff (MWCO) of 3,000 to 100,000, 100,000 MWCO was used in the example.

Methods for Treating a Subject

The presently disclosed methods include administering to the subject a therapeutically effective amount of MBVs containing IL-33, thereby treating the subject, and inhibiting a disease or disorder in the subject. In some embodiments, the methods prevent the disease or disorder.

In one non-limiting embodiment, the disease or disorder is fibrosis of an organ or tissue. For example, the fibrosis is cirrhosis of the liver, pulmonary fibrosis, cardiac fibrosis, mediastinal fibrosis, arthrofibrosis, myelofibrosis, nephrogenic systemic fibrosis, keloid fibrosis, scleroderma fibrosis, renal fibrosis, lymphatic tissue fibrosis, arterial fibrosis, capillary fibrosis, vascular fibrosis, or pancreatic fibrosis. In one embodiment, the fibrosis is pulmonary fibrosis. The fibrosis may include idiopathic pulmonary fibrosis, pulmonary fibrosis resulting from disease or exposure to environmental toxins, or radiation induced pulmonary fibrosis. In yet another embodiment, the fibrosis is cardiac fibrosis. The cardiac fibrosis may include reactive interstitial fibrosis, replacement fibrosis, infiltrative fibrosis, or endomyocardial fibrosis. In one embodiment, the fibrosis is associated with acute or chronic organ rejection. For example, in one embodiment, the fibrosis is cardiac fibrosis associated with acute or chronic rejection of a transplanted heart.

In another non-limiting embodiment, the disease or disorder is a cardiac disease or disorder. In one embodiment, the disease or disorder is a cardiac disease or disorder that is not myocardial infarction. In another embodiment, the cardiac disease or disorder is a cardiac disease or disorder that is not myocardial ischemia. In yet another embodiment, the cardiac diseases or disorder is a cardiac disease or disorder that is not myocardial infarction or myocardial ischemia. In one embodiment, the disease or disorder is myocardial infarction or myocardial ischemia. In one embodiment, the cardiac disease or disorder is selected from myocardial infarction, myocardial ischemia, acute coronary syndrome, chronic stable angina pectoris, unstable angina pectoris, angioplasty, transient ischemic attack, ischemic-reperfusion injury, claudication(s), vascular occlusion(s), arteriosclerosis, heart failure, chronic heart failure, acute decompensated heart failure, cardiac hypertrophy, aortic valve disease, aortic or mitral valve stenosis, cardiomyopathy, atrial fibrillation, heart arrhythmia, and pericardial disease. In one embodiment, the cardiac disease or disorder is selected from, acute coronary syndrome, chronic stable angina pectoris, unstable angina pectoris, angioplasty, transient ischemic attack, ischemic-reperfusion injury, claudication(s), vascular occlusion(s), arteriosclerosis, heart failure, chronic heart failure, acute decompensated heart failure, cardiac hypertrophy, aortic valve disease, aortic or mitral valve stenosis, cardiomyopathy, atrial fibrillation, heart arrhythmia, and pericardial disease. In yet another embodiment, the disease is acute coronary syndrome, chronic stable angina pectoris, unstable angina pectoris, angioplasty, transient ischemic attack, claudications, vascular occlusions, ateriosclerosis, heart failure, cardiac hypertrophy, and cardiomyopathy. In yet another embodiment, the disease is myocardial infarction, myocardial ischemia, acute coronary syndrome, chronic stable angina pectoris, unstable angina pectoris, angioplasty, transient ischemic attack, claudications, vascular occlusions, ateriosclerosis, heart failure, cardiac hypertrophy, and cardiomyopathy.

In yet another non-limiting embodiment, the disease or disorder is solid organ transplant rejection. In one embodiment, the solid organ transplanted is a liver, kidney, heart, skin, lung, pancreas, or intestine. In one embodiment, the solid organ transplanted is a lung. In another embodiment, the solid organ transplanted is a heart. In one embodiment, the transplant rejection is chronic organ transplant rejection. In another embodiment, the transplant rejection is acute organ transplant rejection.

In yet another non-limiting embodiment, the disease or disorder is rejection of transplanted tissue, for example, cardiac valves, vessels, bones, corneas, or a composite tissue allograft including face, hand, or finger.

Subjects that have or are at risk of developing a disease or disorder, such as a cardiac disease or disorder, solid organ transplant rejection, or fibrosis of an organ or tissue, can be treated by increasing IL-33 signaling through membrane-bound ST2, see Published U.S. Patent Application No. 2008/0003199 A1, incorporated herein by reference. It is disclosed herein that MBVs include IL-33, and thus can be used to these subjects. The use of MBVs, which contain membrane encapsulated IL-33, prevents IL-33 from binding to the ST2 receptor and mitigates the induction of a pro-inflammatory kinase cascade. In some non-limiting examples, the nanovesicles maintain expression of CD68 and CD-11b on macrophages in the subject.

IL-33 is stably present within the lumen of MBV. IL-33 encapsulated within the MBVs bypasses the classical ST2 receptor signaling pathway after cellular uptake of MBV to direct immune cell differentiation and/or function.

In some embodiments, a subject can be treated using the disclosed methods where the subject has or is at risk of developing a cardiac disease or disorder, including subjects who have already been diagnosed (with the methods provided herein and/or those known in the art) as having a cardiac disease or disorder as well as subjects who would be regarded as being at risk of suffering from a cardiac disease or disorder at some point in the future. This latter group of subjects includes those at risk of suffering a cardiovascular event. In more embodiments, the cardiac disease is not myocardial infarction or myocardial ischemia. In other embodiments, the disorder is cardiac fibrosis and/or heart failure. In one embodiment, the disorder is heart failure.

The methods and compositions are of use in acute, chronic, and prophylactic treatment of any cardiac diseases or disorders. As used herein, an acute treatment refers to the treatment of subjects currently having a particular disease or disorder, such as an ischemic event. Prophylactic treatment refers to the treatment of subjects at risk of having the disease or disorder, but not presently having or experiencing the symptoms of the disease or disorder. If the subject in need of treatment has a particular cardiac disease or disorder, then treating the cardiac disease or disorder refers to ameliorating, reducing or eliminating the disease or disorder or one or more symptoms arising from the disease or disorder. If the subject in need of treatment is one who is at risk of developing a cardiac disease or disorder, then treating the subject refers to reducing the risk of the subject developing the disease or disorder.

Methods are disclosed herein for preventing or treating graft-versus-host disease (GVHD). Thus, a subject can be selected for treatment that has GVHD or risk of GVHD. The GVHD can be acute or chronic.

In some embodiments, a subject is treated that is the recipient of a transplanted organ, such as a solid organ transplant. Examples of a transplanted organ include solid organ transplants include kidney, skin, liver, composite tissue allografts (CTA; includes things such as face, hand, limbs, penis) or heart. Kidney transplantation represented approximately 60% of the solid organ transplants followed by liver transplants at 21%, heart at 8%, lung at 4% and the remaining 7% represented other organ transplants such as pancreas and intestine. (OPTN/SRTR Annual Report 2004). The types of organ are not particularly limited, and include parenchymal organs, such as hearts, livers, kidneys, pancreas, lungs, and small intestines. However, the disclosed methods are also applicable to transplantation of cardiac valves, vessels, skin, bones, and corneas. Thus, a subject can be selected for treatment that has received any type of organ transplant. The transplant can be a solid organ transplant. The solid organ can be a heart. The MBVs can be administered at the time of transplant, or after the transplant procedure, such as 1, 2, 3, 4, 5, 6, 7, 8, 9, or 10 days of the transplantation. In some non-limiting examples, the MBVs can be administered directly to the transplant.

Methods are disclosed for suppressing rejection, such as acute or chronic rejection of a solid organ transplant. The types of rejection suppressed by the suppressing agents of the present invention are not particularly limited, but can be acute rejection, which becomes problematic in actual transplantation medicine. These rejections are pathological states in which allografts are recognized as foreign antigens due to differences in the major histocompatibility complex (MHC) that determines histocompatibility and are thus attacked through activation of the recipient's cytotoxic T cells and helper T cells. Acute rejection generally develops within three months of transplantation. However, rejection can also be recognized as cell infiltrations into the allograft tissue, three months or more after transplantation. The disclosed methods are of use any time after the transplantation, including within three months of transplantation or following three months of transplantation. In some embodiments, the methods improve viability of a transplanted organ by suppressing damage.

In still a further embodiment, the subject has or is at risk of having a fibrosis-related disease. Methods are also provided for reducing fibrosis using a therapeutically effective amount of MBVs. Such methods can be carried out in vitro or in vivo. As used herein, "contacting" refers to placing an agent such as MBV such that it interacts directly with one or more cells or indirectly such that the one or more cells are affected in some way as a result. When the methods are carried out in vivo, a subject is administered MBVs in an amount effective to reduce fibrosis. In further embodiments, the disclosed methods increase anatomic appropriate cells native to the tissue or organ experiencing the fibrosis.

In the case of cardiac fibrosis, a subject is administered MBVs in an amount effective to reduce fibrosis and/or increase cardiac muscle cells. Methods for assessing native cell growth or fibrotic reduction will be readily apparent to one of ordinary skill in the art. Subjects that have or are at risk of developing a fibrosis-related disease, therefore, can also be treated by administering MBVs. In specific nonlimiting embodiments, methods are provided for treating fibrosis. These include, but are not limited to, cirrhosis of the liver, pulmonary fibrosis, cardiac fibrosis, mediastinal fibrosis, arthrofibrosis, myelofibrosis, nephrogenic systemic fibrosis, keloid fibrosis, scleroderma fibrosis, renal fibrosis, lymphatic tissue fibrosis, arterial fibrosis, capillary fibrosis, vascular fibrosis, or pancreatic fibrosis. In a specific non-limiting example, the disorder is fibrosis of the lung, such as interstitial pulmonary fibrosis or fibrosis induced by an occupational exposure.

In some embodiments, for the treatment of the lung, compositions including MBV can be administered using an inhalational preparation. These inhalational preparations can include aerosols, particulates, and the like. In general, the goal for particle size for inhalation is about 1 μm or less in order that the pharmaceutical reach the alveolar region of the lung for absorption. However, the particle size can be modified to adjust the region of disposition in the lung. Thus, larger particles can be utilized (such as about 1 to about 5 μm in diameter) to achieve deposition in the respiratory bronchioles and air spaces.

For administration by inhalation, the compositions can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

In another embodiment a therapeutically effective amount of an additional agent, such as an anti-inflammatory agent, bronchodilator, enzyme, expectorant, leukotriene antagonist, leukotriene formation inhibitor, or mast cell stabilizer is administered in conjunction with the MBV. These can be administered simultaneously, such as in a single formulation, or sequentially.

The effectiveness of treatment can be measured by monitoring pulmonary function by methods known to those of skill in the art. For example, various measurable parameters of lung function can be studied before, during, or after treatment. Pulmonary function can be monitored by testing any of several physically measurable operations of a lung including, but not limited to, inspiratory flow rate, expiratory flow rate, and lung volume. A statistically significant increase, as determined by mathematical formulas and statistical methods, in one or more of these parameters indicates efficacy of the treatment.

The methods of measuring pulmonary function most commonly employed in clinical practice involve timed measurement of inspiratory and expiratory maneuvers to measure specific parameters. For example, FVC measures the total volume in liters exhaled by a patient forcefully from a deep initial inspiration. This parameter, when evaluated in conjunction with the FEV1, allows bronchoconstriction to be quantitatively evaluated. A statistically significant increase, as determined by mathematical formulas well known to those skilled in the art, in FVC or FEV1 reflects a decrease in bronchoconstriction, and indicates that therapy is effective.

A problem with forced vital capacity determination is that the forced vital capacity maneuver (i.e., forced exhalation from maximum inspiration to maximum expiration) is largely technique dependent. In other words, a given subject may produce different FVC values during a sequence of consecutive FVC maneuvers. The FEF 25-75 or forced expiratory flow determined over the midportion of a forced exhalation maneuver tends to be less technique dependent than the FVC. Similarly, the FEV1 tends to be less technique-dependent than FVC. Thus, a statistically significant increase, as determined by mathematical formulas well known to those skilled in the art, in the FEF 25-75 or FEV1 reflects a decrease in bronchoconstriction, and indicates that therapy is effective.

In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest airflow rate in liters per minute during a forced maximal exhalation, is well correlated with overall pulmonary function in a patient with asthma and other respiratory diseases. Thus, a statistically significant increase, as determined by mathematical formulas well known to those skilled in the art, in the peak expiratory flow following administration indicates that the therapy is effective.

In some embodiments, a subject is selected for treatment who already has been diagnosed and is in the course of treatment with another therapeutic agent for treating a cardiac disease or disorder or a fibrosis-related disease, or transplant rejection. The therapeutic agent can be a chemical or biological agent, but also can be non-drug treatments such as diet and/or exercise. In some embodiments, the therapeutic agent (for a cardiac disease or disorder) includes the use of a therapeutic agent which lowers levels of C-reactive protein (CRP). In other embodiments, the therapeutic agent (for a cardiac disease or disorder) includes the use of a statin. In further embodiments, a subject is selected for treatment who has a CRP level above 1 mg/L. The therapeutic agent, for example, can be an immunosuppressive agent when treating a transplant rejection. The therapy for a fibrosis-related disease, for example, can be the use of an anti-inflammatory agent or an immunosuppressive agent.

In some embodiments, a subject is selected for treatment with the disclosed methods that has a primary (first) cardiovascular event, such as, for example, a myocardial infarct or has had an angioplasty. A subject who has had a primary cardiovascular event is at an elevated risk of a secondary (second) cardiovascular event. In some embodiments, the subject has not had a primary cardiovascular event, but is at an elevated risk of having a cardiovascular event because the subject has one or more risk factors. Examples of risk factors for a primary cardiovascular event include: hyperlipidemia, obesity, diabetes mellitus, hypertension, pre-hypertension, elevated level(s) of a marker of systemic inflammation, age, a family history of cardiovascular events and cigarette smoking. The degree of risk of a cardiovascular event depends on the multitude and the severity or the magnitude of the risk factors that the subject has. Risk charts and prediction algorithms are available for assessing the risk of cardiovascular events in a subject based on the presence and severity of risk factors. One such example is the Framingham Heart Study risk prediction score. The subject is at an elevated risk of having a cardiovascular event if the subject's 10-year calculated Framingham Heart Study risk score is greater than 5%, 6%, 7%, 8%, 9%, 10%, 11%, 12%, 13%, 14%, 15%, 16%, 17%, 18%, 19%, 20% or more. Another method for assessing the risk of a cardiovascular event in a subject is a global risk score that incorporates a measurement of a level of a marker of systemic inflammation, such as CRP, into the Framingham Heart Study risk prediction score. Other methods of assessing the risk of a cardiovascular event in a subject include coronary calcium scanning, cardiac magnetic resonance imaging and/or magnetic resonance angiography. In some embodiments, the subject selected for treatment with the disclosed methods had a primary cardiovascular event and has one or more other risk factors. In another embodiment, the subject is on statin therapy to reduce lipid levels. In another embodiment, the subject has healthy lipid levels (i.e., the subject is not hyperlipidemic). Accordingly, in one embodiment, a patient is administered MBV according to methods of the invention in order to prevent or reduce the risk that the patient develops a cardiac disease or disorder. In other words, the MBV are administered to the patient as prophylaxis against a cardiac disease or disorder. In such instances, the patient is in need of prophylaxis because the patient exhibits one or more risk factors for a cardiac disease or disorder; however, the patient has not yet been diagnosed with or shown all symptoms required for diagnosis of the cardiac disease or disorder. In some embodiments, a subject is selected for treatment that is having or has had a stroke. Stroke (also referred to herein as ischemic stroke and/or cerebrovascular ischemia) is defined by the World Health Organization as a rapidly developing clinical sign of focal or global disturbance of cerebral function with symptoms lasting at least 24 hours. Strokes are also implicated in deaths where there is no apparent cause other than an effect of vascular origin. Strokes are typically caused by blockages or occlusions of the blood vessels to the brain or within the brain. With complete occlusion, arrest of cerebral circulation causes cessation of neuronal electrical activity within seconds. Within a few minutes after the deterioration of the energy state and ion homeostasis, depletion of high energy phosphates, membrane ion pump failure, efflux of cellular potassium, influx of sodium chloride and water, and membrane depolarization occur. If the occlusion persists for more than five to ten minutes, irreversible damage results. With incomplete ischemia, however, the outcome is difficult to evaluate and depends largely on residual perfusion and the availability of oxygen. After a thrombotic occlusion of a cerebral vessel, ischemia is rarely total. Some residual perfusion usually persists in the ischemic area, depending on collateral blood flow and local perfusion pressure. The disclosed methods are of use for the treatment of a stroke.

Although an ischemic event can occur anywhere in the vascular system, the carotid artery bifurcation and the origin of the internal carotid artery are the most frequent sites for thrombotic occlusions of cerebral blood vessels, which result in cerebral ischemia. The symptoms of reduced blood flow due to stenosis or thrombosis are similar to those caused by middle cerebral artery disease. Flow through the ophthalmic artery is often affected sufficiently to produce amaurosis fugax or transient monocular blindness. Severe bilateral internal carotid artery stenosis may result in cerebral hemispheric hypoperfusion. This manifests with acute headache ipsilateral to the acutely ischemic hemisphere. Occlusions or decrease of the blood flow with resulting ischemia of one anterior cerebral artery distal to the anterior communicating artery produces motor and cortical sensory symptoms in the contralateral leg and, less often, proximal arm. Other manifestations of occlusions or underperfusion of the anterior cerebral artery include gait ataxia and sometimes urinary incontinence due to damage to the parasagittal frontal lobe. Language disturbances manifested as decreased spontaneous speech may accompany generalized depression of psychomotor activity.

A subject having a stroke is so diagnosed by symptoms experienced and/or by a physical examination including interventional and non-interventional diagnostic tools such as CT and MR imaging. A subject having a stroke may present with one or more of the following symptoms: paralysis, weakness, decreased sensation and/or vision, numbness, tingling, aphasia (e.g., inability to speak or slurred speech, difficulty reading or writing), agnosia (i.e., inability to recognize or identify sensory stimuli), loss of memory, co-ordination difficulties, lethargy, sleepiness or unconsciousness, lack of bladder or bowel control and cognitive decline (e.g., dementia, limited attention span, inability to concentrate). Using medical imaging techniques, it may be possible to identify a subject having a stroke as one having an infarct or one having hemorrhage in the brain.

The compositions and methods provided can be used in patients who have experienced a stroke or can be a prophylactic treatment to prevent stroke. Short term prophylactic treatment is indicated for subjects having surgical or diagnostic procedures which risk release of emboli, lowering of blood pressure or decrease in blood flow to the brain, to reduce the injury due to any ischemic event that occurs as a consequence of the procedure. Longer term or chronic prophylactic treatment is indicated for subjects having cardiac conditions that may lead to decreased blood flow to the brain, or conditions directly affecting brain vasculature. If prophylactic, then the treatment is for subjects at risk of an ischemic stroke, as described above. If the subject has experienced a stroke, then the treatment can include acute treatment. Acute treatment for stroke subjects means administration of a composition of the invention at the onset of symptoms of the condition or within 48 hours of the onset, preferably within 24 hours, more preferably within 12 hours, more preferably within 6 hours, and even more preferably within 1, 2 or 3 hours of the onset of symptoms of the condition or immediately at the time of diagnosis or at the time medical personnel suspects a stroke has occurred.

In still other embodiments, the subject can be one that has a myocardial infarction or is at risk of having a myocardial infarction. By "having a myocardial infarction" it is meant that the subject is currently having or has suffered a myocardial infarction. In some embodiments, administration occurs before (if it is suspected or diagnosed in time), or within 48 hours, although administration later, such as, for example, within 14 days, after a cardiovascular event or diagnosis or suspicion of cardiac disease or disorder may also be beneficial to the subject. Immediate administration can also include administration within 15, 20, 30, 40 or 50 minutes, within 1, 2, 3, 4, 5, 6, 7, 8, 9, 10, 12, 15, 18, 20 or 22 hours or within 1 or 2 days of the diagnosis or suspicion of a cardiovascular event or cardiac disease or disorder. In still another embodiment, MBVs containing IL-33 can be administered for a few days, one week or a few weeks (e.g., 1, 2, 3 or 4 weeks) beginning at or shortly after the time of diagnosis or suspicion of the cardiovascular event or cardiac disease or disorder.

A number of laboratory tests for the diagnosis of myocardial infarction are well known in the art. Generally, the tests may be divided into four main categories: (1) nonspecific indexes of tissue necrosis and inflammation, (2) electrocardiograms, (3) serum enzyme changes (e.g., creatine phosphokinase levels) and (4) cardiac imaging. A person of ordinary skill in the art could easily apply any of the foregoing tests to determine when a subject is at risk, is suffering, or has suffered, a myocardial infarction.

The subject can have heart failure. Heart failure is a clinical syndrome of diverse etiologies linked by the common denominator of impaired heart pumping and is characterized by the failure of the heart to pump blood commensurate with the requirements of the metabolizing tissues, or to do so only from an elevating filling pressure.

In yet other embodiments, the subject has cardiac hypertrophy. This condition is typically characterized by left ventricular hypertrophy, usually of a nondilated chamber, without obvious antecedent cause. Current methods of diagnosis include the electrocardiogram and the echocardiogram. Many patients, however, are asymptomatic and may be relatives of patients with known disease. Unfortunately, the first manifestation of the disease may be sudden death, frequently occurring in children and young adults, often during or after physical exertion.

In another embodiment, the subject has an elevated level of a marker of a cardiac disease or disorder or risk thereof. The marker can be, for example, cholesterol, low density lipoprotein cholesterol (LDLC) or a marker of systemic inflammation. An elevated level(s) of a marker is a level that is above the average for a healthy subject population (e.g., human subjects who have no signs and symptoms of a cardiac disease or disorder). When the marker is CRP, a CRP level of >1 is considered to be an elevated level.

A subject can be selected that has fibrosis. In some embodiments, the subject has been diagnosed with cirrhosis of the liver, pulmonary fibrosis, cardiac fibrosis, mediastinal fibrosis, arthrofibrosis, myelofibrosis, nephrogenic systemic fibrosis, keloid fibrosis, scleroderma fibrosis, renal fibrosis, lymphatic tissue fibrosis, arterial fibrosis, capillary fibrosis, vascular fibrosis, or pancreatic fibrosis. A subject can be selected for treatment that has been exposed to, or at risk of exposure to, inorganic particles, including, but not limited to silica, asbestos, berrylium, coal dust, or bauxite. A subject can be selected for treatment that has interstitial pulmonary fibrosis. A subject can be selected for treatment that has cardiac fibrosis. The disclosed methods can be used to treat or inhibit fibrosis in a subject.

Pharmaceutical compositions can include the MBVs and optionally one or more additional agents. These compositions can be formulated in a variety of ways for administration to a subject, or to delay, prevent, reduce the risk of developing, or treat, or reduce a disease process. The compositions described herein can also be formulated for application such that they prevent metastasis of an initial lesion. In some embodiments, the compositions are formulated for local administration, such as intracardiac administration. Local administration also may be to a graft, before and/or after transplantation into a subject. The MBVs can be administered by any route, including parenteral administration, for example, intravenous, intraperitoneal, intramuscular, intradermal, intraperitoneal, intrasternal, or intraarticular injection or infusion, or by sublingual, oral, topical, intranasal, or transmucosal administration, or by pulmonary inhalation. The appropriate route of administration can be selected by a physician. Pharmaceutical compositions including MBV can be formulated for both local use and for systemic use, formulated for use in human or veterinary medicine. In some embodiments, the composition can be administered by injection or catheter. Administration can be intravenous or intramuscular.

The disclosed compositions can be administered once or repeatedly. The disclosed compositions can be administered locally or systemically. The disclosed compositions can be administered via an intravenous injection such as a drip infusion, subcutaneous injection, local administration or any other route, once to several times a month, for example, twice a week, once a week, once every two weeks, or once every four weeks. Multiple treatments are envisioned, such as over defined intervals of time, such as daily, bi-weekly, weekly, bi-monthly or monthly. The administration schedule may be adjusted by, for example, extending the administration interval of twice a week or once a week to once every two weeks, once every three weeks, or once every four weeks. In some embodiments, the methods include monitoring organ function after transplantation and/or changes in the blood test values. The compositions can be administered to a subject prior to organ transplantation, at the time of organ transplantation, or after organ transplantation. Administration may begin whenever the suppression or prevention of disease is desired, for example, at a certain age of a subject, or after receiving a solid organ transplant.

While the disclosed methods and compositions will typically be used to treat human subjects they may also be used to treat similar or identical diseases in other vertebrates, such as other primates, dogs, cats, horses, and cows. A suitable administration format may best be determined by a medical practitioner for each subject individually. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42: 2S, 1988. The dosage form of the pharmaceutical composition will be determined by the mode of administration chosen. In some embodiments, the subject is a human, and the MBVs are from human tissue.

In some embodiments, when locally administered into cells in an affected area or a tissue of interest, such as a heart transplant, the disclosed composition increases muscle cell proliferation, and/or decreases inflammation.

When the MBV (ECM-derived nanovesicles) are provided as parenteral compositions, e.g. for injection or infusion, they are generally suspended in an aqueous carrier, for example, in an isotonic buffer solution at a pH of about 3.0 to about 8.0, preferably at a pH of about 3.5 to about 7.4, such as about 7.2 to about 7.4. Useful buffers include sodium citrate-citric acid and sodium phosphate-phosphoric acid, and sodium acetate-acetic acid buffers.

A form of repository or "depot" slow release preparation may be used so that therapeutically effective amounts of the preparation are delivered into the bloodstream over many hours or days following injection or delivery. Suitable examples of sustained-release compositions include suitable polymeric materials (such as, for example, semi-permeable polymer matrices in the form of shaped articles, e.g., films, or mirocapsules), suitable hydrophobic materials (such as, for example, an emulsion in an acceptable oil) or ion exchange resins, and sparingly soluble derivatives (such as, for example, a sparingly soluble salt). Sustained-release formulations may be administered orally, rectally, parenterally, intracistemally, intravaginally, intraperitoneally, topically (as by powders, ointments, gels, drops or transdermal patch), bucally, or as an oral or nasal spray. The pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features which allow a controlled release of the active substance. See U.S. Pat. No. 5,700,486.

The pharmaceutically acceptable carriers and excipients useful in the disclosed methods are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

The amount of MBVs administered will be dependent on the subject being treated, the severity of the affliction, and the manner of administration, and is best left to the judgment of the prescribing clinician. Within these bounds, the formulation to be administered will contain a quantity of the MBVs in amounts effective to achieve the desired effect in the subject being treated.

The exact dose is readily determined by one of skill in the art based on the potency of the specific fraction, the age, weight, sex and physiological condition of the subject. Suitable concentrations include, but are not limited to, about 1 ng/ml-100 gr/ml.

The methods provided herein for treating a subject in need thereof can include the use of additional therapeutic agents. Compositions including MBV can also include an additional therapeutic agent. Such additional therapeutic agents include anti-lipemic agents, anti-inflammatory agents, anti-thrombotic agents, fibrinolytic agents, anti-platelet agents, direct thrombin inhibitors, glycoprotein IIb/IIIa receptor inhibitors, agents that bind to cellular adhesion molecules and inhibit the ability of white blood cells to attach to such molecules (e.g., anti-cellular adhesion molecule antibodies), alpha-adrenergic blockers, beta-adrenergic blockers, cyclooxygenase-2 inhibitors, angiotensin system inhibitor, anti-arrhythmics, calcium channel blockers, diuretics, inotropic agents, vasodilators, vasopressors, thiazolidinediones, cannabinoid-1 receptor blockers, immunosuppressive agents and any combination thereof.

Anti-lipemic agents are agents that reduce total cholesterol, reduce LDLC, reduce triglycerides, and/or increase HDLC. Anti-lipemic agents include statins, non-statin anti-lipemic agents and combinations thereof. Statins are a class of medications that have been shown to be effective in lowering human total cholesterol, LDLC and triglyceride levels. Statins act at the step of cholesterol synthesis. By reducing the amount of cholesterol synthesized by the cell, through inhibition of the HMG-CoA reductase gene, statins initiate a cycle of events that culminates in the increase of LDLC uptake by liver cells. As LDLC uptake is increased, total cholesterol and LDLC levels in the blood decrease. Lower blood levels of both factors are associated with lower risk of atherosclerosis and heart disease, and the statins are widely used to reduce atherosclerotic morbidity and mortality.

Examples of statins include, but are not limited to, simvastatin (ZOCOR®), lovastatin (MEVACOR®), pravastatin (PRAVACHOL®), fluvastatin (LESCOL®), atorvastatin (LIPITOR®), cerivastatin (BAYCOL®), rosuvastatin (CRESTOR®), pitivastatin and numerous others described in U.S. Pat. Nos. 4,444,784; 4,231,938; 4,346,227; 4,739,073; 5,273,995; 5,622,985; 5,135,935; 5,356,896; 4,920,109; 5,286,895; 5,262,435; 5,260,332; 5,317,031; 5,283,256; 5,256,689; 5,182,298; 5,369,125; 5,302,604; 5,166,171; 5,202,327; 5,276,021; 5,196,440; 5,091,386; 5,091,378; 4,904,646; 5,385,932; 5,250,435; 5,132,312; 5,130,306; 5,116,870; 5,112,857, 5,102,911; 5,098,931; 5,081,136; 5,025,000; 5,021,453; 5,017,716; 5,001,144; 5,001,128; 4,997,837; 4,996,234; 4,994,494; 4,992,429; 4,970,231; 4,968,693; 4,963,538; 4,957,940; 4,950,675; 4,946,864; 4,946,860; 4,940,800; 4,940,727; 4,939,143; 4,929,620; 4,923,861; 4,906,657; 4,906,624; and 4,897,402.

Examples of statins already approved for use in humans include atorvastatin, cerivastatin, fluvastatin, pravastatin, simvastatin and rosuvastatin. The following references provide further information on HMG-CoA reductase inhibitors: Drugs and Therapy Perspectives (May 12, 1997), 9: 1-6; Chong (1997) Pharmacotherapy 17:1157-1177; Kellick (1997) Formulary 32: 352; Kathawala (1991) Medicinal Research Reviews, 11: 121-146; Jahng (1995) Drugs of the Future 20: 387-404, and Current Opinion in Lipidology, (1997), 8, 362-368. Another statin drug of note is compound 3a (S-4522) in Watanabe (1997) Bioorganic and Medicinal Chemistry 5: 437-444.

Non-statin anti-lipemic agents include but are not limited to fibric acid derivatives (fibrates), bile acid sequestrants or resins, nicotinic acid agents, cholesterol absorption inhibitors, acyl-coenzyme A: cholesterol acyl transferase (ACAT) inhibitors, cholesteryl ester transfer protein (CETP) inhibitors, LDL receptor antagonists, farnesoid X receptor (FXR) antagonists, sterol regulatory binding protein cleavage activating protein (SCAP) activators, microsomal triglyceride transfer protein (MTP) inhibitors, squalene synthase inhibitors and peroxisome proliferation activated receptor (PPAR) agonists. Examples of fibric acid derivatives include but are not limited to gemfibrozil (LOPID®), fenofibrate (TRICOR®), clofibrate (ATROMID®) and bezafibrate.

Examples of bile acid sequestrants or resins include but are not limited to colesevelam (WELCHOL®), cholestyramine (QUESTRAN® or PREVALITE®) and colestipol (COLESTID®), DMD-504, GT-102279, HBS-107 and S-8921. Examples of nicotinic acid agents include but are not limited to niacin and probucol. Examples of cholesterol absorption inhibitors include but are not limited to ezetimibe (ZETIA®). Examples of ACAT inhibitors include but are not limited to Avasimibe, CI-976 (Parke Davis), CP-113818 (Pfizer), PD-138142-15 (Parke Davis), FF1394, and numerous others described in U.S. Pat. Nos. 6,204,278; 6,165,984; 6,127,403; 6,063,806; 6,040,339; 5,880,147; 5,621,010; 5,597,835; 5,576,335; 5,321,031; 5,238,935; 5,180,717; 5,149,709, and 5,124,337.

Examples of CETP inhibitors include but are not limited to Torcetrapib, CP-529414, *CETi*-1, JTT-705, and numerous others described in U.S. Pat. Nos. 6,727,277; 6,723,753; 6,723,752; 6,710,089; 6,699,898; 6,696,472; 6,696,435; 6,683,099; 6,677,382; 6,677,380; 6,677,379; 6,677,375; 6,677,353; 6,677,341; 6,605,624; 6,586,448; 6,521,607; 6,482,862; 6,479,552; 6,476,075; 6,476,057; 6,462,092; 6,458,852; 6,458,851; 6,458,850; 6,458,849; 6,458,803; 6,455,519; 6,451,830; 6,451,823; 6,448,295; 5,512,548. One example of an FXR antagonist is Guggulsterone. One example of a SCAP activator is GW532 (GlaxoSmithKline). Examples of MTP inhibitors include but are not limited to Implitapide and R-103757. Examples of squalene synthase inhibitors include but are not limited to zaragozic acids. Examples of PPAR agonists include but are not limited to GW-409544, GW-501516, and LY-510929.

Anti-inflammatory agents include but are not limited to Alclofenac, Alclometasone Dipropionate, Algestone Acetonide, Alpha Amylase, Amcinafal, Amcinafide, Amfenac Sodium, Amiprilose Hydrochloride, Anakinra, Anirolac, Anitrazafen, Apazone, Balsalazide Disodium, Bendazac, Benoxaprofen, Benzydamine Hydrochloride, Bromelains, Broperamole, Budesonide, Carprofen, Cicloprofen, Cintazone, Cliprofen, Clobetasol Propionate, Clobetasone Butyrate, Clopirac, Cloticasone Propionate, Cormethasone Acetate, Cortodoxone, Deflazacort, Desonide, Desoximetasone, Dexamethasone Dipropionate, Diclofenac Potassium, Diclofenac Sodium, Diflorasone Diacetate, Diflumidone Sodium, Diflunisal, Difluprednate, Diftalone, Dimethyl Sulfoxide, Drocinonide, Endrysone, Enlimomab, Enolicam Sodium, Epirizole, Etodolac, Etofenamate, Felbinac, Fenamole, Fenbufen, Fenclofenac, Fenclorac, Fendosal, Fenpipalone, Fentiazac, Flazalone, Fluazacort, Flufenamic Acid, Flumizole, Flunisolide Acetate, Flunixin, Flunixin Meglumine, Fluocortin Butyl, Fluorometholone Acetate, Fluquazone, Flurbiprofen, Fluretofen, Fluticasone Propionate, Furaprofen, Furobufen, Halcinonide, Halobetasol Propionate, Halopredone Acetate, Ibufenac, Ibuprofen, Ibuprofen Aluminum, Ibuprofen Piconol, Ilonidap, Indomethacin, Indomethacin Sodium, Indoprofen, Indoxole, Intrazole, Isoflupredone Acetate, Isoxepac, Isoxicam, Ketoprofen, Lofemizole Hydrochloride, Lomoxicam, Loteprednol Etabonate, Meclofenamate Sodium, Meclofenamic Acid, Meclorisone Dibutyrate, Mefenamic Acid, Mesalamine, Meseclazone, Methylprednisolone Suleptanate, Morniflumate, Nabumetone, Naproxen, Naproxen Sodium, Naproxol, Nimazone, Olsalazine Sodium, Orgotein, Orpanoxin, Oxaprozin, Oxyphenbutazone, Paranyline Hydrochloride, Pentosan Polysulfate Sodium, Phenbutazone Sodium Glycerate, Pirfenidone, Piroxicam, Piroxicam Cinnamate, Piroxicam Olamine, Pirprofen, Prednazate, Prifelone, Prodolic Acid, Proquazone, Proxazole, Proxazole Citrate, Rimexolone, Romazarit, Salcolex, Salnacedin, Salsalate, Salycilates, Sanguinarium Chloride, Seclazone, Sermetacin, Sudoxicam, Sulindac, Suprofen, Talmetacin, Talniflumate, Talosalate, Tebufelone, Tenidap, Tenidap Sodium, Tenoxicam, Tesicam, Tesimide, Tetrydamine, Tiopinac, Tixocortol Pivalate, Tolmetin, Tolmetin Sodium, Triclonide, Triflumidate, Zidometacin, Glucocorticoids and Zomepirac Sodium.

Anti-thrombotic agents and/or fibrinolytic agents include but are not limited to tissue plasminogen activator (e.g., ACTIVASE®, ALTEPLASE®) (catalyzes the conversion of inactive plasminogen to plasmin). This may occur via interactions of prekallikrein, kininogens, Factors XII, XIIIa, plasminogen proactivator, and tissue plasminogen activator TPA) Streptokinase, Urokinase, Anisoylated Plasminogen-Streptokinase Activator Complex, Pro-Urokinase, (Pro-UK), rTPA (ACTIVASE®, ALTEPLASE®); r denotes recombinant), rPro-UK, Abbokinase, Eminase, Sreptase Anagrelide Hydrochloride, Bivalirudin, Dalteparin Sodium, Danaparoid Sodium, Dazoxiben Hydrochloride, Efegatran Sulfate, Enoxaparin Sodium, Ifetroban, Ifetroban Sodium, Tinzaparin Sodium, retaplase, Trifenagrel, Warfarin, Dextrans, aminocaproic acid (AMICAR®) and tranexamic acid (AMSTAT®).

Anti-platelet agents include but are not limited to Clopridogrel, Sulfinpyrazone, Aspirin, Dipyridamole, Clofibrate, Pyridinol Carbamate, PGE, Glucagon, Antiserotonin drugs, Caffeine, Theophyllin Pentoxifyllin, Ticlopidine and Anagrelide. Direct thrombin inhibitors include but are not limited to hirudin, hirugen, hirulog, agatroban, PPACK and thrombin aptamers. Glycoprotein IIb/IIIa receptor inhibitors are both antibodies and non-antibodies, and include, but are not limited to, REOPRO® (abcixamab), lamifiban and tirofiban. Agents that bind to cellular adhesion molecules and inhibit the ability of white blood cells to attach to such molecules include polypeptide agents. Such polypeptides include polyclonal and monoclonal antibodies, prepared according to conventional methodology. Such antibodies already are known in the art and include anti-ICAM 1 antibodies as well as other such antibodies.

Examples of alpha-adrenergic blockers include but are not limited to: doxazocin, prazocin, tamsulosin, and tarazosin. Beta-adrenergic receptor blocking agents are a class of drugs that antagonize the cardiovascular effects of catecholamines in angina pectoris, hypertension and cardiac arrhythmias. Beta-adrenergic receptor blockers include, but are not limited to, atenolol, acebutolol, alprenolol, befunolol, betaxolol, bunitrolol, carteolol, celiprolol, hydroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitrilHCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol, 7-(2-hydroxy-3-t-butylaminpropoxy)phthalide. The above-identified compounds can be used as isomeric mixtures, or in their respective levorotating or dextrorotating form.

Selective COX-2 inhibitors are known in the art and can be utilized. These include, but are not limited to, F COX-2 inhibitors described in U.S. Pat. Nos. 5,521,213; 5,536,752;

5,550,142; 5,552,422; 5,604,253; 5,604,260; 5,639,780; 5,677,318; 5,691,374; 5,698,584 ; 5,710,140 5,733,909; 5,789,413; 5,817,700; 5,849,943; 5,861,419; 5,922,742; 5,925,631; and 5,643,933. A number of the above-identified COX-2 inhibitors are prodrugs of selective COX-2 inhibitors and exert their action by conversion in vivo to the active and selective COX-2 inhibitors. The active and selective COX-2 inhibitors formed from the above-identified COX-2 inhibitor prodrugs are described in PCT Publication No. WO 95/00501, PCT Publication No. WO 95/18799, and U.S. Pat. No. 5,474,995.

An angiotensin system inhibitor is an agent that interferes with the function, synthesis or catabolism of angiotensin II. These agents include, but are not limited to, angiotensin-converting enzyme (ACE) inhibitors, angiotensin II antagonists, angiotensin II receptor antagonists, agents that activate the catabolism of angiotensin II, and agents that prevent the synthesis of angiotensin I from which angiotensin II is ultimately derived. Examples of classes of such compounds include antibodies (e.g., to renin), amino acids and analogs thereof (including those conjugated to larger molecules), peptides (including peptide analogs of angiotensin and angiotensin I), pro-renin related analogs, etc. Among the most potent and useful renin-angiotensin system inhibitors are renin inhibitors, ACE inhibitors, and angiotensin II antagonists.

Angiotensin II antagonists are compounds which interfere with the activity of angiotensin II by binding to angiotensin II receptors and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid. Stability can be enhanced by other replacements that slow degeneration in vivo. Examples of angiotensin II receptor antagonists include but are not limited to: Candesartan (Alacand), IRBESARTAN® (Avapro), Losartan (COZAARS®), Telmisartan (MICARDIS®), and Valsartan (DIOVAN®). Other examples of angiotensin II antagonists include: peptidic compounds (e.g., saralasin, [(Sar$^{1}$)(Val$^{5}$)(Ala$^{8}$)]angiotensin-(1-8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., *J. Pharmacol. Exp. Ther.* 247(1), 1-7 (1988)); 4, 5, 6, 7-tetrahydro-1H-imidazo[4,5-c]pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253, 310, Jan. 20, 1988); ES8891 (N-morpholinoacetyl-(-1-naphthyl)-L-alanyl-(4, thiazolyl)-L-alanyl (35, 45)-4-amino-3-hydroxy-5-cyclo-hexapentanoyl-N-hexylamide, Sankyo Company, Ltd., Tokyo, Japan); SKF108566 (E-alpha-2-[2-butyl-1-(carboxy phenyl)methyl]1H-imidazole-5-yl[methylane]-2-thiophenepropanoic acid, Smith Kline Beecham Pharmaceuticals, PA); LOSARTAN® (DUP753/MK954, DuPont Merck Pharmaceutical Company); Remikirin (RO42-5892, F. Hoffman LaRoche AG); $A_2$ agonists (Marion Merrill Dow) and certain non-peptide heterocycles (G.D.Searle and Company).

Angiotensin converting enzyme (ACE), is an enzyme which catalyzes the conversion of angiotensin I to angiotensin II. ACE inhibitors include amino acids and derivatives thereof, peptides, including di and tri peptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344, 949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

Renin inhibitors are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di and tri peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075, 451); fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837; 5,064,965; 5,063, 207; 5,036,054; 5,036,053, 5,034,512, and 4,894,437).

Calcium channel blockers are a chemically diverse class of compounds having important therapeutic value in the control of a variety of diseases including several cardiovascular disorders, such as hypertension, angina, and cardiac arrhythmias (Fleckenstein, Cir. Res. v. 52, (suppl. 1), p. 13-16 (1983); Fleckenstein, *Experimental Facts and Therapeutic Prospects*, John Wiley, New York (1983); McCall, D., *Curr Pract Cardiol, v.* 10, p. 1-11 (1985)). Calcium channel blockers are a heterogenous group of drugs that prevent or slow the entry of calcium into cells by regulating cellular calcium channels. (Remington, *The Science and Practice of Pharmacy*, Nineteenth Edition, Mack Publishing Company, Eaton, Pa., p. 963 (1995)). Most of the currently available calcium channel blockers, and useful according to the present invention, belong to one of three major chemical groups of drugs, the dihydropyridines, such as nifedipine, the phenyl alkyl amines, such as verapamil, and the benzothiazepines, such as diltiazem. Other calcium channel blockers useful according to the invention, include, but are not limited to, aminone, amlodipine, bencyclane, felodipine, fendiline, flunarizine, isradipine, nicardipine, nimodipine, perhexylene, gallopamil, tiapamil and tiapamil analogues (such as 1993RO-11-2933), phenyloin, barbiturates, and the peptides dynorphin, omega-conotoxin, and omega-agatoxin, and the like and/or pharmaceutically acceptable salts thereof.

Diuretics include but are not limited to: carbonic anhydrase inhibitors, loop diuretics, potassium-sparing diuretics, thiazides and related diuretics. Vasodilators include but are not limited to coronary vasodilators and peripheral vasodilators. Vasopressors are agents that produce vasoconstriction and/or a rise in blood pressure. Vasopressors include but are not limited to: dopamine, ephedrine, epinephrine, Methoxamine HCl (VASOXYL®), phenylephrine, phenylephrine HCl (NEO-SYNEPHRINE®), and Metaraminol. Thiazolidinediones include but are not limited to: rosigletazone (AVANDIA®), pioglitazone (ACTOS®), troglitazone (Rezulin). Any of these can be used in the disclosed methods and compositions.

Immunosuppressive agents include but are not limited to steroids, calcineurin inhibitors, anti-proliferative agents, biologics, and monoclonal or polyclonal antibodies. Biologics include but are not limited to recombinant or synthesized peptides and proteins, and synthesized forms nucleic acids. The steroid can be a corticosteroid. Examples of corticosteroids include but are not limited to prednisone, hydrocortisone, and methylprednisone. Examples of calcineurin inhibitors include but are not limited to Tacrolimus, FK506, ADVAGRAFT®, PROGRAF®, ENVARSUS XR®, HECORIA®, ASTAGRAF XL®, and cyclosporine (CEQUAS®, NEORAL®, RESTASIS®), NEORAL®, PIMECROLIMUS®, SANDIMMUNE®, PROTOPIC®, GENGRAFT®, and ELIDEL®. Examples of monoclonal antibodies include but are not limited to anti-CD3 antibody (MUROMONAB-CD3, ORTHOCLONE® OKT3), Visilizumab (NUVION®), anti-CD52 (Altemtuzumab (CAMPATH®-1H)), anti-CD25 (Basiliximab (SIMULECT®)), anti-CD20 (Rituximab (RITUXAN®), Obinutuzumab (GAZYVA®), Ocrelizumab (OCREVUS®)), anti-complement proteins (Eculizumab (SOLIRIS®)), anti-costimulatory molecules (Bleselumab, LULIZUMAB®), and anti-cytokine or cytokine receptors (Tocilizumab (ACTEMRA®), Ustekinumab (STELARA®), Canakinumab (ILARIS®), Secukinumab (COSENTYX®), Siltuximab (SYLVANT®), Brodalumab (SILIQ®), Ixekizumab (TALTZ®), Sarilumab (KEVAZRA®), Guselkumab (TREMFYA®), and Tildrakizumab (ILUMYA®)). Examples of polyclonal antibodies include but are not limited to anti-thymocyte globulin-equine (ATGAM®) and anti-thymocyte globulin-rabbit (RATG thymoglobulin), polyclonal human IgG immunoglobulins (IVIG, BIVIGAM®, CARIMUNE®, CUTAQUIG®). Examples of biologic proteins include but are not limited to soluble CTLA-4-Ig (ABATACEPT®), CI-esterase inhibitor (C1-INH, CINRYZE®, HAEGARDA®), IL-1 or IL-1R antagonists (Anakinra (KINERET®), Rilonacept (ARCALYST®), and IgG-degrading enzyme of *Streptococcus pyogenes* (IdeS). Anti-proliferative or anti-metabolite agents include but are not limited to mycophenolate mofetil, mycophenolate sodium, azathioprine, cyclophosphamide, rapamycin, sirolimus (RAPAMUNE®), Everolimus (AFINITOR®). Other immunosuppressants include but are not limited to sulfasalazine, azulfidine, methoxsalen, and thalidomide. Any of these can be used in the disclosed compositions and methods. In some embodiments, the immunosuppressive agent is a calcineurin inhibitor, an antiproliferative agent, an mTOR inhibitor, and/or steroids. In specific non-limiting examples, the calcineurin inhibitor is tacrolimus or cyclosporine; wherein the antiproliferative agent is mycophenolate; the mTOR inhibitor is sirolimus, and/or the steroid is prednisone, hydrocortisone, or cortisone.

The methods provided can also include the use of other therapies, such as diet and/or exercise. In some embodiments, these therapies are in addition to therapeutic treatment with MBV. "Co-administering," as used herein, refers to administering simultaneously two or more therapeutic agents (e.g., MBV, and a second therapeutic agent) as an admixture in a single composition, or sequentially, and, in some embodiments, close enough in time so that the compounds may exert an additive or even synergistic effect. In other embodiments, the therapeutic agents are administered concomitantly. In still other embodiments, one therapeutic agent is administered prior to or subsequent to another therapeutic agent.

The dose of MBV to be administered is therapeutically effective, and depends on a number of factors, including the route of administration, and can be determined by a skilled clinician. In some embodiments, the concentration of MBVs is about $1\times10^5$ to about $1\times10^{12}$ per ml, such as $1\times10^6$ to about $1\times10^{11}$ per ml, about $1\times10^7$ to about $1\times10^{11}$ per ml, or about $1\times10^8$ to about $1\times10^{10}$ per ml. In some non-limiting examples, administered locally, a dose of about $1\times10^8$ to about $1\times10^{10}$ per ml is provided, such as about $1\times10^8$ per ml, about $5\times10^8$ per ml, about $1\times10^9$ per ml, about $5\times10^9$ per ml, or about $1\times10^{10}$ per ml. When administered locally, the volume is appropriate for the site. Exemplary non-limiting volumes are 0.1 ml into the vitreous; 1.0 ml when spread on the surface of an area of a transplant, 1.5 ml when injected into the edges of a 3 cm long skin incision; 0.15 ml when injected into the stroke cavity wherein the entire cavity is approx. 1.40 $mm^3$. One of skill in the art can readily identify an appropriate volume for a location. Generally, the volume is effective for treatment, and does not induce damage at the site of interest.

Generally, doses of active compounds or agents can be from about 0.01 mg/kg per day to 1000 mg/kg per day. It is expected that doses ranging from 1-5 mg/kg, 5-50 mg/kg or 50-100 mg/kg can be suitable for oral administration and in one or several administrations per day. Lower doses will result from other forms of administration, such as intravenous administration. In the event that a response in a human subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

When administered, pharmaceutical preparations are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. See U.S. Published Application No. 2008/0003199, IL-33 in the treatment and diagnosis of diseases and disorders, incorporated herein by reference.

Methods for Increasing Myoblast Differentiation

Methods are also disclosed for increasing myoblast differentiation. These methods include contacting a myoblast with an effective amount of isolated nanovesicles derived from an extracellular matrix, wherein the nanovesicles contain interleukin (IL)-33 and comprise lysyl oxidase, and wherein the nanovesicles a) do not express CD63 or CD81, or b) are $CD63^{lo}CD81^{lo}$. The myoblast can be in vivo or in vitro.

Myogenesis, the process of muscle cell determination, differentiation, and fusion into multinucleated syncytia, is essential for normal muscle development and tissue regeneration following injury.

In some embodiments, treatment aimed at limiting the consequences of postinfarction cardiac dysfunction, includes the transplantation of cells (myocytes or stem cells) into the damaged left ventricle. The transplanted cells increase the ventricular ejection fraction by participating in cardiac contractions. Large numbers of potentially contractile cells are required for intramyocardial grafting. Thus, the disclosed methods can expand cell populations suitable for use as cardiac or skeletal muscle grafts.

EXEMPLARY EMBODIMENTS

Clause 1. A method for treating or inhibiting a disorder in a subject having or at risk of having the disorder, comprising: selecting a subject having or at risk of having the disorder, and administering to the subject a therapeutically effective amount of isolated nanovesicles derived from an extracellular matrix, wherein the nanovesicles contain interleukin (IL)-33 and comprise lysyl oxidase, and wherein the nanovesicles a) do not express CD63 or CD81, or b) are $CD63^{lo}CD81^{lo}$, thereby treating or inhibiting the disorder in the subject, wherein the disorder is a) fibrosis of an organ or tissue; b) solid organ transplant rejection; or c) a cardiac disease that is not myocardial infarction or myocardial ischemia.

Clause 2. The method of clause 1, wherein the extracellular matrix is a mammalian extracellular matrix.

Clause 3. The method of clause 2, wherein the mammalian extracellular matrix is a human extracellular matrix.

Clause 4. The method of any one of clauses 1-3, wherein the extracellular matrix is from esophageal tissue, urinary bladder, small intestinal submucosa, dermis, umbilical cord, pericardium, cardiac tissue, or skeletal muscle.

Clause 5. The method of any one of clauses 1-4, wherein the nanovesicles comprise miR-145 and/or miR-181.

Clause 6. The method of any one of clauses 1-5, wherein the disorder is the solid organ transplant rejection, and wherein the subject is a recipient of a transplanted solid organ.

Clause 7. The method of clause 6, wherein the nanovesicles are administered to the transplanted solid organ.

Clause 8. The method of clause 7, wherein the transplanted solid organ is a heart.

Clause 9. The method of any one of clauses 1-5, wherein the disorder is the cardiac disease.

Clause 10. The method of any one of clauses 1-5, wherein the cardiac disease is heart failure or cardiac ischemia.

Clause 11. The method of any of clauses 1-5, wherein the cardiac disease is include acute coronary syndrome, chronic stable angina pectoris, unstable angina pectoris, angioplasty, transient ischemic attack, ischemic-reperfusion injury, claudication(s), vascular occlusion(s), arteriosclerosis, heart failure, chronic heart failure, acute decompensated heart failure, cardiac hypertrophy, cardiac fibrosis, aortic valve disease, aortic or mitral valve stenosis, cardiomyopathy, atrial fibrillation, heart arrhythmia, and pericardial disease Clause 12. The method of any one of clauses 1-11, wherein the nanovesicles are administered intravenously.

Clause 13. The method of any one of clauses 1-5, wherein the disorder is the fibrosis of an organ or tissue.

Clause 14. The method of clause 13, wherein the fibrosis is cirrhosis of the liver, pulmonary fibrosis, cardiac fibrosis, mediastinal fibrosis, arthrofibrosis, myelofibrosis, nephrogenic systemic fibrosis, keloid fibrosis, scleroderma fibrosis, renal fibrosis, lymphatic tissue fibrosis, arterial fibrosis, capillary fibrosis, vascular fibrosis, or pancreatic fibrosis.

Clause 15. The method of clause 14, wherein the fibrosis is pulmonary fibrosis.

Clause 16. The method of clause 14, wherein the fibrosis is cardiac fibrosis.

Clause 17. The method of clause 16, wherein the cardiac fibrosis is caused by a) hypertrophic cardiomyopathies, sarcoidosis, chronic renal insufficiency, toxic cardiomyopathies, ischemia-reperfusion injury, acute organ rejection, chronic organ rejection, aging, chronic hypertension, non-ischemic delated cardiomyopathy, arrhythmia, atherosclerosis, HIV-associated chronic vascular disease, and pulmonary hypertension; or b) myocardial infarction or myocardial ischemia.

Clause 18. The method of clause 15, wherein the nanovesicles are administered to the patient by inhalation.

Clause 19. The method of any one of clauses 1-16, wherein the nanovesicles are administered weekly, bimonthly or monthly to the subject.

Clause 20. The method of any one of clauses 1-19, further comprising administering to the subject a therapeutically effective amount of an additional therapeutic agent.

Clause 21. The method of clause 20, wherein the additional therapeutic agent is an immunosuppressive agent.

Clause 22. The method of clause 21, wherein the immunosuppressive agent is a calcineurin inhibitor, an antiproliferative agent, an mTOR inhibitor, and/or steroids.

Clause 23. The method of clause 22, wherein the calcineurin inhibitor is tacrolimus or cyclosporine; wherein the antiproliferative agent is mycophenolate; wherein the mTOR inhibitor is sirolimus, and/or wherein the steroid is prednisone, hydrocortisone, or cortisone.

Clause 24. The method of any one of clauses 1-23, wherein the subject is a human.

Clause 25. A method for treating or inhibiting a disorder in a subject having or at risk of having the disorder. comprising: selecting a subject having or at risk of having the disorder. and administering to the subject a therapeutically effective amount of isolated nanovesicles derived from an extracellular matrix, wherein the nanovesicles contain interleukin (IL)-33 and comprise lysyl oxidase, and wherein the nanovesicles a) do not express CD63 or CD81, or b) are $CD63^{lo}CD81^{lo}$, thereby treating or inhibiting the disorder in in the subject, wherein the disorder is fibrosis of an organ or tissue.

Clause 26. The method of clause 25, wherein the extracellular matrix is a mammalian extracellular matrix.

Clause 27. The method of clause 26, wherein the mammalian extracellular matrix is a human extracellular matrix.

Clause 28. The method of any one of clauses 25-27, wherein the extracellular matrix is from esophageal tissue, urinary bladder, small intestinal submucosa, dermis, umbilical cord, pericardium, cardiac tissue, or skeletal muscle.

Clause 29. The method of any one of clauses 25-28, wherein the nanovesicles comprise miR-145 and/or miR-181.

Clause 30. The method of any one of clauses 25-29, wherein the fibrosis is cirrhosis of the liver, pulmonary fibrosis, cardiac fibrosis, mediastinal fibrosis, arthrofibrosis, myelofibrosis, nephrogenic systemic fibrosis, keloid fibrosis, scleroderma fibrosis, renal fibrosis, lymphatic tissue fibrosis, arterial fibrosis, capillary fibrosis, vascular fibrosis, or pancreatic fibrosis.

Clause 31. The method of clause 30, wherein the fibrosis is pulmonary fibrosis.

Clause 32. The method of clause 30, wherein the fibrosis is cardiac fibrosis.

Clause 33. The method of clause 32, wherein the cardiac fibrosis is caused by a) hypertrophic cardiomyopathies, sarcoidosis, chronic renal insufficiency, toxic cardiomyopathies, ischemia-reperfusion injury, acute organ rejection, chronic organ rejection, aging, chronic hypertension, non-ischemic delated cardiomyopathy, arrhythmia, atherosclerosis, HIV-associated chronic vascular disease, and pulmonary hypertension; or b) myocardial infarction or myocardial ischemia.

Clause 33.1. The method of clause 33, wherein the cardiac fibrosis is caused by acute organ rejection.

Clause 33.2. The method of clause 33, wherein the cardiac fibrosis is caused by chronic organ rejection.

Clause 34. The method of any one of clauses 25-33.2, wherein the nanovesicles are administered to the patient by inhalation or intravenously.

Clause 35. The method of any one of clauses 25-33.2, wherein the nanovesicles are administered weekly, bimonthly or monthly to the subject.

Clause 36. The method of any one of clauses 25-35, further comprising administering to the subject a therapeutically effective amount of an additional therapeutic agent.

Clause 37. The method of clause 36, wherein the additional therapeutic agent is an immunosuppressive agent.

Clause 38. The method of clause 37, wherein the immunosuppressive agent is a calcineurin inhibitor, an antiproliferative agent, an mTOR inhibitor, and/or steroids.

Clause 39. The method of clause 38, wherein the calcineurin inhibitor is tacrolimus or cyclosporine; wherein the antiproliferative agent is mycophenolate; wherein the mTOR inhibitor is sirolimus, and/or wherein the steroid is prednisone, hydrocortisone, or cortisone.

Clause 40. The method of any one of clauses 25-39, wherein the subject is a human.

Clause 41. A method for treating or inhibiting a disorder in a subject having or at risk of having the disorder, comprising: selecting a subject having or at risk of having the disorder, and administering to the subject a therapeutically effective amount of isolated nanovesicles derived from an extracellular matrix, wherein the nanovesicles contain interleukin (IL)-33 and comprise lysyl oxidase, and wherein the nanovesicles a) do not express CD63 or CD81, or b) are $CD63^{lo}CD81^{lo}$, thereby treating or inhibiting the disorder in in the subject, wherein the disorder is solid organ transplant rejection.

Clause 42. The method of clause 41, wherein the extracellular matrix is a mammalian extracellular matrix.

Clause 43. The method of clause 42, wherein the mammalian extracellular matrix is a human extracellular matrix.

Clause 44. The method of any one of clauses 41-43, wherein the extracellular matrix is from esophageal tissue, urinary bladder, small intestinal submucosa, dermis, umbilical cord, pericardium, cardiac tissue, or skeletal muscle.

Clause 45. The method of any one of clauses 41-43, wherein the nanovesicles comprise miR-145 and/or miR-181.

Clause 46. The method of any one of clauses 41-45, wherein the nanovesicles are administered to the transplanted solid organ.

Clause 47. The method of clause 46, wherein the transplanted solid organ is a heart.

Clause 47.1. The method of clause 46, wherein the transplanted solid organ is a lung, a kidney or liver.

Clause 48. The method of any one of clauses 41-47.1 wherein the nanovesicles are administered intravenously.

Clause 49: The method of any one of clauses 41-46 and 47.1, wherein the nanovesicles are administered by inhalation.

Clause 50. The method of any one of clauses 41-49, wherein the nanovesicles are administered weekly, bimonthly or monthly to the subject.

Clause 51. The method of any one of clauses 41-50, further comprising administering to the subject a therapeutically effective amount of an additional therapeutic agent.

Clause 52. The method of clause 51, wherein the additional therapeutic agent is an immunosuppressive agent.

Clause 53. The method of clause 52, wherein the immunosuppressive agent is a calcineurin inhibitor, an antiproliferative agent, an mTOR inhibitor, and/or steroids.

Clause 54. The method of clause 53, wherein the calcineurin inhibitor is tacrolimus or cyclosporine; wherein the antiproliferative agent is mycophenolate; the mTOR inhibitor is sirolimus, and/or the steroid is prednisone, hydrocortisone, or cortisone.

Clause 55. The method of any one of clauses 41-54, wherein the subject is a human.

Claus 55.1. The method of any one of clauses 41-55, wherein the solid organ transplant rejection is acute rejection.

Clause 55.2. The method of any one of clauses 41-55, wherein the solid organ transplant rejection is chronic rejection.

Clause 56. A method for treating or inhibiting a disorder in a subject having or at risk of having the disorder. comprising: selecting a subject having or at risk of having the disorder. and administering to the subject a therapeutically effective amount of isolated nanovesicles derived from an extracellular matrix, wherein the nanovesicles contain interleukin (IL)-33 and comprise lysyl oxidase, and wherein the nanovesicles a) do not express CD63 or CD81, or b) are $CD63_{lo}CD81_{lo}$, thereby treating or inhibiting the disorder in in the subject, wherein the disorder is a cardiac disease that is not myocardial infarction or myocardial ischemia.

Clause 57. The method of clause 56, wherein the extracellular matrix is a mammalian extracellular matrix.

Clause 58. The method of clause 57, wherein the mammalian extracellular matrix is a human extracellular matrix.

Clause 59. The method of any one of clauses 56-58, wherein the extracellular matrix is from esophageal tissue, urinary bladder, small intestinal submucosa, dermis, umbilical cord, pericardium, cardiac tissue, or skeletal muscle.

Clause 60. The method of any one of clauses 55-58, wherein the nanovesicles comprise miR-145 and/or miR-181.

Clause 61. The method of any one of clauses 56-60, wherein the cardiac disease is heart failure or cardiac ischemia.

Clause 62. The method of any of clauses 56-60, wherein the cardiac disease is include acute coronary syndrome, chronic stable angina pectoris, unstable angina pectoris, angioplasty, transient ischemic attack, ischemic-reperfusion injury, claudication(s), vascular occlusion(s), arteriosclerosis, heart failure, chronic heart failure, acute decompensated heart failure, cardiac hypertrophy, cardiac fibrosis, aortic valve disease, aortic or mitral valve stenosis, cardiomyopathy, atrial fibrillation, heart arrhythmia, and pericardial disease.

Clause 63. The method of any one of clauses 55-62, wherein the nanovesicles are administered intravenously.

Clause 64. The method of any one of clauses 55-62, wherein the nanovesicles are administered weekly, bimonthly or monthly to the subject.

Clause 65. The method of any one of clauses 55-64, further comprising administering to the subject a therapeutically effective amount of an additional therapeutic agent.

Clause 66. The method of any one of clauses 55-65, wherein the subject is a human.

Clause 66.1. the method of any one of clauses 55-66, wherein the cardiac disorder is heart failure.

Clause 66.2. The method of any one of clauses 55-66, wherein the cardiac disorder is cardiomyopathy.

Clause 66.3. The method of any one of clauses 55-66, wherein the cardiac disorder is ischemic-reperfusion injury.

Clause 67. A composition for use in treating or inhibiting a disorder in a subject, wherein the composition comprises a therapeutically effective amount of isolated nanovesicles derived from an extracellular matrix, wherein the nanovesicles contain interleukin (IL)-33 and comprise lysyl oxidase, and wherein the nanovesicles a) do not express CD63 or CD81, or b) are $CD63_{lo}CD81_{lo}$, and wherein the disorder is a) fibrosis of an organ or tissue b) solid organ transplant rejection; or c) a cardiac disease that is not myocardial infarction.

Clause 68. The composition of clause 67, wherein the extracellular matrix is a mammalian extracellular matrix.

Clause 69. The composition of clause 67, wherein the mammalian extracellular matrix is a human extracellular matrix.

Clause 70. The composition of any one of clauses 67-69, wherein the extracellular matrix is from esophageal tissue, urinary bladder, small intestinal submucosa, dermis, umbilical cord, pericardium, cardiac tissue, or skeletal muscle.

Clause 71. The composition of any one of clauses 67-70, wherein the nanovesicles comprise miR-145 and/or miR-181.

Clause 72. The composition of any one of clauses 67-71, wherein the disorder is the solid organ transplant rejection, and wherein the subject is a recipient of a transplanted solid organ.

Clause 73. The composition of clause 70, wherein the nanovesicles are formulated for administration to the transplanted solid organ.

Clause 74. The composition of clause 73, wherein the transplanted solid organ is a heart.

Clause 75. The composition of any one of clauses 65-71, wherein the disorder is the cardiac disease.

Clause 76. The composition of clause 75, wherein the cardiac disease is heart failure or cardiac ischemia.

Clause 77. The composition of clause 75, wherein the cardiac disease is include acute coronary syndrome, chronic stable angina pectoris, unstable angina pectoris, angioplasty, transient ischemic attack, ischemic-reperfusion injury, claudication(s), vascular occlusion(s), arteriosclerosis, heart failure, chronic heart failure, acute decompensated heart failure, cardiac hypertrophy, cardiac fibrosis, aortic valve disease, aortic or mitral valve stenosis, cardiomyopathy, atrial fibrillation, heart arrhythmia, and pericardial disease Clause 78. The composition of any one of clauses 67-77, wherein the nanovesicles are formulated for intravenous administration.

Clause 79. The composition of any one of clauses 67-71, wherein the disorder is the fibrosis of an organ or tissue.

Clause 80. The composition of clause 79, wherein the fibrosis is cirrhosis of the liver, pulmonary fibrosis, cardiac fibrosis, mediastinal fibrosis, arthrofibrosis, myelofibrosis, nephrogenic systemic fibrosis, keloid fibrosis, scleroderma fibrosis, renal fibrosis, lymphatic tissue fibrosis, arterial fibrosis, capillary fibrosis, vascular fibrosis, or pancreatic fibrosis.

Clause 81. The composition of clause 80, wherein the fibrosis is pulmonary fibrosis.

Clause 82. The composition of clause 80, wherein the fibrosis is cardiac fibrosis.

Clause 83. The composition of clause 82, wherein the cardiac fibrosis is caused by a) hypertrophic cardiomyopathies, sarcoidosis, chronic renal insufficiency, toxic cardiomyopathies, ischemia-reperfusion injury, acute organ rejection, chronic organ rejection, aging, chronic hypertension, non-ischemic delated cardiomyopathy, arrhythmia, atherosclerosis, HIV-associated chronic vascular disease, and pulmonary hypertension; or b) myocardial infarction or myocardial ischemia.

Clause 83. The composition of any one of clauses 67-81, wherein the nanovesicles are administered to the patient by inhalation.

Clause 84. The composition of any one of clauses 67-83, wherein the nanovesicles are administered weekly, bimonthly or monthly to the subject.

Clause 85. The composition of any one of clauses 67-84 further comprising a therapeutically effective amount of an additional therapeutic agent.

Clause 86. The composition of clause 85, wherein the additional therapeutic agent is an immunosuppressive agent.

Clause 87. The composition of clause 86, wherein the immunosuppressive agent is a calcineurin inhibitor, an anti-proliferative agent, an mTOR inhibitor, and/or steroids.

Clause 88. The composition of clause 87, wherein the calcineurin inhibitor is tacrolimus or cyclosporine; wherein the antiproliferative agent is mycophenolate; the mTOR inhibitor is sirolimus, and/or the steroid is prednisone, hydrocortisone, or cortisone.

Clause 89. The composition of any one of clauses 67-88, wherein the subject is a human.

Clause 90. A method for increasing myoblast differentiation, comprising:

contacting a myoblast with an effective amount of isolated nanovesicles derived from an extracellular matrix, wherein the nanovesicles contain interleukin (IL)-33 and comprise lysyl oxidase, and wherein the nanovesicles a) do not express CD63 or CD81, or b) are $CD63^{lo}CD81^{lo}$, thereby increasing myoblast differentiation.

Clause 91. The method of clause 90, wherein the myoblast is in vitro.

Clause 92. The method of clause 90 or clause 91, wherein the extracellular matrix is a mammalian extracellular matrix.

Clause 93. The method of clause 92, wherein the mammalian extracellular matrix is a human extracellular matrix.

Clause 94. The method of any one of clauses 90-93, wherein the extracellular matrix is from esophageal tissue, urinary bladder, small intestinal submucosa, dermis, umbilical cord, pericardium, cardiac tissue, or skeletal muscle.

Clause 95. The method of any one of clauses 90-94, wherein the nanovesicles comprise miR-145 and/or miR-181.

Clause 96. The method of any one of clauses 90-95, wherein the myoblast is in a mammalian subject.

Clause 97. The method of clause 96, wherein the mammalian subject is a human.

Clause 98. A method for treating or inhibiting a disorder in a subject having or at risk of having the disorder, comprising: selecting a subject having or aL risk of having the disorder, and administering to the subject a therapeutically effective amount of isolated nanovesicles derived from an extracellular matrix, wherein the nanovesicles contain interleukin (IL)-33 and comprise lysyl oxidase, and wherein the nanovesicles a) do not express CD63 or CD81, or b) are $CD63_{lo}CD81_{lo}$, thereby treating or inhibiting the disorder in in the subject, wherein the disorder is myocardial infarction or myocardial ischemia.

Clause 99. The method of clause 98, wherein the extracellular matrix is a mammalian extracellular matrix.

Clause 100. The method of clause 99, wherein the mammalian extracellular matrix is a human extracellular matrix.

Clause 101. The method of any one of clauses 98-100, wherein the extracellular matrix is from esophageal tissue, urinary bladder, small intestinal submucosa, dermis, umbilical cord, pericardium, cardiac tissue, or skeletal muscle.

Clause 102. The method of any one of clauses 98-101, wherein the nanovesicles comprise miR-145 and/or miR-181.

Clause 103. The method of any one of clauses 98-102, wherein the disorder is myocardial ischemia.

Clause 104. The method of any of clauses 98-102, wherein the disorder is myocardial infarction.

Clause 105. The method of any one of clauses 98-104, wherein the nanovesicles are administered intravenously.

Clause 106. The method of any one of clauses 98-105, wherein the nanovesicles are administered weekly, bimonthly or monthly to the subject.

Clause 107. The method of any one of clauses 98-106, further comprising administering to the subject a therapeutically effective amount of an additional therapeutic agent.

Clause 108. The method of any one of clauses 98-107, wherein the subject is a human.

The disclosure is illustrated by the following non-limiting Examples.

EXAMPLES

Myocardial ischemia causes fibrosis after damaged cardiac myocytes are replaced by fibroblasts and associated excessive extracellular matrix (ECM), which leads to increased myocardial stiffness and heart failure. Fibrosis also contributes to chronic heart allograft rejection, which causes the loss of >50% of grafts within 11 years post-transplant (Tx). There are no available therapeutic modalities to prevent or reverse fibrosis after cardiac injury.

Immunosuppressants are ineffective against the pathogenic remodeling processes that result in allograft fibrosis. IL-33 is an IL-1 family member that is typically found in the nucleus of stromal cells and generally regarded as an alarmin, or a self-derived molecule that is released after tissue damage to activate immune cells via the IL-33 receptor, ST2. Emerging evidence indicates that IL33 promotes cardiovascular and skeletal muscle repair by stimulating ST2+regulatory T cells (Treg). However, previously described methods of using IL-33 to promote tissue repair rely solely on the use of soluble IL-33 cytokine, which may have off target effects given the numerous cells expressing ST2. A need remains for new methods for delivering IL-33, and for new treatment methods for a variety of conditions in which IL-33 play a role, such as, but not limited to, cardiac disease.

ECM-scaffolds are FDA approved for numerous clinical applications including cardiac repair. Although a Phase I study investigating the use of an intracardiac injection of ECM hydrogel following myocardial infarction is currently in progress, the mechanisms by which ECM directs cardiac tissue remodeling are only partially understood. It is disclosed herein that matrix bound nanovesicles (MBV) embedded within ECM-scaffolds are a rich source of extra-nuclear interleukin-33 (IL-33). bIL-33 is typically found in the nucleus of stromal cells and generally regarded as an alarmin to alert the immune system to cell injury, resulting in production of pro-inflammatory mediators involving the IL-33 receptor, ST2. Evidence suggests that IL-33 can function as a promoter of tissue repair especially in models of cardiovascular disease where IL-33 induction following cardiac stress has been correlated with improved outcomes. It was determined that IL-33 is stably stored within ECM and protected from inactivation by incorporation into MBV. Results show that MBV from $IL33^{+/+}$, but not $IL33^{-/-}$ mouse tissues, directs $S72^{-/-}$ macrophage differentiation into the reparative, pro-remodeling M2 phenotype, and further suggest that MBV-associated IL-33 modulates macrophage activation through a non-canonical ST2-independent pathway. bThe discovery of IL-33 as an integral component of ECM-MBV provides mechanistic insights into the regulation of immune-driven pathological fibrosis. ECM-scaffolds can be used for cardiac repair.

Example 1

Matrix-Bound Nanovesides Isolated from ECM Bioscaffolds Contain Full Length IL-33

Figure 1C:
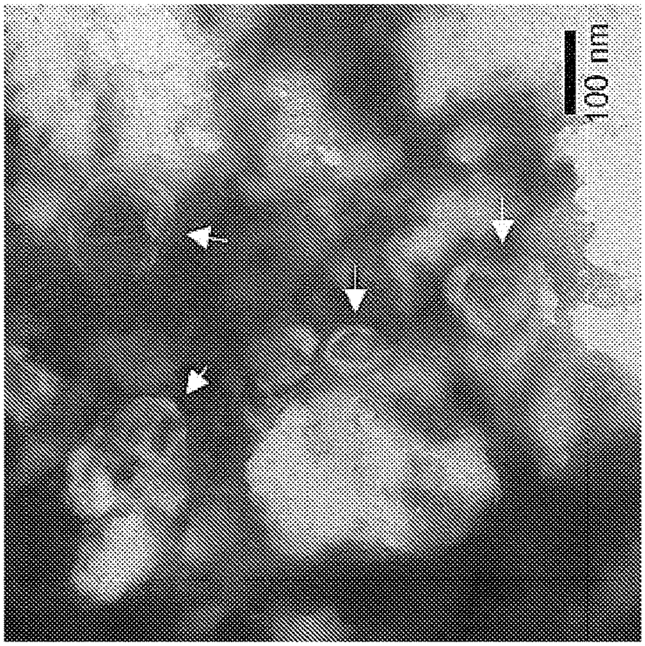
Figure 1B:
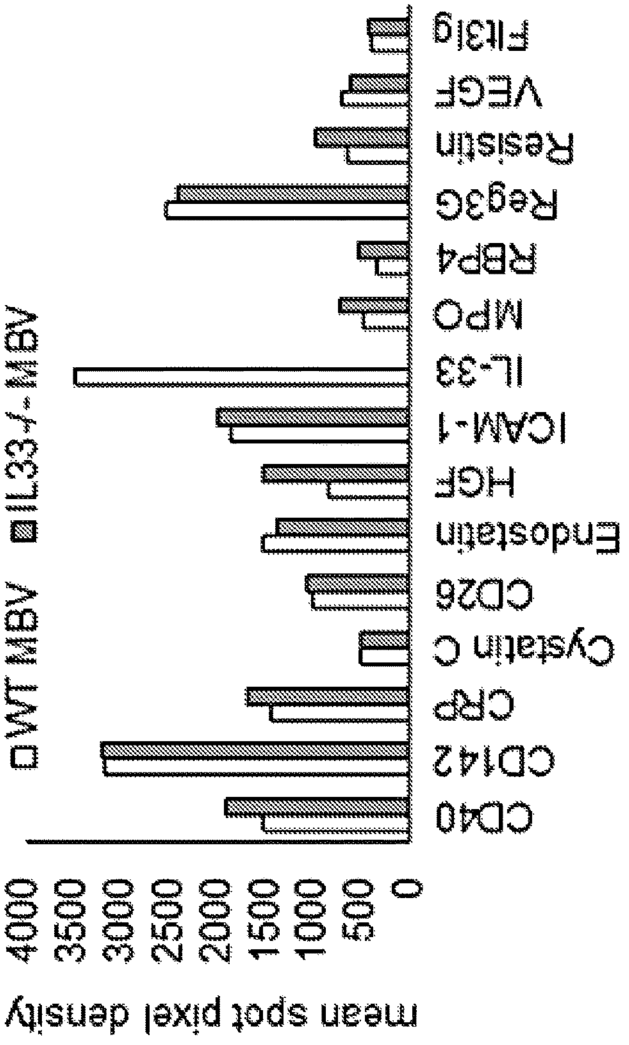
Figure 1E:
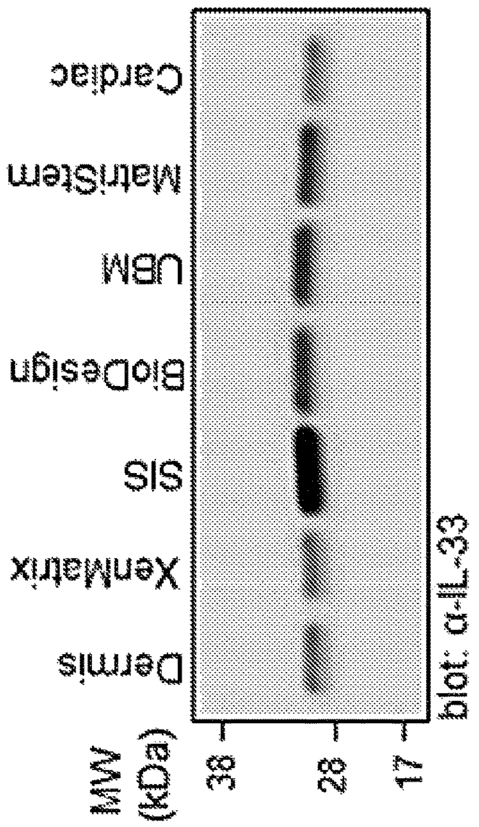
Figure 1D:
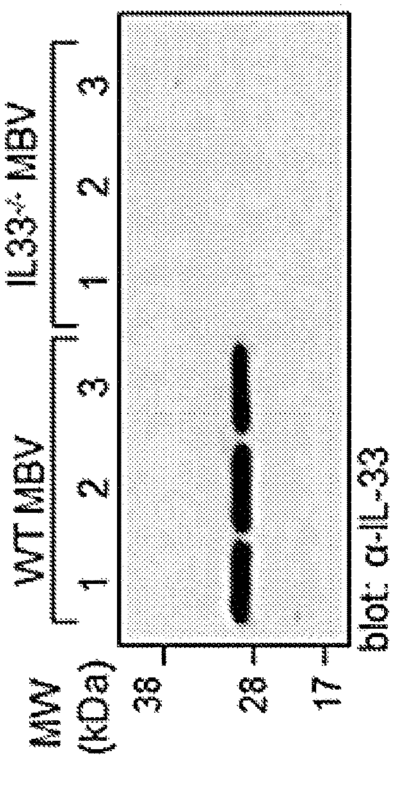

The isolation of MBV from ECM bioscaffolds and characterization of the miRNA cargo has been previously described (Huleihel et al., *Sci Adv* 2, e1600502 (2016); Huleihel et al., *Tissue Eng Part A* 23, 1283-1294 (2017)). To identify protein signaling molecules associated with MBV, a preliminary cytokine, chemokine, and growth factor screen was performed with MBV isolated from decellularized wild type (wt) mouse small intestine or decellularized $il33^{-/-}$ mouse small intestine using the Mouse XL Cytokine Array Kit from R&D system (FIG. 1A). Quantitation of proteins with the highest expression levels in MBV showed that IL-33 was highly expressed in MBV isolated from wt mice ($IL33^{+}$ MBV) compared to MBV isolated form $il33^{-/-}$ mice ($IL33^{-}$ MBV), with minimal differences in the expression of the other proteins present in isolated MBV (FIG. 1B). In addition, transmission electron microscopy imaging of MBV isolated from decellularized WT mouse intestine showed that these vesicles were approximately 100 nm in diameter (FIG. 1C). The results from the cytokine screen were furthered validated by immunoblot analysis which showed that IL-33 associated with MBV was the full-length (32 kDa) form of the protein (FIG. 1D) and not smaller described cleavage products (Lefrangais et al., *Proceedings of the National Academy of Sciences* 109, 1673-1678 (2012); Cayrol et al., *Nature immunology* 19, 375 (2018)). The presence of full-length IL-33 expression in MBV was subsequently observed in ECM surgical meshes commonly used in clinical applications, which included laboratory-produced and commercially available equivalents of urinary bladder matrix (UBM) and ACELL® MATRISTEM™; small intestinal submucosa (SIS) and Cook Biotech® BIODESIGN™; dermis and BD® XENMATRIX™; and cardiac ECM (FIG. 1E). Results showed that laboratory-produced scaffolds had similar IL-33 expression levels relative to their respective commercially available counterparts, indicating that these results were not an artifact of laboratory manufacturing protocols.

Example 2

Figure 2A:
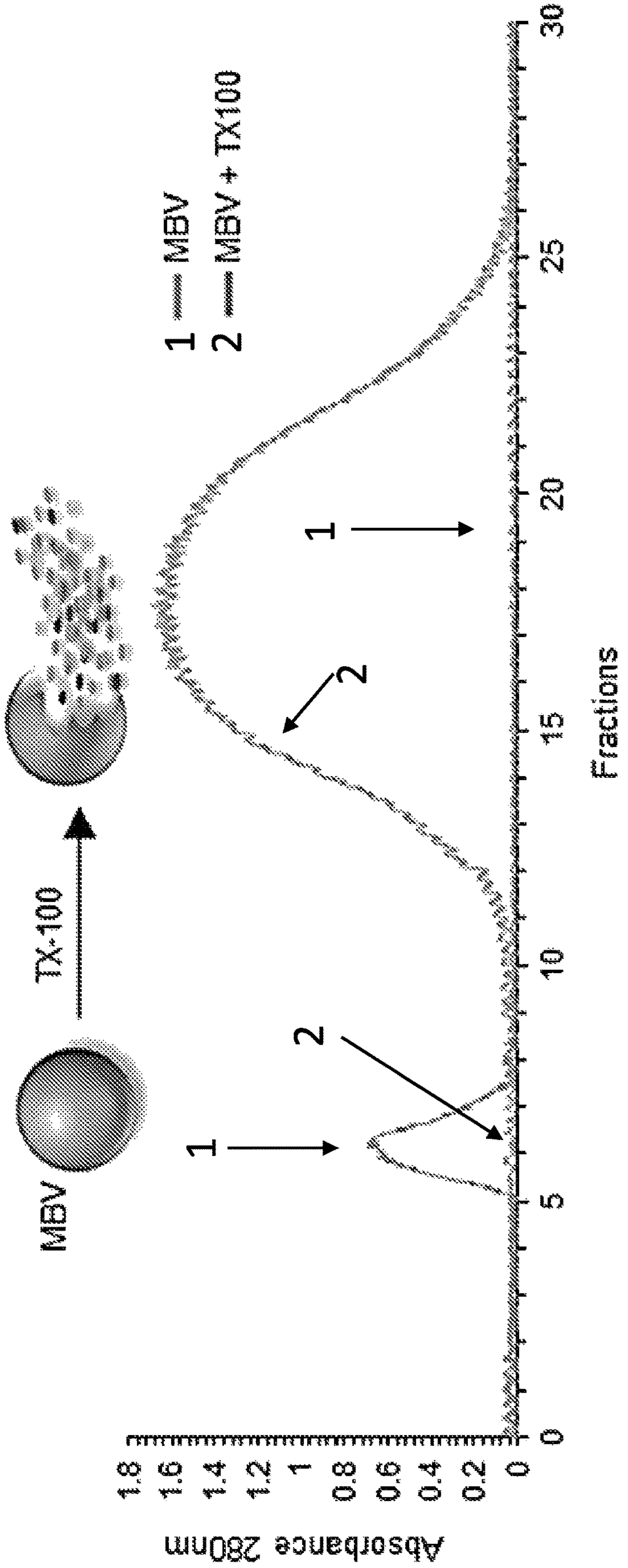
Figure 2B:
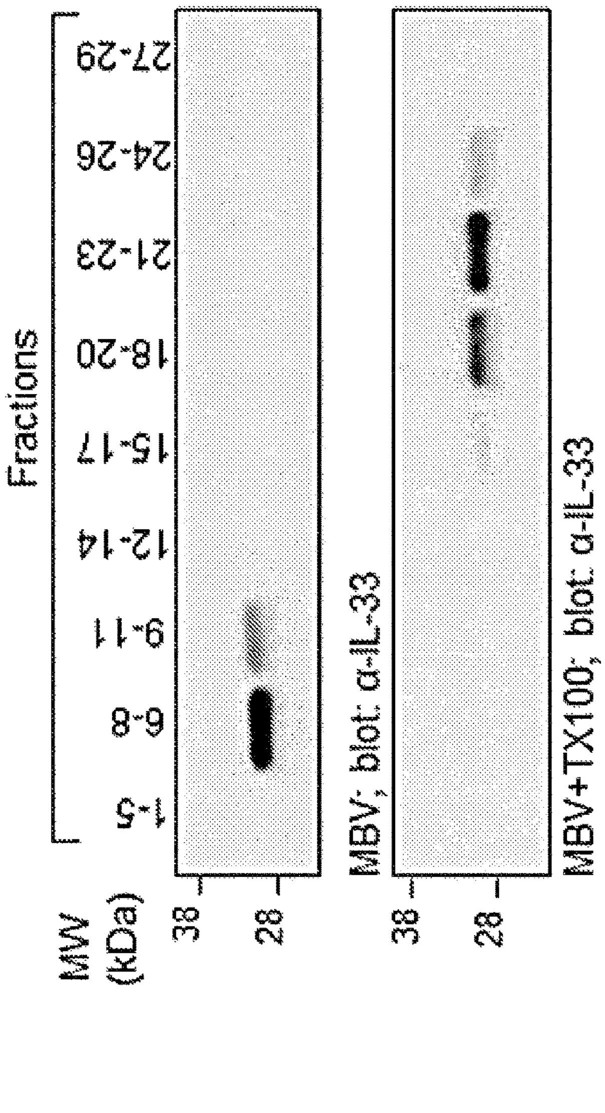
Figure 2C:
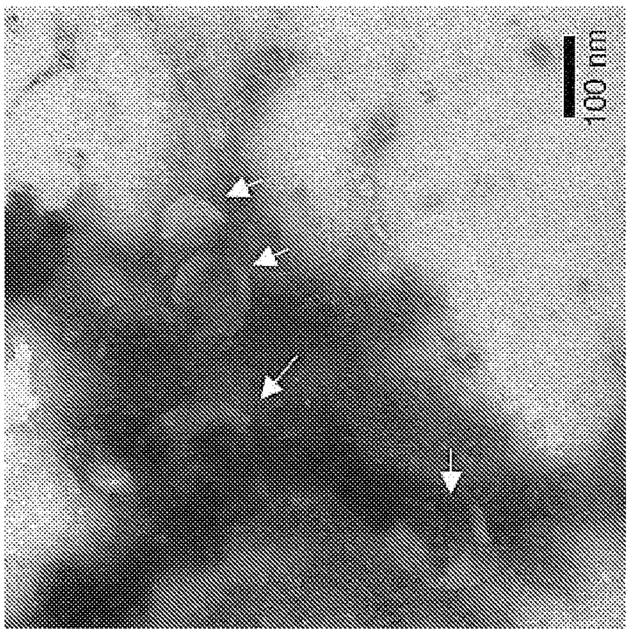
Figure 2D:
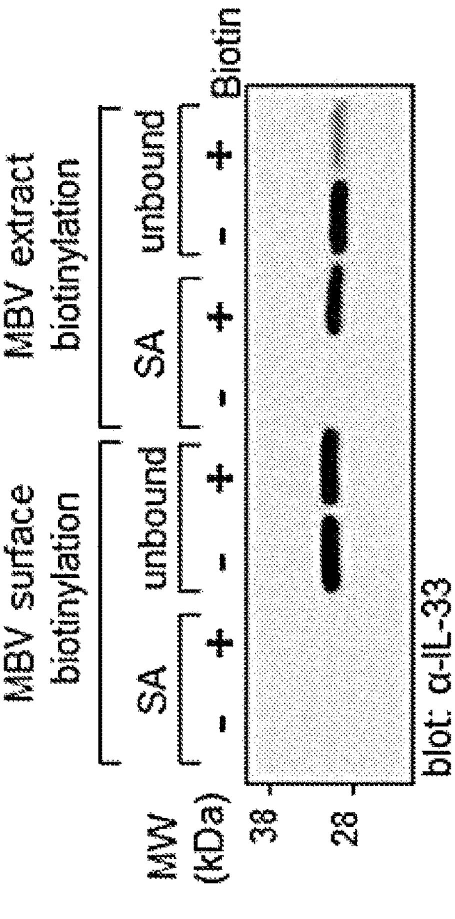
Figure 2E:
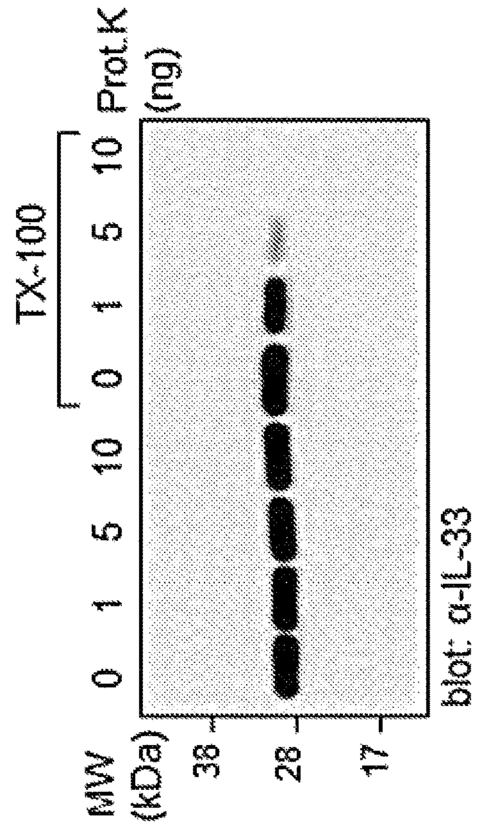

IL-33 is Stored within the Lumen of MBV and Protected from Proteolytic Degradation To verify that detected IL-33 was not a contaminant of the MBV isolation process, MBV were further purified by size exclusion chromatography (SEC) using a SEPHAROSE® CL-2B resin with continuous monitoring of eluted fractions by UV absorbance at 280 nm (FIG. 2A). Immunoblot analysis confirmed the presence of IL-33 in the heavy MBV fractions (FIG. 2B, top panel). In a separate experiment, MBV were first lysed with 1% TRITON® X-100 and the extracts then analyzed by SEC. Results show that the molecular components from lysed MBV eluted primarily in the lighter fractions as determined by the shift in the UV chromatogram (FIG. 2A), and immunoblot analysis (FIG. 2B, bottom panel). In addition, transmission electron microscopy of pooled fractions 6-8 showed the presence of vesicles in these fractions (FIG. 2C). These results confirmed that IL-33 was associated with the MBV, and not a soluble contaminant of the MBV isolates. It was next determined if IL-33 was present on the surface membrane of MBV or stored within the lumen. MBV pooled from fractions 6-8 were biotinylated with NHS-LC-Biotin. The sulfonate group prevents the biotin from permeating the lipid membrane, thereby labeling only the outer surface proteins (Diaz et al., *Scientific reports* 6, 37975 (2016)). After biotinylation, MBV were lysed and subjected to a streptavidin pull down assay to fractionate the surface proteins from the unbound luminal components. Immunoblot analysis showed that IL-33 was present only in the unbound fraction and was not pulled down by the streptavidin (SA) beads (FIG. 2D). In a separate experiment, MBV were first lysed with 1% TRITON® X-100 and then subjected to biotinylation. This allowed for biotinylation of both the surface and luminal components of MBV. Immunoblot analysis showed that following streptavidin pull down, IL-33 was associated with the SA beads (FIG. 2D). Cumulatively, these data suggested that IL-33 was stored within the lumen of MBV. To confirm these results, a proteinase K protection assay was performed. MBV from pooled fractions 6-8 were incubated with increasing concentrations of proteinase K for 30 min at 37° C. in the absence or presence of 1% TRITON® X-100. As shown by immunoblot analysis (FIG. 2E), in the absence of TRITON® X-100, IL-33 was not degraded by Proteinase K. Permeabilization of the MBV membrane by TRITON® X-100, however, makes IL-33 accessible and susceptible to proteinase K, resulting in its degradation (FIG. 2E). These results confirmed that MBV-associated IL-33 is present in the lumen of the vesicle membrane where it is protected from proteolytic degradation.

Example 3

Figure 3A:
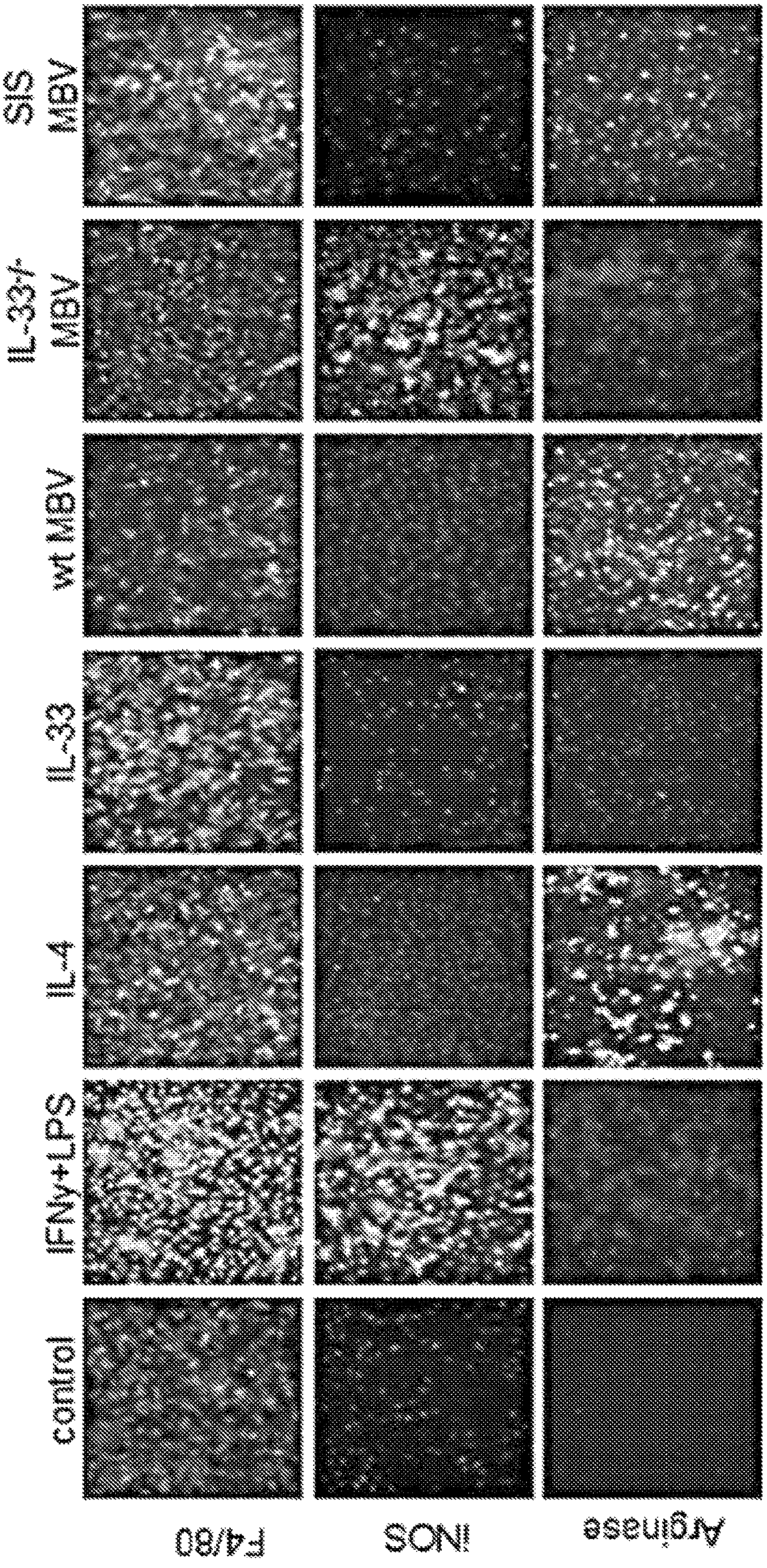
Figure 3B:
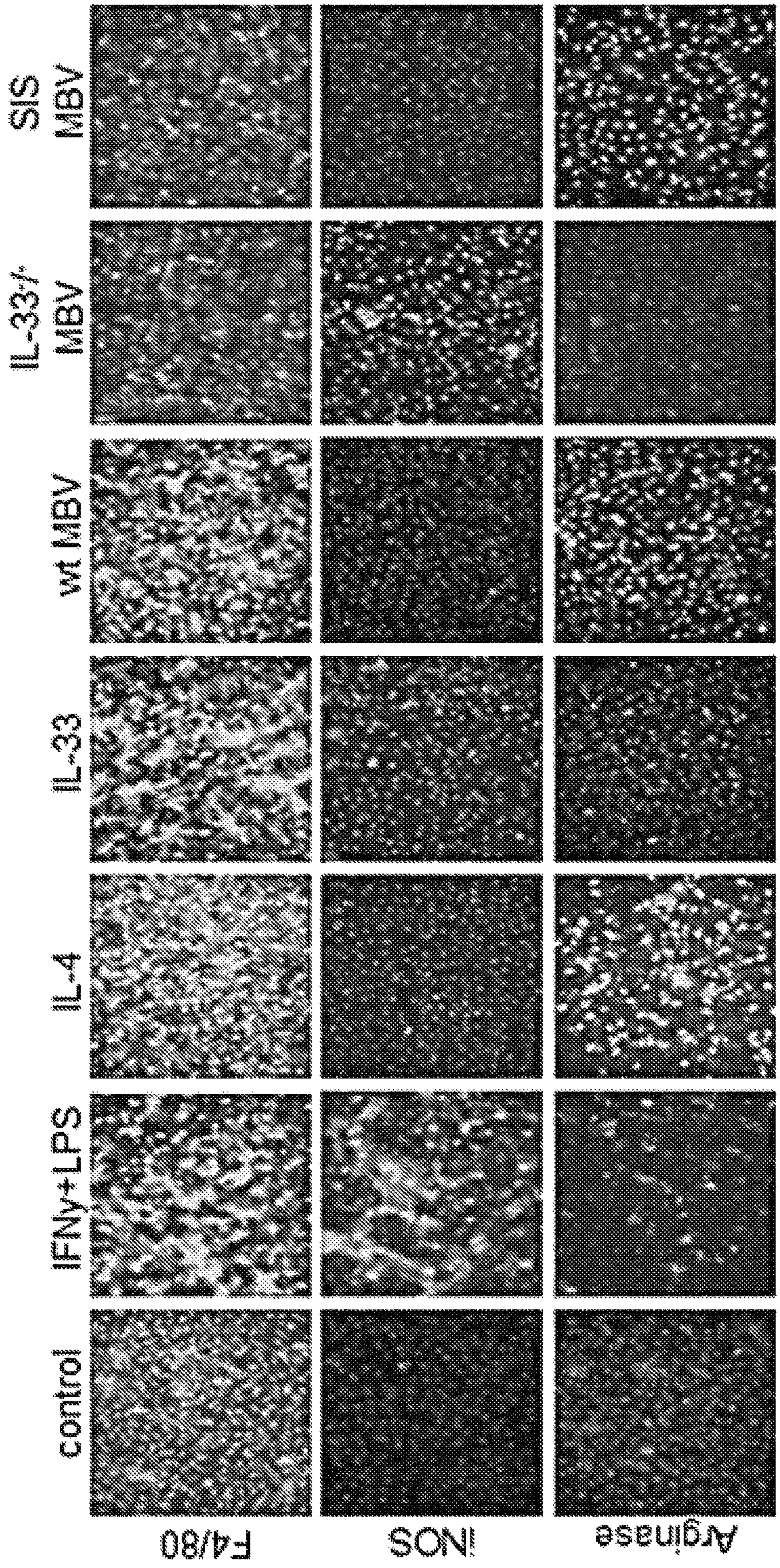
Figure 3D:
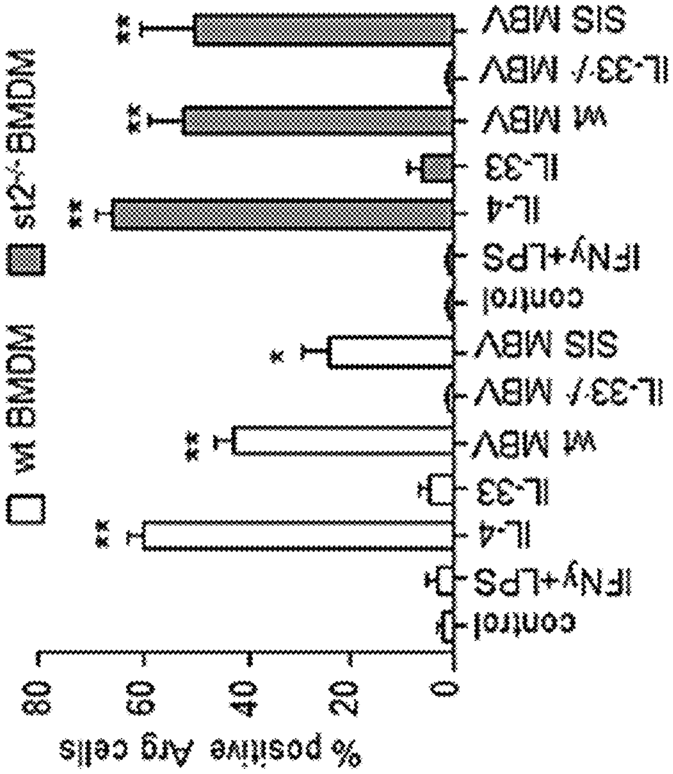
Figure 3C:
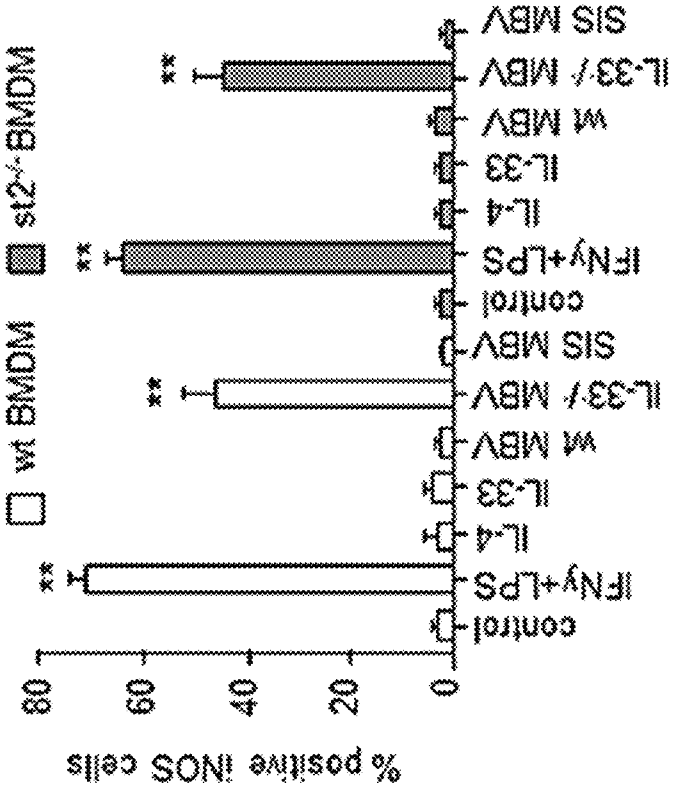

$IL33^+$ MBV Activate a Pro-Remodeling Macrophage Phenotype Via a Non-Canonical ST2-Independent Pathway An extensive mechanistic examination of the impact of $IL\text{-}33^+$ or $IL\text{-}33^-$ MBV on myeloid cells was conducted in-vitro. Given the location of IL-33 within the lumen of MBV, it was hypothesized that encapsulation of IL-33 prevents binding to its cognate ST2 receptor, suggesting the presence of an ST2-independent transduction mechanism. To investigate this scenario, bone marrow-derived macrophages (BMDM) isolated from B6 wt (FIG. 3A) or $st2^{-/-}$ mice (FIG. 3B) were stimulated with interferon-γ (IFN-γ) and lipopolysaccharide (LPS) to induce an MI-like macrophage phenotype, interleukin-4 (IL-4) to induce an M2-like phenotype, recombinant IL-33, MBV isolated from decellularized wt ($IL33^+$ MBV) or $il33^{-/-}$ ($IL33^-$ MBV) mouse intestine, or MBV isolated from porcine small intestinal submucosa (SIS MBV). Results showed that macrophages expressed Arginase 1 (Arg-1) in response to SIS MBV and $IL33^+$ MBV, similar to the expression pattern of the IL-4-stimulated (M2) cells (FIGS. 3 A, 3D). In contrast, $IL33^-$ MBV induced the expression of iNOS but not Arg-1 (FIGS. 3 A, 3C). A similar effect was observed with macrophages isolated from $st2^{-/-}$ mice. Specifically, $IL33^+$ MBV, but not $IL33^-$ MBV, directed $st2^{-/-}$ macrophage activation into the reparative, pro-remodeling M2-like phenotype (FIGS. 3B, 3C, 3D). Results from the immunolabeling assay were subsequently confirmed by Western blot analysis which showed that stimulation of macrophages with $IL33^+$ MBV, but not $IL33^-$ MBV, could induce the upregulation of Arg-1 expression (FIG. 4A). In addition, this capacity of IL33+ MBV to induce Arg-1 expression was shown to be distinct from the well characterized IL-4/IL-13-mediated M2 macrophage differentiation pathway, as $IL33^+$ MBV activate M2 macrophages independently of STAT6 phosphorylation (FIG. 4B). These data demonstrate that MBV-associated IL-33 modulates macrophage activation through an uncharacterized, non-canonical ST2-independent pathway.

Example 4

Evaluation of Myogenesis of Skeletal Muscle Progenitor Cells Following Exposure to Macrophage Secreted Products It has been shown that the secretome associated with alternatively activated M2 macrophages is myogenic for skeletal muscle myoblasts[41,42]. Previously, we have shown that media conditioned by ECM-treated macrophages promoted myotube formation and sarcomeric myosin expression of $C_2C_{12}$ myoblasts[43]. The present study shows similar results in that media conditioned by macrophages stimulated with IL33+MBV, but not $IL33^-$ MBV, promoted myotube formation of $C_2C_{12}$ myoblasts similar to the biologic activity to IL-4-induced M2-like macrophages (FIGS. 5A, B).

Example 5

Materials and Methods for Examples 1-4

Decellularization of mouse intestines: Fresh small intestines were obtained from adult wild-type (wt) B6 mice or adult IL-33' B6 mice. Small intestines were washed in phosphate buffered saline (PBS) to completely remove all the intestinal contents, and 1.5 cm-length fragments were obtained from each intestine for immediate decellularization. Samples were decellularized as previously described (Oliveira A C, et al. *PLoS ONE.* 2013; 8(6):e66538). Briefly, samples were first immersed in 5M NaCl for 72 h under continuous soft agitation. The decellularization solution was replaced every 24 h. Mouse intestine ECM was then lyophilized and milled into particulate using a Wiley Mill with a #40 mesh screen.

Preparation of Dermal ECM: Dermal ECM was prepared as previously described (Reing J E, et al. *Biomaterials.* 2010; 31(33):8626-33). Briefly, full-thickness skin was harvested from market-weight (~10 kg) pigs (Tissue Source Inc.), and the subcutaneous fat and epidermis were removed by mechanical delamination. This tissue was then treated with 0.25% trypsin (Thermo Fisher Scientific) for 6 hours, 70% ethanol for 10 hours, 3% $H_2O_2$ for 15 min, 1% TRITON® X-100 (Sigma-Aldrich) in 0.26% EDTA/0.69% tris for 6 hours with a solution change for an additional 16 hours, and 0.1% peracetic acid/4% ethanol (Rochester Midland) for 2 hours. Water washes were performed between each chemical change with alternating water and phosphate-buffered saline (PBS) washes following the final step. All chemical exposures were conducted under agitation on an orbital shaker at 300 rpm. Dermal ECM was then lyophilized and milled into particulate using a Wiley Mill with a #40 mesh screen.

Preparation of urinary bladder matrix (UBM): UBM was prepared as previously described (Mase V J, et al. *Orthopedics.* 2010; 33(7):511). Porcine urinary bladders from market-weight animals were acquired from Tissue Source, LLC. Briefly, the tunica serosa, tunica muscularis externa, tunica submucosa, and tunica muscularis mucosa were mechanically removed. The luminal urothelial cells of the tunica mucosa were dissociated from the basement membrane by washing with deionized water. The remaining tissue consisted of basement membrane and subjacent lamina propria of the tunica mucosa and was decellularized by agitation in 0.1% peracetic acid with 4% ethanol for 2 hours at 300 rpm. The tissue was then extensively rinsed with PBS and sterile water. The UBM was then lyophilized and milled into particulate using a Wiley Mill with a #60 mesh screen.

Preparation of small intestinal submucosa (SIS): SIS was prepared as previously described (Badylak S F, et al. *J Surg Res.* 1989; 47(1):74-80). Briefly, jejunum was harvested from 6-month-old market-weight (~10 to ~120 kg) pigs and split longitudinally. The superficial layers of the tunica mucosa were mechanically removed. Likewise, the tunica serosa and tunica muscularis externa were mechanically removed, leaving the tunica submucosa and basilar portions of the tunica mucosa. Decellularization and disinfection of the tissue were completed by agitation in 0.1% peracetic acid with 4% ethanol for 2 hours at 300 rpm. The tissue was then extensively rinsed with PBS and sterile water. The SIS was then lyophilized and milled into particulate using a Wiley Mill with a #60 mesh screen.

Preparation of cardiac ECM: Cardiac ECM was prepared as previously described (Wainwright J M, et al. *Tissue Eng Part C Methods.* 2010; 16(3):525-32). Briefly, porcine hearts were obtained immediately following euthanasia and frozen at −80° C. for at least 16 h and thawed. The aorta was cannulated and alternately perfused with type 1 reagent grade (type 1) water and 2×PBS at 1 liter/min for 15 min each. Serial perfusion of 0.02% trypsin/0.05% EDTA/0.05% $NaN_3$ at 37° C., 3% TRITON® X-100/0.05% EDTA/0.05% $NaN_3$, and 4% deoxycholic acid was conducted (each for 2 h at approximately 1.2 liters/min). Finally, the heart was perfused with 0.1% peracetic acid/4% EtOH at 1.7 liters/min for 1 h. After each chemical solution, type 1 water and 2×PBS were flushed through the heart to aid in cell lysis and the removal of cellular debris and chemical residues. The cardiac ECM was then lyophilized and milled into particulate using a Wiley Mill with a #60 mesh screen.

Isolation of matrix bound nanovesicles (MBV): MBV were isolated as previously described (Huleihel L et al. *Sci Adv.* 2016; 2(6): e1600502). Briefly, Enzymatically digested ECM was subjected to successive centrifugations at 500 g (10 min), 2500 g (20 min), and 10,000 g (30 min) to remove collagen fibril remnants. Each of the above centrifugation steps was performed three times. The fiber-free supernatant was then centrifuged at 100,000 g (Beckman Coulter Optima L-90K ultracentrifuge) at 4° C. for 70 min. The 100,000 g pellets were washed and suspended in 500 μl of PBS and passed through a 0.22-μm filter (Millipore).

Cytokine antibody array: Cytokines stored within MBV were analyzed using the Mouse XL Cytokine Array Kit (R&D Systems; Minneapolis, MN, USA) according the manufacturer's instructions. Extracts were prepared from MBV isolated from decellularized WT mouse intestine (n=3) or decellularized IL-$33^{-/-}$ mouse intestine (n=3). Extracts were diluted and incubated overnight with the array membrane. The array was rinsed to remove unbound protein, incubated with an antibody cocktail, and developed using streptavidin-horseradish peroxidase and chemiluminescent detection reagents. Mean spot pixel density was quantified using Image J software.

Transmission Electron Microscopy (TEM): TEM imaging was conducted on MBV loaded on carbon-coated grids and fixed in 4% paraformaldehyde as previously described (Huleihel L et al. *Sci Adv.* 2016; 2(6): e1600502). Grids were imaged at 80 kV with a JEOL 1210 TEM with a high-resolution Advanced Microscopy Techniques digital camera. Size of MBV was determined from representative images using JEOL TEM software.

Size Exclusion Chromatography (SEC): Fractionation of MBV by SEC was performed as previously described (Böing, A N, et al. *J Extracellular Vesicles.* 2014; 3(1). Briefly, 15 ml of Sepharose CL-2B resin (Sigma Aldrich) was stacked in a 1 cm×20 cm glass column and washed and equilibrated with PBS. 1 ml of MBV were loaded onto the column and fraction collection (0.3 ml per fraction and a total of 30 fractions collected) started immediately using PBS as the elution buffer. Eluted fractions were continuously monitored by UV 280 nm using the Biologic LP system (BioRad). Lysed MBV were prepared by incubating MBV in 1% TRITON® X-100 for 30 min, and then subjected to SEC as described above.

Biotinylation of MBV proteins: Biotinylation of MBV proteins was performed as previously described (Diaz G, et al. *Sci Rep.* 2016; 6: 37975) with minor modifications. One hundred micrograms of intact MBV were incubated in the absence or presence of 10 mM Sulfo-NHS-Biotin at room temperature for 30 min. The presence of the sulfonate group in Sulfo-NHS-Biotin blocks the reagent from penetrating the MBV membrane. After incubation, excess Sulfo-NHS-Biotin was removed using a 10 kDa MWCO filtration column, and MBV were then lysed with 1% TRITON® X-100. In a separate experiment, 100 micrograms of MBV were first lysed in 1% TRITON® X-100. After lysis, buffer exchange was performed to replace the 1% TRITON® X-100 solution with 1×PBS. The MBV extract was then incubated in the absence or presence of 10 mM Sulfo-NHS-Biotin at room temperature for 30 min. After incubation, excess Sulfo-NHS-Biotin was removed using a 10 kDa MWCO filtration column. MBV ±biotin or MBV extract ±biotin were diluted to 500 μl in 1×PBS and incubated with 50 μl prewashed streptavidin-sepharose resin (Sigma Aldrich). After incubation on an orbital rocker for 2 hrs at room temperature, the streptavidin-sepharose resin was pelleted by centrifugation at 10,000×g for 5 min. The supernatant representing the unbound fraction was transferred to a fresh tube, and the resin was washed 5 times in 300 mM NaCl. Bound proteins were eluted from resin by incubating with elution buffer (2% SDS, 6M Urea) for 15 minutes at room temperature and then 15 minutes at 96 C.

Proteinase K protection assay: Proteinase K protection assay was performed as previously described (de Jong O G, et al. *J Cell Mol Med.* 2016; 20(2): 342-350). Briefly, MBV were incubated in either PBS or increasing concentrations of Proteinase K in PBS, with or without the presence of 1% TRITON® X-100, in a final volume of 20 μl per sample for 1 hr at 37° C. The assay was stopped by addition of 20 μl 95° C. 2× Laemmli Buffer with 10 mM DTT. After 5 min. incubation at 95° C., samples were used for immunoblot analysis.

Isolation and activation of macrophages: Murine bone marrow-derived macrophages (BMDM) were isolated and characterized as previously described (Huleihel L et al. *Tissue Eng Part A.* 2017; 23(21-22):1283-1294). Briefly, bone marrow was harvested from 6- to 8-week-old C57bl/6 mice. Harvested cells from the bone marrow were washed and plated at $1\times10^6$ cells/mL and were allowed to differentiate into macrophages for 7 days in the presence of macrophage colony-stimulating factor (MCSF) with complete medium changes every 48 h. Macrophages were then activated for 24 h with one of the following: (1) 20 ng/mL interferon-γ (IFNγ) and 100 ng/mL lipopolysaccharide (LPS) (Affymetrix eBioscience, Santa Clara, CA; Sigma Aldrich) to promote an $M_{IFN\gamma+LPS}$ phenotype (MI-like), (2) 20 ng/mL interleukin (IL)-4 (Invitrogen) to promote an $M_{IL\text{-}4}$ phenotype (M2-like), (3) 100 ng/ml IL-33 (Peprotech), or (4) 25 μg/mL of WT mouse MBV, IL-$33^{-/-}$ MBV, or SIS-MBV. After the incubation period at 37° C., cells were washed with sterile PBS and fixed with 2% paraformaldehyde (PFA) for immunolabeling.

Macrophage immunolabeling: To prevent nonspecific binding, the cells were incubated in a blocking solution composed of PBS, 0.1% TRITON®-X, 0.1% TWEEN®-20, 4% goat serum, and 2% bovine serum albumin for 1 h at room temperature. The blocking buffer was then removed and cells were incubated in a solution of one of the following primary antibodies: (1) monoclonal anti-F4/80 (Abcam, Cambridge, MA) at 1:200 dilution as a pan-macrophage marker, (2,3) polyclonal anti-inducible nitric oxide synthase (iNOS) (Abcam, Cambridge, MA) at 1:100 dilution as an MI-like marker, and anti-Arginase1 (Abcam, Cambridge, MA) at 1:200 dilution, as an M2-like marker. The cells were incubated at 4° C. for 16 h, the primary antibody was removed, and the cells washed with PBS. A solution of fluorophore-conjugated secondary antibody (Alexa donkey anti-rabbit 488 or donkey anti-rat 488; Invitrogen, Carlsbad, CA) was added to the appropriate well for 1 h at room temperature. The antibody was then removed, the cells washed with PBS, and the nuclei were counterstained using DAPI. Cytokine-activated macrophages were used to establish standardized exposure times (positive control), which were held constant throughout groups thereafter. CellProfiler (Broad Institute, Cambridge, MA) was used to quantify images. Data were analyzed for statistical significance using either an unpaired Student's t-test, through which treated macrophages were compared to the appropriate M0 media control, or a one-way analysis of variance with Tukey's post-hoc test for multiple comparisons. Data are reported as mean t standard deviation with a minimum of N=3. p-Values of <0.05 were considered to be statistically significant.

$C_2C_{12}$ myogenesis assay: High serum media (20% fetal bovine serum) maintains cell proliferation within the cell cycle and inhibits differentiation. Conversely, low serum media (1% fetal bovine serum, 1% horse serum) induces cell-cycle exit and myotube formation providing a positive control. These are referred to as proliferation media and differentiation media, respectively. Myogenic differentiation potential was determined by examining the skeletal muscle myoblast fusion index. $C_2C_{12}$ skeletal muscle myoblasts were cultured in proliferation media until they reached approximately 80% confluence. Media was then changed to treatment media consisting of a 50:50 solution of macrophage supernatants and proliferation media, or controls of proliferation media or differentiation media. Following 5-7 days, or when differentiation media controls showed myotube formation, cells were fixed for immunolabeling with 2% paraformaldehyde. Fixed cells were blocked according to the previous described protocol for 1 h at room temperature and incubated in anti-sarcomeric myosin antibody. Following primary incubation, cells were washed with PBS and incubated in Alexa Fluor donkey anti-mouse 488 secondary antibody at a dilution of 1:200 for 1 h at room temperature and counterstained with DAPI. Images of five 20× fields were taken for each well using a Zeiss Axiovert microscope.

Example 6

IL-33 in Transplant Rejection and MBVs

Acute heart transplant (HTx) rejection is typically averted by immunosuppressant therapy, which controls recipient $CD4^+$ and $CD8^+$ T cell responses to alloantigens. However, such immunosuppressive therapy is ineffective against chronic heart transplant rejection (CR), and the resultant immune-mediated fibrotic and vascular remodeling leads to progressive myocardial dysfunction and loss of the majority of HTx within approximately 11 years post transplantation. Recent studies have shown that innate immune cells, such as inflammatory macrophages, monocytes, and monocyte-derived dendritic cells (DC), play a key role in CR due to their potent pro-inflammatory responses to damage-associated molecular patterns (DAMPs) released following ischemia reperfusion injury (IRI) associated with the transplant process. Solid organs are rapidly infiltrated with recipient monocytes and recipient monocyte-derived DC, which act as an important local stimuli to alloreactive T cells that initiate and sustain CR. Thus, it is clear that self-molecules containing damage-associated molecular patterns are release during tissue injury and stimulate pro-inflammatory response in infiltrating innate immune cells. However, local endogenous negative regulators that are also present at the site of injury to control immune responses is poorly understood. IL-33, an IL-1 family member sequestered in the nucleus of stromal cells, may have such immunoregulatory properties. Delivery of recombinant IL-33 promotes graft survival after heart transplant by expanding regulatory T cells (Treg). It is disclosed herein that discovered that MBV) isolated from the ECM of various organs are a rich and stable source of IL-33. While IL-33 was appreciated to be a nuclear protein, mechanisms releasing it from sequestration in the nucleus and allowing it mediate effects on immune cells has been lacking. The data presented herein establish that IL-33 in MBV are an important source of non-sequestered and immunoregulatory IL-33 that is able to direct innate immune cell differentiation in vitro and in vivo.

Example 7

The Absence of IL-33 Increases Chronic Rejection

Figures 6A, 6B:
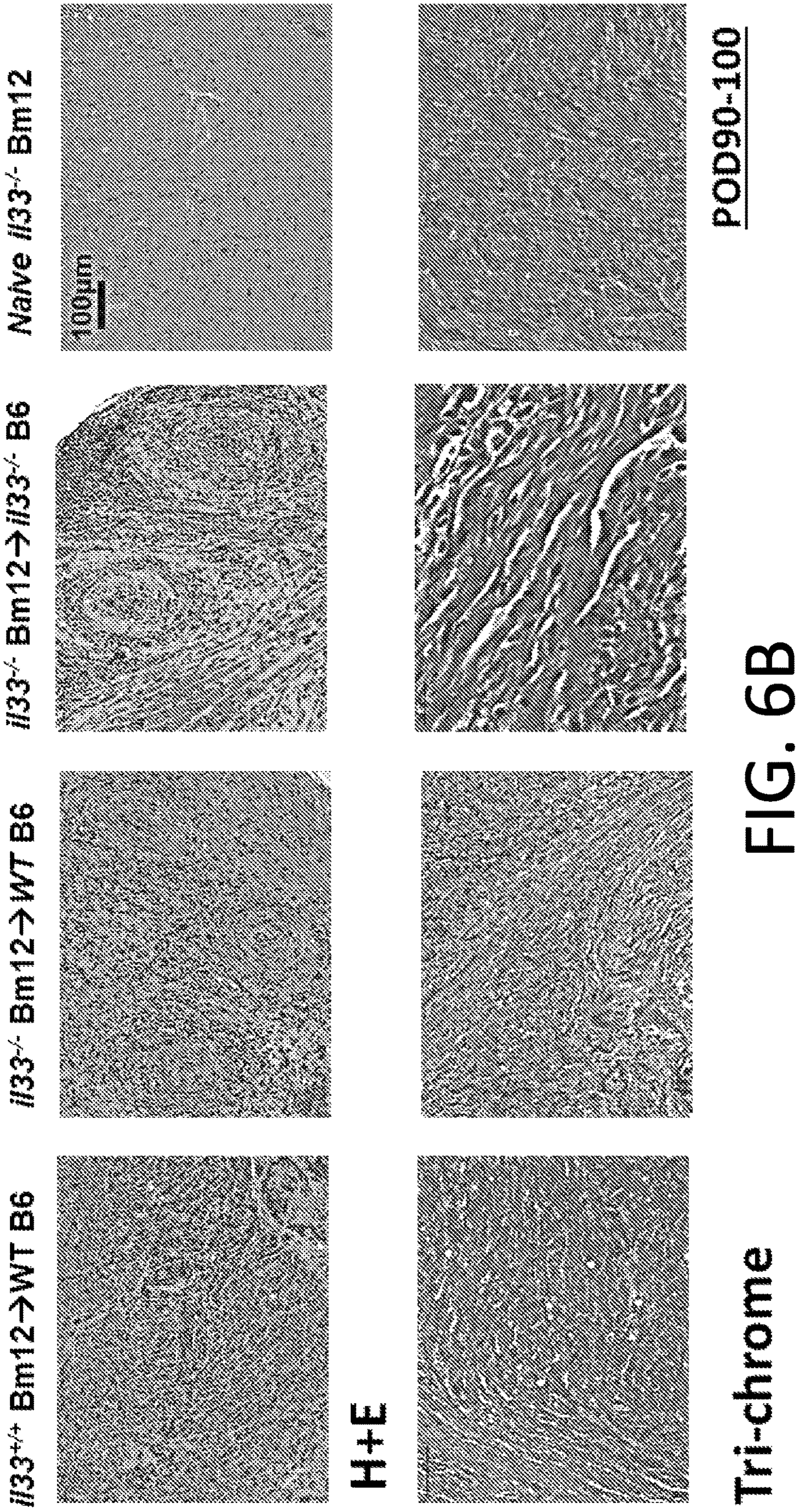
Figures 6C, 6D:
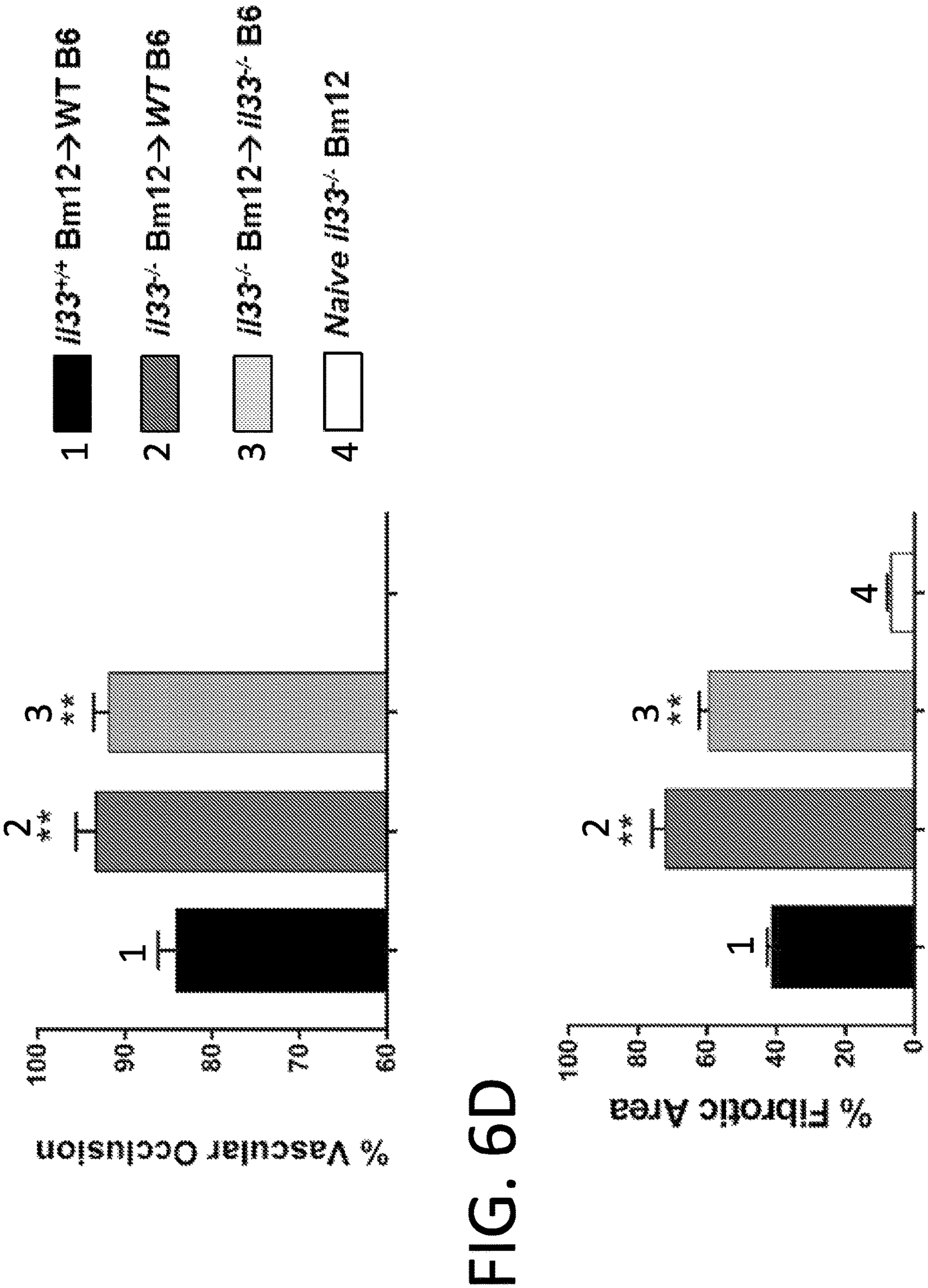
Figures 7A, 7B, 7C, 7D:
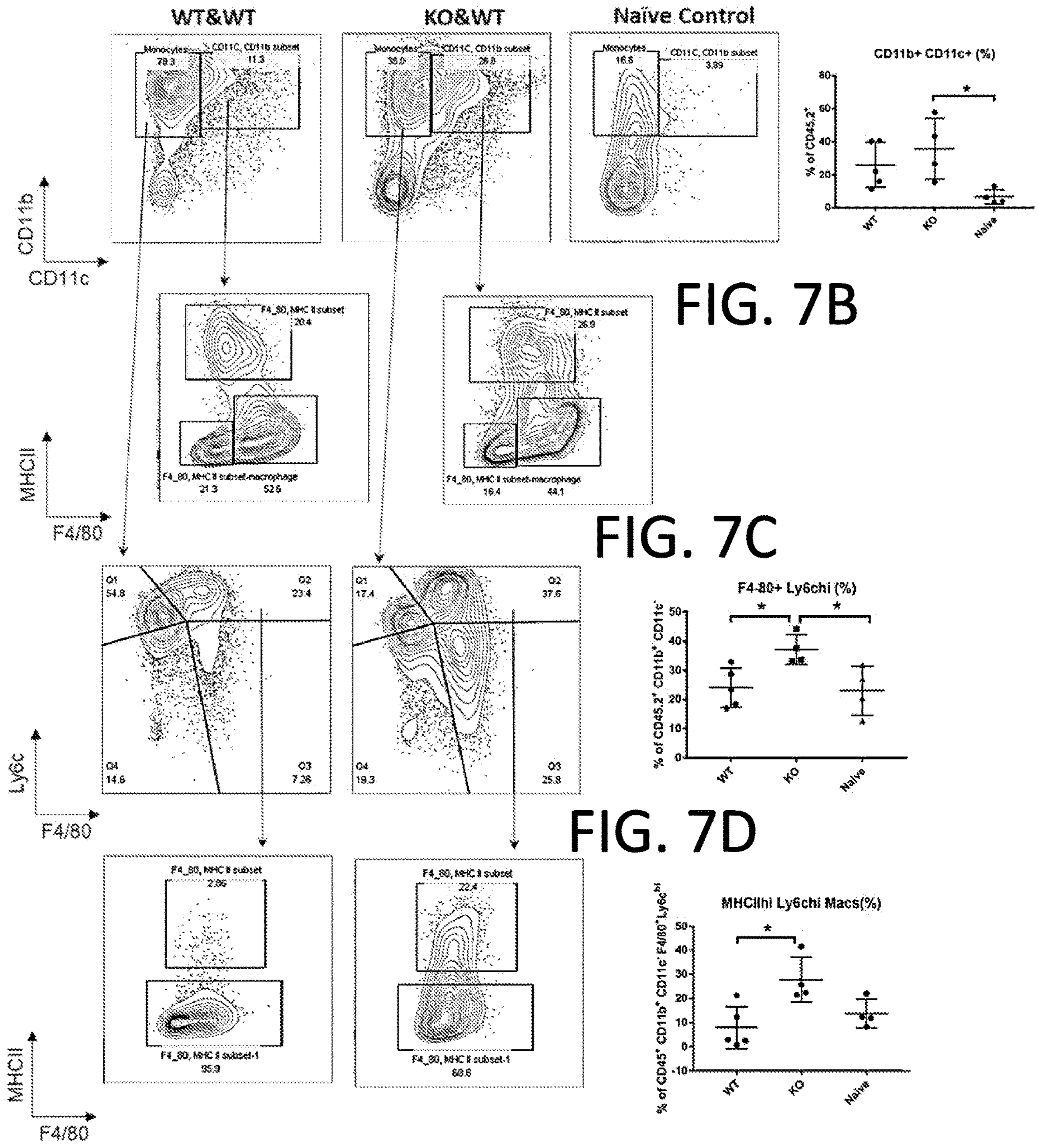
Figure 8A:
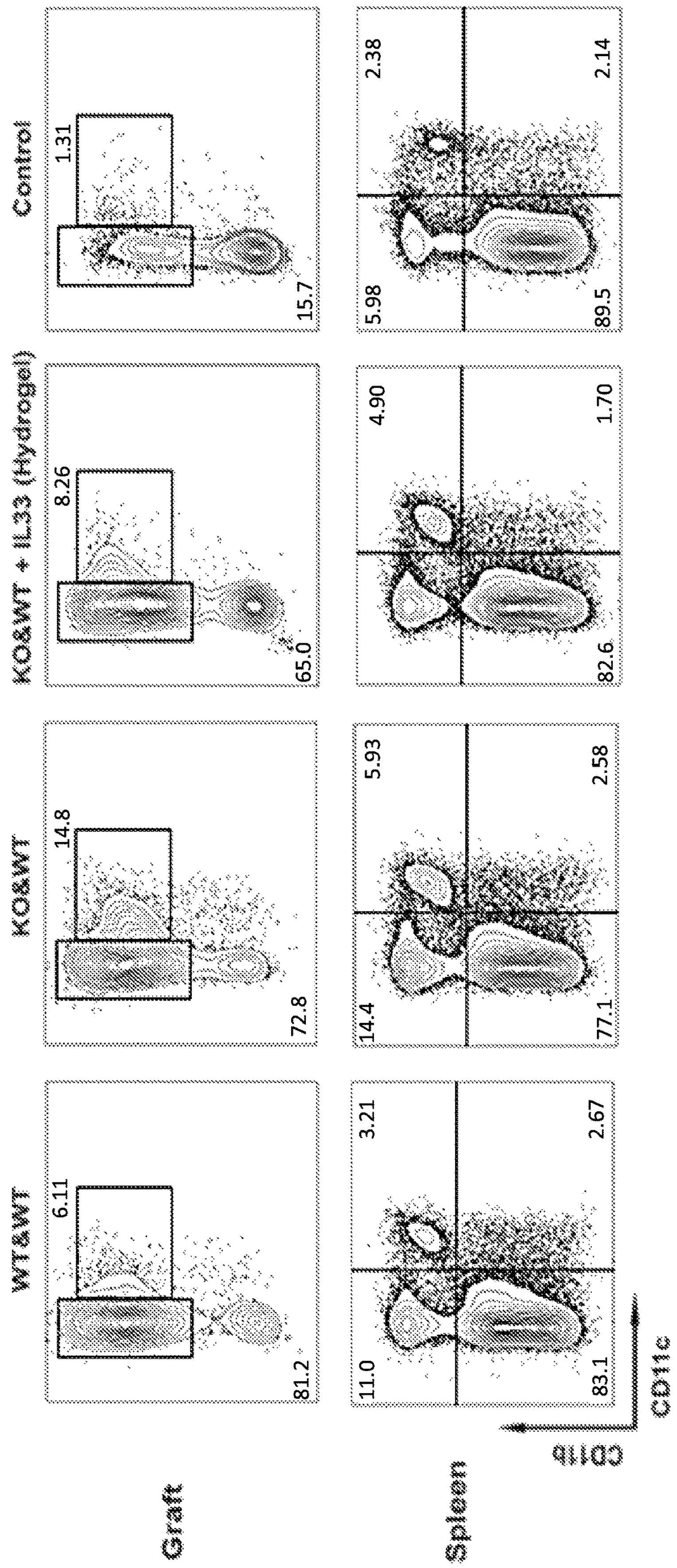
Figure 8B:
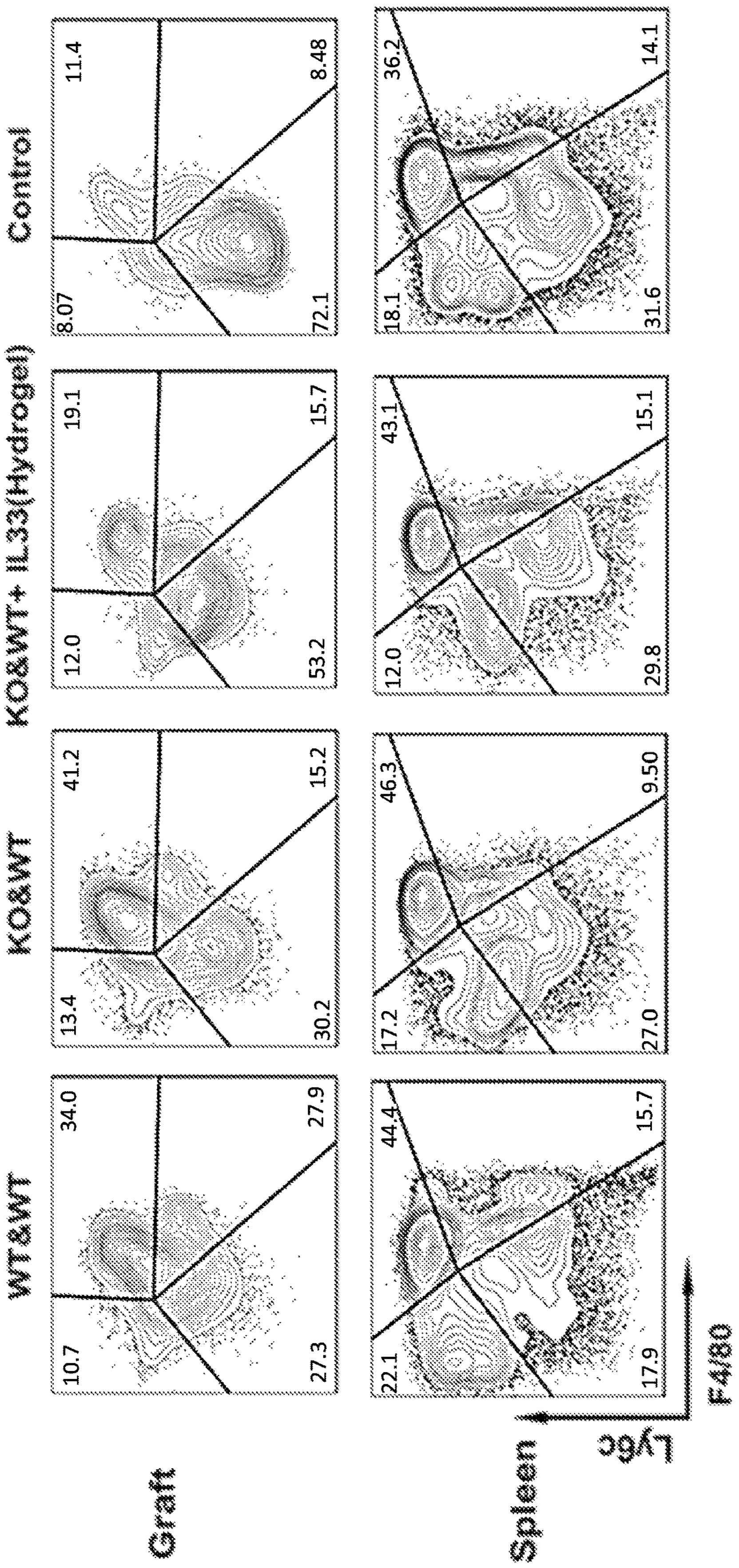
Figure 8C:
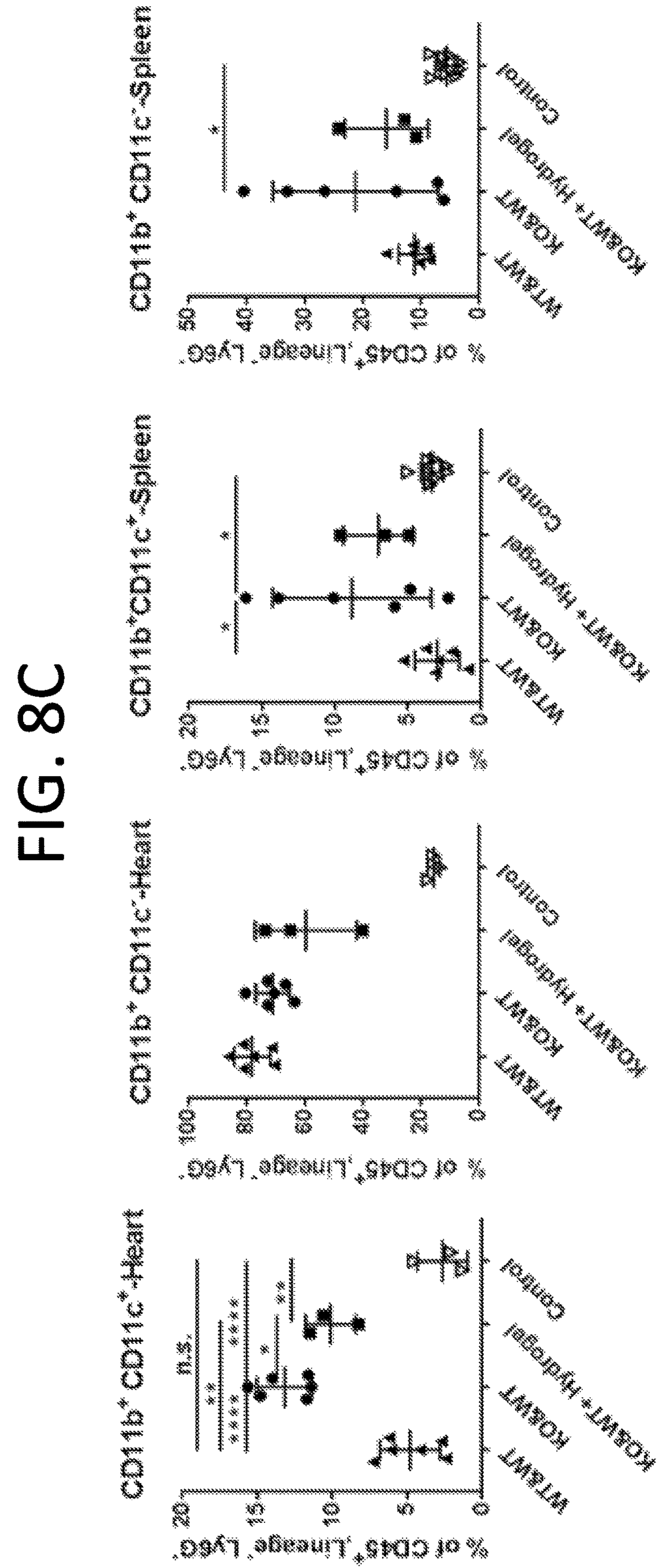
Figure 8D:
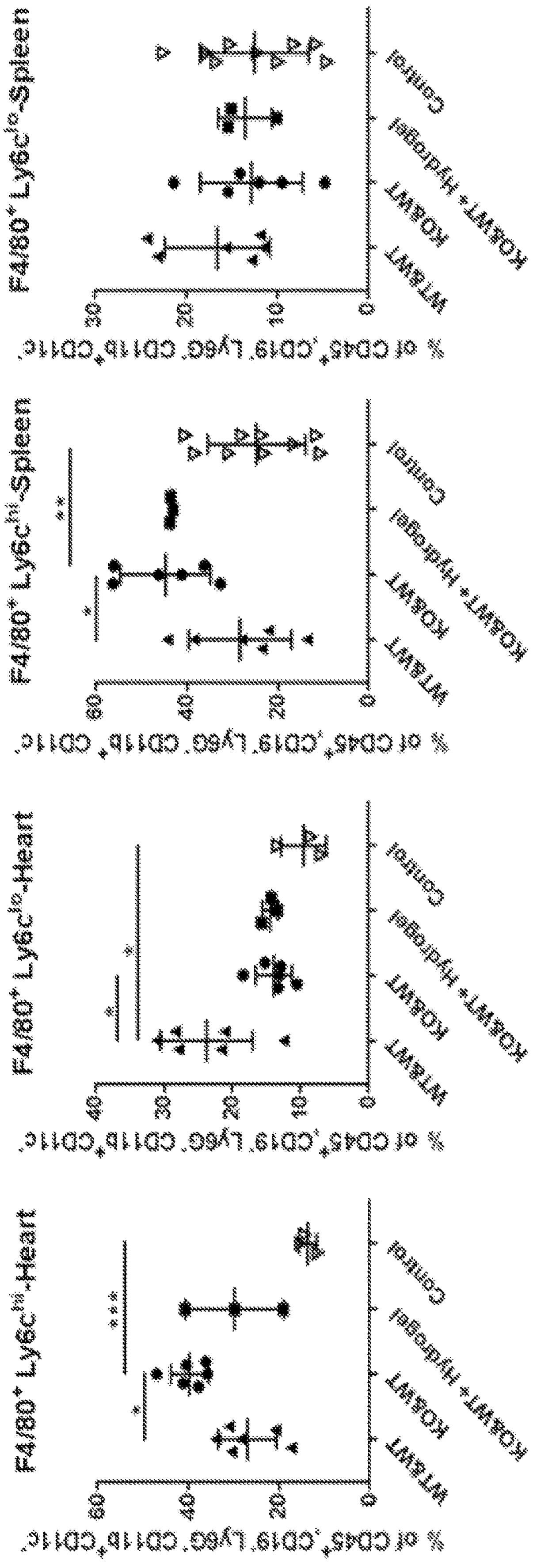

In vitro studies revealed a potent capacity to shift macrophages towards an immunoregulatory and potentially reparative M2 subset (FIGS. 3A-3C, FIGS. 4A-4B). To test the impact of IL-33, including that located in MBV, on heart transplantation outcomes, IL-33-deficient or IL-33-sufficient hearts from Bm12 mice were transplanted into wild type (WT) C57BL/6 (B6) recipient mice. These mice lack IL-33 in both the nucleus and MBV. Bm12 mice express H2-Ab1$^{1bm12}$ that differs from H2-Ab1$^{b}$ by 3 nucleotides resulting in three amino acid substitutions that are recognized as non-self by the immune system of WT B6 mice. In these studies, IL-33-deficient (KO) or IL-33-sufficient Bm12 grafts (WT) were transplanted into B6 recipients and the development of chronic rejection-associated vascular occlusion and fibrosis assessed at day 90-100 post-transplantation (FIGS. 6A-6D). Hematoxylin and eosin (H+E; FIG. 6A) and Tri-chrome staining (FIG. 6B) and computer-aided image analysis confirmed significantly increased vasculopathy (FIG. 6C) and lost muscle fibers/fibrotic disease (FIG. 6D) in HTx lacking IL-33. Thus, the total absence of IL-33 clearly increased the development of chronic rejection.

Example 8

IL-33$^{+}$ MBV Controls the Generation of Inflammatory Myeloid Cells Post Transplantation In mechanistic studies, the effect of a total lack of graft IL-33 and the restoration of IL-33$^{+}$ MBV was investigated, specifically how this impacted the local immune cell that orchestrate chronic rejection. In these studies, leukocytes were isolated and assessed by flow cytometric analysis on post-operation day 3. Leukocytes isolated from naïve Bm12 mice hearts (naïve controls) were included as baseline controls (n=4). Representative dot plots (FIG. 7A-7D) were generated from the flow cytometric analysis and statistical analysis are depicted (P values were generated by one-way analysis of variance (ANOVA), *P<0.05, P<0.01, *P<0.005, **P<0.001). Heart transplants lacking IL-33 had a significantly increased early inflammatory response exemplified in the presence of local inflammatory myeloid cells, such as monocyte-derived dendritic cells (monoDC) (FIGS. 7A-7B: CD45$^{+}$ CD11b$^{+}$ CD11c$^{+}$ F4-80$_{lo}$ MHCII$^{hi}$) and inflammatory macrophages (FIGS. 7C-7D; CD45+ CD11b$^{+}$ F4-80$^{hi}$ Ly6c$^{hi}$ MHCII$^{hi}$) early after Tx. This increase in inflammatory myeloid cells could be corrected by restoration of local IL-33 using IL-33$^{+}$ MBV (FIGS. 8A-8D). This is demonstrated through a significant reduction in CD11b+ CD11c$^{hi}$ monoDC (FIGS. 8A, 8C) and CD11b$^{+}$ F4/80$^{hi}$ Ly6c$^{hi}$ inflammatory macrophages (FIGS. 8B, 8**D) in the heart grafts. In total, these data identify IL-33 in MBV as an important local factor that controls the generation of inflammatory myeloid cell in the graft post transplantation.

Reducing local inflammation can limit early rejection and subsequent development of chronic rejection. All solid organs (heart, kidney, liver, lung) suffer a form of chronic rejection that involves fibrotic disease and accelerated vascular pathology. Based on the findings in a commonly utilized rodent solid transplant model, local IL-33$^{+}$ MBV delivery immediately after other solid organ transplants acts to limit the inflammatory capacity of local myeloid cell and promote improved transplant outcomes. Inflammation due to extended ischemia times and tissue damage early after solid organ transplant is associated with poor transplant outcomes and increased acute and chronic rejection. Conversely, the best transplant outcomes are observed follow living donor transplants where short ischemia times reduce/limit the inflammatory responses mediated by infiltrating innate myeloid cells. Current immunosuppressant agents utilized post-transplant predominantly target adaptive immune cells (T cells and B cells). Excluding steroids, they are ineffective against innate immune cells. These drugs typically do not have a potent impact on innate cells which initiate rejection responses. Thus, the combination of MBV to target innate myeloid cells and adaptive immune cell targeting immunosuppressants are a highly effective combination.

Example 9

Materials and Methods for Examples 7-8

Animals: C57BL/6 (B6) and Bm12 mice were purchased from Jackson Laboratories. The il33$^{-/-}$ mice were a gift from S. Nakae (University of Tokyo, Tokyo, Japan)[84]. Bm12×il33$^{-/-}$ mice were generated by 6 times backcrossing Bm12 mice on to the il33$^{-/-}$ background. St2$^{-/-}$ mice were originally generated on a BALB/c background as described[85] and obtained from Dr. Anne Sperling (University of Chicago) after they were backcrossed 7 times onto the C57BL/6 background. These mice were then backcrossed 3 additional times onto the C57BL/6 background. Animals were housed in a specific pathogen-free facility.

Vascularized heart transplantation: B6 Bm12 which have 3 amino acid substitutions in their H2-Ab1$^{b}$ compare to wild type (WT) B6 mice are commonly used as heart transplant donors in mouse models of chronic rejection. By crossing Bm12 mice with IL-33 deficient B6 mice, we could to define the role IL-33 in chronic rejection. Bm12 or Bm12×il33$^{-/-}$ hearts were transplanted heterotopically in the abdomen of C57BL/6 or C57BL/6 il33$^{-/-}$ recipients. Briefly, donor hearts were transplanted into recipients through end-to-side anastomosis of the donor ascending aorta and pulmonary artery to recipient abdominal aorta and inferior vena cava, respectively. Graft function was assessed daily by abdominal palpation of heart contractions. In some experiments, IL-33$^{-/-}$ MBV was diluted in porcine-derived UBM hydrogel to final concentration of 1 mg/ml MBV. Grafts were covered in hydrogel containing 40 μg diluted MBV after reperfusion of the graft. The gut was replaced and allowed to resume its normal position around the grafted heart while the MBV in hydrogel stably adhered to the heart surface. Graft function was verified daily by abdominal palpation of heart contractions until indicated day of harvest.

Isolation of splenic and graft-infiltrating leukocytes: Mice were anaesthetized and perfused with PBS+0.5% heparin via the left ventricle until the fluid exiting the right ventricle did not contain any visible blood. Spleens were isolated and single cell suspensions generated following mechanical dissociation and RBX lysis. Hearts were then removed, cut into fragments, and homogenized in a Gentle MACS C tube in media containing 350u/ml type IV collagenase and 1 ul/ml DNAse I using program E on a gentleMACS dissociator (Miltenyi Biotec). Single-cell suspensions were then obtained through filtration using a 40 μm cell strainer and centrifuged over a Lympholyte-M (Cedarlane) density gradient at 1500 g for 20 mins. The cells were removed at the interphase using a Pasteur pipette and transferred into a new tube for washing, cell counting, and analysis.

Flow Cytometry: Isolated splenocytes and graft-infiltrating leukocytes were incubated with heat-inactivated goat serum (5%) to block FcR, treated with a Live/Dead distinguishing stain, and then labelled with different combinations of fluorochrome-conjugated Abs (BD Bioscience, Biolegend, eBioscience or MD Biosciences to assess myeloid cell populations. Data was acquired with an LSRFortessa flow cytometer (BD, Biosciences) and analyzed using FlowJo, Version 10.1 (TreeStar).

Histological and Immunohistochemical staining: Naïve mouse hearts and heart transplants were formalin-fixed, paraffin-embedded, sectioned at 4 μm, before being stained with H+E or Masson's Trichrome following standard protocols. Using NearCYTE software (available on the internet through nearctye.org), blue fibrosis$^+$ areas (mm$^2$) were divided by the whole tissue area (mm$^2$) was calculated and multiplied by 100 to give a % Fibrotic Area measure. Percentage arterial occlusion was calculated by manually comparing occluded arteries relative to the total number of arteries in each heart sample.

Example 10

Treatment of Fibrosis

Human lung fibroblasts were isolated from the explanted lungs of interstitial pulmonary fibrosis (IPF) patients and age-matched normal (control) patients. The levels of expression of Col1, Col3, fibronectin, and ACTA2, markers of fibrosis, were determined before and after treatment with MBV. The MBV were isolated from three different source tissues: porcine decellularized urinary bladder matrix (UBM), porcine decellularized lung (pLung), and human lung tissue (hLung). The MBV were added to the culture media at two different concentrations ($1\times10^9$ and $3\times10^9$) particles/ml. The results showed a marked decrease in the expression levels of these markers of fibrosis with all treatments. MBV isolated from decellularized lung provided a more marked decrease. See FIGS. 9A, 9B. Accordingly, administration of MBV can be used as a therapy to decrease fibrosis in lung and other tissues.

It will be apparent that the precise details of the methods or compositions described may be varied or modified without departing from the spirit of the described invention. We claim all such modifications and variations that fall within the scope and spirit of the claims below.

The invention claimed is:

1. A method for treating or inhibiting heart transplant rejection in a subject who has received a hear transplant comprising:

administering to the subject who has received a heart transplant a therapeutically effective amount of isolated nanovesicles derived from an extracellular matrix, wherein the nanovesicles comprise interleukin (IL)-33 and lysyl oxidase, and wherein the nanovesicles a) do not express CD63 or CD81, or b) are CD63$^{lo}$CD81$^{lo}$, thereby treating or inhibiting heart transplant rejection in the subject.

2. The method of claim 1, wherein the extracellular matrix is a mammalian extracellular matrix.

3. The method of claim 2, wherein the mammalian extracellular matrix is a pig, cow, or sheep extracellular matrix.

4. The method of claim 1, wherein the extracellular matrix is from esophageal tissue, urinary bladder, small intestinal submucosa, dermis, umbilical cord, pericardium, cardiac tissue, or skeletal muscle.

5. The method of claim 1, wherein the nanovesicles comprise miR-145 and/or miR-181.

6. The method of claim 1, wherein the nanovesicles are administered to the transplanted heart of the subject.

7. The method of claim 1, wherein the nanovesicles are administered intravenously.

8. The method of claim 1, wherein the nanovesicles are administered weekly, bimonthly or monthly to the subject.

9. The method of claim 1, further comprising administering to the subject an immunosuppressive agent, wherein the immunosuppressive agent is a calcineurin inhibitor, an antiproliferative agent, an mTOR inhibitor, and/or a steroid.

10. The method of claim 9, wherein the calcineurin inhibitor is tacrolimus or cyclosporine; wherein the antiproliferative agent is mycophenolate; wherein the mTOR inhibitor is sirolimus, and/or wherein the steroid is prednisone, hydrocortisone, or cortisone.

11. The method of claim 1, wherein the subject is a human.

12. The method of claim 3, wherein the extracellular matrix is urinary bladder matrix (UBM).

13. The method of claim 3, wherein the extracellular matrix is small intestinal submucosa (SIS) or dermis.

14. A method for treating or inhibiting chronic heart transplant rejection in a subject comprising:

administering to a subject who has received a heart transplant a therapeutically effective amount of isolated nanovesicles derived from a mammalian extracellular matrix, wherein the nanovesicles comprise interleukin (IL)-33 and lysyl oxidase, and wherein the nanovesicles a) do not express CD63 or CD81, or b) are $CD63^{lo}CD81^{lo}$, thereby treating or inhibiting chronic heart transplant rejection in the subject.

15. The method of claim 14, wherein the method decreases monocyte-derived dendritic cells in the heart transplant in the subject.

* * * * *